(12) United States Patent
Vagle

(10) Patent No.: US 10,030,042 B2
(45) Date of Patent: Jul. 24, 2018

(54) SYNTHESIS OF BICYCLIC NUCLEOSIDES

(71) Applicant: MiRagen Therapeutics, Inc., Boulder, CO (US)

(72) Inventor: Kurt Vagle, Boulder, CO (US)

(73) Assignee: MIRAGEN THERAPEUTICS, INC., Boulder, CO (US)

( * ) Notice: Subject to any disclaimer, the term of this patent is extended or adjusted under 35 U.S.C. 154(b) by 0 days.

(21) Appl. No.: 15/122,726

(22) PCT Filed: Mar. 16, 2015

(86) PCT No.: PCT/US2015/020761
§ 371 (c)(1),
(2) Date: Aug. 31, 2016

(87) PCT Pub. No.: WO2015/142735
PCT Pub. Date: Sep. 24, 2015

(65) Prior Publication Data
US 2017/0073368 A1 Mar. 16, 2017

Related U.S. Application Data

(60) Provisional application No. 61/953,889, filed on Mar. 16, 2014.

(51) Int. Cl.
| | | |
|---|---|---|
| *C07H 19/00* | (2006.01) | |
| *C07H 19/16* | (2006.01) | |
| *C12P 19/30* | (2006.01) | |
| *C12P 19/38* | (2006.01) | |
| *C07H 19/06* | (2006.01) | |
| *C07H 19/10* | (2006.01) | |
| *C07H 19/073* | (2006.01) | |
| *C07H 19/173* | (2006.01) | |

(52) U.S. Cl.
CPC ............. *C07H 19/16* (2013.01); *C07H 19/06* (2013.01); *C07H 19/10* (2013.01); *C12P 19/30* (2013.01); *C12P 19/38* (2013.01); *C07H 19/073* (2013.01); *C07H 19/173* (2013.01)

(58) Field of Classification Search
None
See application file for complete search history.

(56) References Cited

U.S. PATENT DOCUMENTS

2003/0028013 A1 2/2003 Wang et al.

FOREIGN PATENT DOCUMENTS

| WO | WO 2011/085102 A1 | 7/2011 |
| WO | WO 2013/036868 A1 | 3/2013 |
| WO | WO 2014/145356 A1 | 9/2014 |

OTHER PUBLICATIONS

Seth et al. J. Org. Chem. (2010), vol. 75, pp. 1569-1581.*
Wang et al. Tetrahedron (1999), vol. 55, pp. 7707-7724.*
Cumpstey, "Intramolecular aglycon delivery," Carbohydrate Res. 343:1553-1573 (2008).
International Search Report, PCT appl. No. PCT/US2015/020761, 3 pages (dated Jun. 18, 2015).
Written Opinion of the International Searching Authority, PCT appl. No. PCT/US2015/020761, 5 pages (dated Jun. 18, 2015).
Ioannidis et al., "Synthesis of Some 2',3'-Dideoxy-2'-C-Methyl-Substituted Nucleosides," Nucleosides & Nucleotides, 11(6):1205-1218 (1992).
Li and Piccirilli, "Efficient synthesis of 2'-C-α-aminomethyl-2'-deoxynucleosides," Chem. Commun. 48:8754-8756 (2012).
Li and Piccirilli, "Synthesis of 2'-Deoxy-2'-C-α-methylpurine Nucleosides," Synthesis 17:2865-2870 (2005).
Li and Piccirilli, "Synthesis of the Phosphoramidite Derivatives of 2'-Deoxy-2'-C-α-methylcytidine and 2'-Deoxy-2'-C-α-hydroxymethylcytidine: Analogues for Chemical Dissection of RNA's 2'-Hydroxyl Group," J. Org. Chem. 69:4751-4759 (2004).
Extended European Search Report, EP appl. No. 15764239.8, 9 pages (dated Jul. 27, 2017).

* cited by examiner

*Primary Examiner* — Patrick T Lewis
(74) *Attorney, Agent, or Firm* — Cooley LLP

(57) ABSTRACT

The present disclosure provides methods for synthesizing modified nucleosides, nucleotides, and oligonucleotides comprising at least one 2'-C-Bridged Bicyclic Nucleotide, and to intermediates used in the process.

25 Claims, 12 Drawing Sheets

FIGURE 3A

| Modification | LNA | aminoLNA | oxoENA | aminoENA |
|---|---|---|---|---|
| Structure | (structure) | (structure) | (structure) | (structure) |
| $\Delta T_m$, PO BB, RNA Complement, vs. dT Single Mod | +9 °C/Mod* | +6.6 °C/Mod* | NA | +2.5-4.0 °C/Mod# |
| $\Delta T_m$, PO BB, RNA Complement, vs. dT Multiple Mods | +5-7 °C/Mod* | +6.3 °C/Mod* | +3.5-5.2 °C/Mod** | NA |

*Literature value, 9-mer
**Literature value, 12-mer

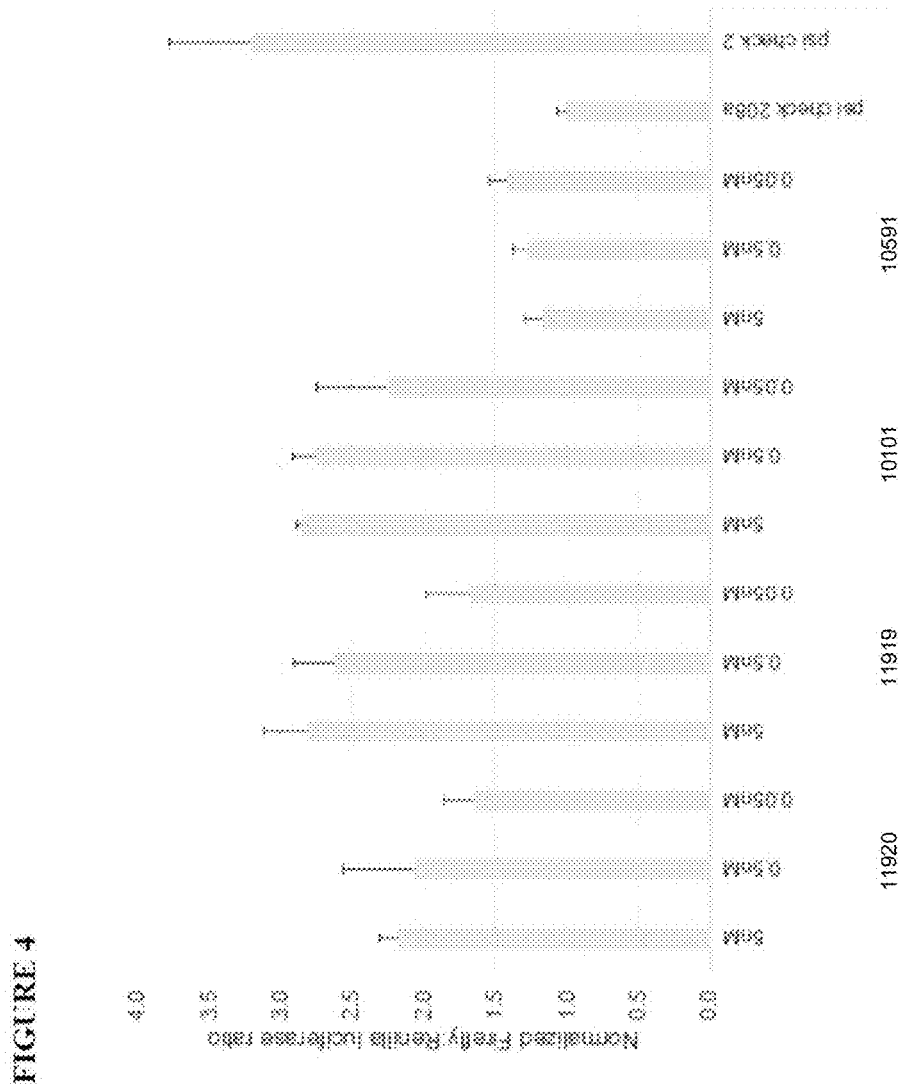

SYNTHESIS OF BICYCLIC NUCLEOSIDES

CROSS REFERENCE TO RELATED APPLICATIONS

This application is a National Stage application, filed pursuant to 35 U.S.C. § 371, of International Application no. PCT/US2015/020761, filed on Mar. 16, 2015, which claims the benefit of priority to U.S. Provisional Application No. 61/953,889, filed Mar. 16, 2014, the entire contents of which are hereby incorporated by reference in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_044_01US_SeqList_ST25.txt, date created: Dec. 1, 2017, file size 8.59 kilobytes.

FIELD OF THE DISCLOSURE

The present disclosure relates to processes for synthesizing modified nucleosides, nucleotides, and oligonucleotides comprising at least one 2'-C-Bridged Bicyclic Nucleotide, and to intermediates used in the process.

BACKGROUND

Modified oligonucleotides including at least one 2'-C-Bridged Bicyclic Nucleotide can provide advantages in potency, efficiency of delivery, target specificity, stability, and/or toxicity. Accordingly, methods for efficiently synthesizing 2'-C-Bridged Bicyclic Nucleotides for incorporation into such oligonucleotides are needed.

SUMMARY OF THE DISCLOSURE

The present disclosure relates to methods for producing 2'-C-Bridged Bicyclic Nucleoside or Nucleotides (CBBN), or phosphoramidites thereof, and oligonucleotides comprising at least one 2'-C-Bridged Bicyclic Nucleotide, as well as synthetic intermediates used in the process. In various embodiments, the synthesized oligonucleotides are antisense inhibitors that provide advantages in potency, efficiency of delivery, target specificity, stability, and/or toxicity.

In one aspect, the disclosure provides methods for producing a β-anomer of a 2'C-Bridged Bicyclic Nucleoside or Nucleotide (CBBN). The method includes a step of glycosylating a nucleobase (for example, a persilylated nucleobase), wherein the glycosyl donor contains a protected alkylhydroxy at the 2' position. The glycosylation step is followed by a cyclizing step wherein the 2' and 4' position of the glycosyl group is cyclized. In an embodiment, the method may further comprise a step of purifying or recovering the β-anomer of the 2'C-Bridged Bicyclic Nucleoside or Nucleotide (CBBN).

In an embodiment, the 2'C-Bridged Bicyclic Nucleoside or Nucleotide has the structure of Formula I:

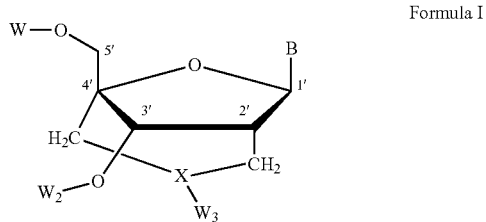

Formula I wherein X is N, S, or O. In one embodiment, X is N, forming an amino group with $W_3$. In another embodiment, X is S. In a further embodiment, X is O. $W_1$ and $W_2$ are independently H, an alcohol protecting group, a phosphate ester comprising the O depicted, a phosphorothioate ester comprising the O depicted, di- or tri-phosphate, or phosphoramidite. $W_3$ independently is null, H, O, an amine protecting group, phosphoramidite, a phosphoramidate ester comprising the O when X is O, a phosphordiamidate ester comprising the O when X is O, methyl, alkyl, cycloalkyl, carboxamide, a sugar, a fatty acid, or other conjugated molecules described herein, —C(O)R, or —COOR, wherein R is aryl, linear alkyl, branched alkyl, cyclic alkyl linear alkenyl, branched alkenyl, cyclic alkenyl, sugar, fatty acid, or other molecular conjugate such as a drug conjugate. B is a nucleobase. In some embodiments, the nucleobase is a pyrimidine base. In other embodiments, the nucleobase is a purine base.

In one embodiment, $W_3$ is independently selected from null, H, O, an amine protecting group, phosphoramidite, a phosphoramidate ester comprising the N when X is N, a phosphordiamidate ester comprising the N when X is N, methyl, alkyl, cycloalkyl, carboxamide, a sugar, a fatty acid, other molecular conjugate, —$C_1$(O)R, or —COOR, wherein R is aryl; linear, branched or cyclic alkyl or alkenyl; sugar, fatty acid, or other molecular conjugate such as a drug conjugate.

Further, in some aspects, when X is S, $W_3$ can be either =O or (=O)$_2$.

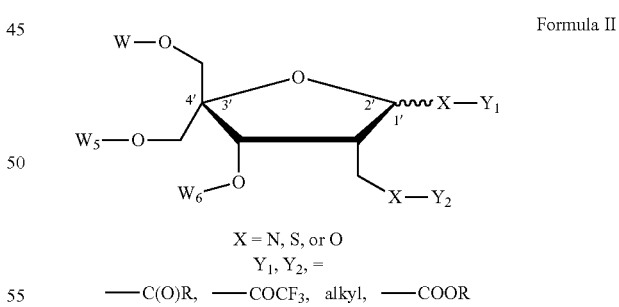

Formula II

X = N, S, or O
$Y_1, Y_2,$ =
—C(O)R, —COCF$_3$, alkyl, —COOR

In various embodiments, the glycosylation step involves a glycosyl donor of structure of Formula II, wherein X is N, S, or O. In one embodiment, X is N. In another embodiment, X is S. In a further embodiment, X is O. $W_4$, $W_5$, $W_6$ are independently an alcohol protecting group, alkyl sulfonate ester (comprising the O depicted) or aryl sulfonate ester (comprising the O depicted). $Y_1$ and $Y_2$ independently are H, an amine protecting group, methyl, alkyl, cycloalkyl, carboxamide, a sugar, a fatty acid, or other conjugated molecules described herein, —$C_1$(O)R, or —COOR, wherein R is aryl, linear alkyl, branched alkyl, cyclic alkyl, linear alkenyl, branched alkenyl, cyclic alkenyl, sugar, fatty acid, or other molecular conjugate such as a drug conjugate.

In various embodiments, the glycosylation step involves a glycosyl donor having a protected alkylhydroxy group at the 2' position. In an embodiment, the glycosyl donor contains an acetyl-protected methylhydroxy at the 2' position, and the cyclizing step comprises substitution of the hydroxy with an amine, masked amine or protected amine and cyclizing the 2' and 4' positions. In an embodiment, the glycosyl donor contains an acetyl protectected methylamino substituent at the 2'-position, and the cyclizing step comprises directly cyclizing the 2' and 4' positions. In an embodiment, the glycosyl donor contains an acetyl-protected methylhydroxy at the 2' position, and the cyclizing step comprises substitution of the hydroxy with a thiol, masked thiol or protected thiol and cyclizing the 2' and 4' positions. In another embodiment, the glycosyl donor contains an acetyl-protected methylhydroxy at the 2' position, and the cyclizing step comprises deacetylation of the hydroxyl and cyclizing the 2' and 4' positions to give a 2'C-4'C-Bridged Bicyclic Nucleoside with an ether linkage. In an embodiment, the glycosyl donor contains an alcohol protecting group at the 3' position. In an embodiment, the alcohol protecting group is an optionally substituted benzyl ether. In another embodiment, the alcohol protecting group is heat stable. In various embodiments, the alcohol protecting group may be, acetyl, silyl, or labile ether. In various embodiments, the glycosyl donor is a pentose which may be substituted. In an embodiment, the glycosyl donor is derived from ribose, arabinose, or glucose as a starting material.

In another aspect, the method of the disclosure produces a 2'C-Bridged Bicyclic Nucleoside or Nucleotide with efficiency and at high yields. In an embodiment, the glycosylation step produces a β-anomer yield of greater than 50%. In another embodiment, the glycosylation step produces a β:α anomer ratio of greater than 7:3, greater than 8:2, or greater than 9:1.

In one aspect, the disclosure provides a method for producing a β-anomer of a 2'C-Bridged Bicyclic Nucleoside or Nucleotide, comprising the steps of: a) glycosylating a nucleobase, wherein the glycosyl donor contains a protected alkylhydroxy or alkylamine at the 2' position; and b) cyclizing the 2' and 4' positions of the glycosyl group to give a glycosylated bicyclo[3.2.1]octane ring system.

In certain aspects, the glycosylating comprises a reaction in which a carbohydrate, (a glycosyl donor) is attached to a hydroxyl or other functional group of another molecule (a glycosyl acceptor).

Other aspects and embodiments of the disclosure will be apparent from the following detailed description and examples.

DESCRIPTION OF THE DRAWINGS

FIG. 2A illustrates the incorporation of the thymine nucleobase.

FIG. 2B illustrates the synthesis of a fully protected adenosine oxoCBBN. Incorporation of the adenine nucleobase is followed by a cyclizing step comprised of deacetylation of the hydroxyl, cyclizing the 2' and 4' positions to give a 2'C-4'C-Bridged Bicyclic Nucleoside with an ether linkage, and finally benzoylating the 5'position to give a fully protected 2'C-4'C-Bridged Bicyclic Nucleoside, wherein "X" from Formula I is O.

FIG. 2C illustrates the incorporation of the guanine nucleobase and wherein "X" from Formula I is O.

FIG. 3A provides a comparison chart of the affinity increases ($\Delta T_m$, c/modification) for locked nucleoside (LNA), its aminoLNA counterpart, as well as 2'-O,4'-C-Ethylene-Bridged Nucleoside (oxoENA) and its aminoENA counterpart.

FIG. 4 depicts the efficacy of various miR-208a inhibitors on miR-208a expression as measured in a dual-luciferase reporter assay. The activities of compounds M-10591, M-10101 (SEQ ID NO:10), M-11919 (SEQ ID NO:5), and M-11920 (SEQ ID NO:6) are measured. Compound M-10591 is a non-targeting control. Compound M-10101 (SEQ ID NO:10), a mixed 9 LNA/7 DNA phosphorothioate oligonucleotide, is an optimized miR208a inhibitor. The M10101 compound is described in U.S. Pat. No. 8,642,751, which is herein incorporated by reference in its entirety. Compounds M-11920 (SEQ ID NO:6) and M-11919 (SEQ ID NO:5) are mixed LNA/DNA/aminoCBBN phosphorothioate oligonucleotides where LNA thymidines of the parent compound (M-10101 (SEQ ID NO:10)) are replaced with either 1 or 2 aminoCBBN residues, respectively. As shown, compound M-11919 (SEQ ID NO:5), in which multiple LNA residues are replaced with aminoCBBN residues, retains all activity of the optimized M-10101 (SEQ ID NO: 10) compound.

DETAILED DESCRIPTION OF THE DISCLOSURE

Figure 1:
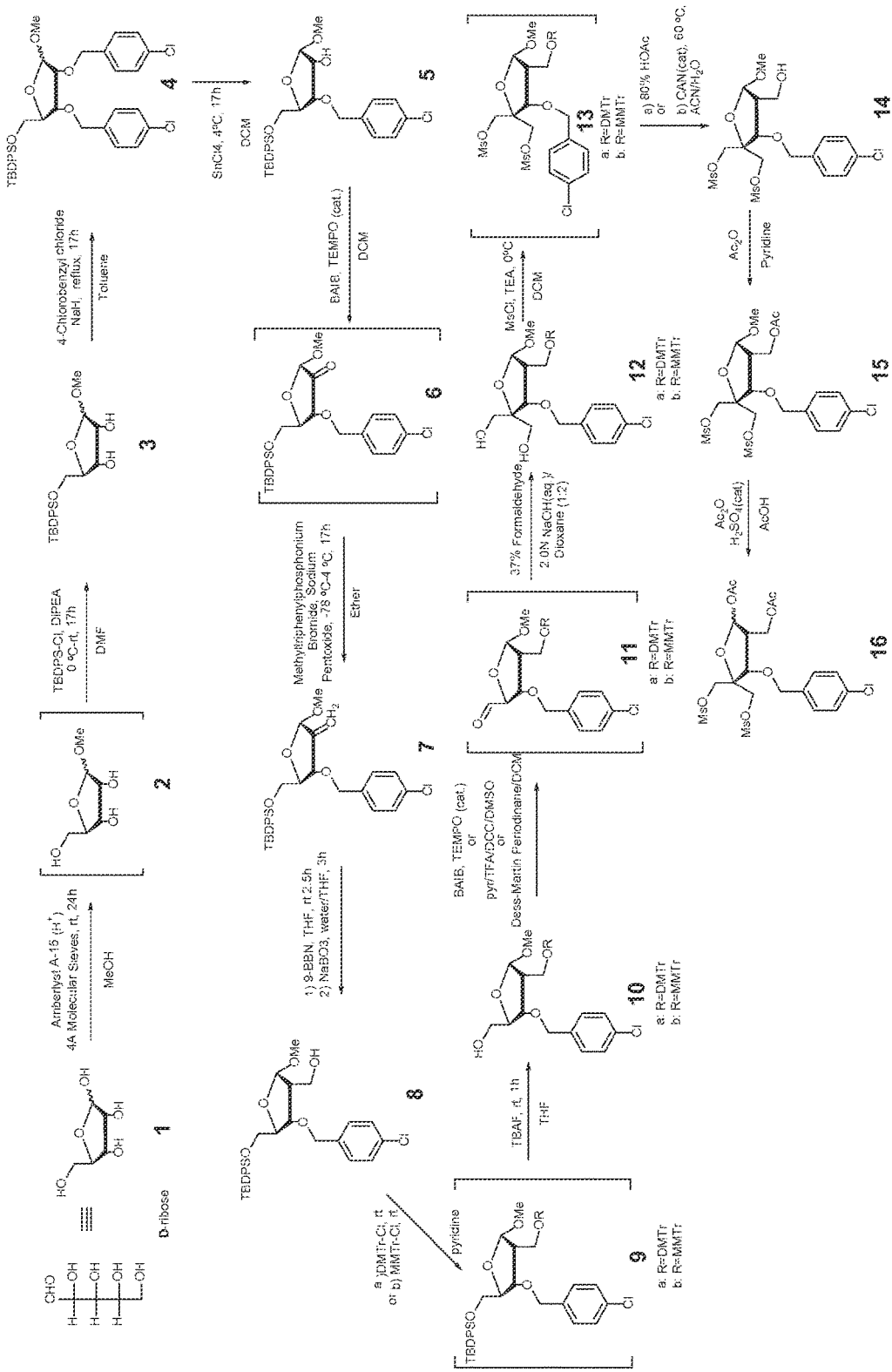
FIG. 1 provides an exemplary synthetic pathway of an amine 2'-C-Bridged Bicyclic Nucleoside.
Figure 1:
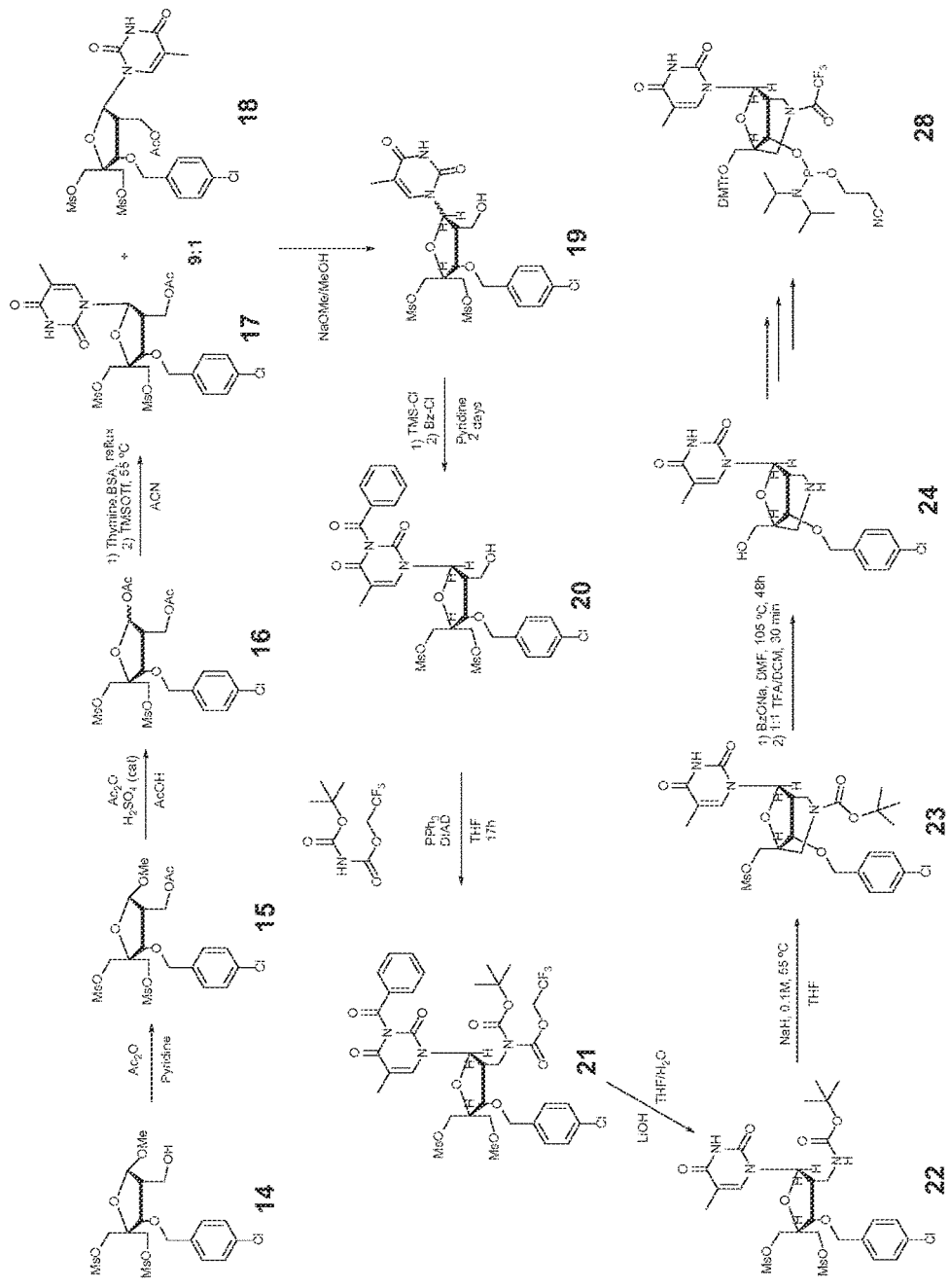
Figure 1:
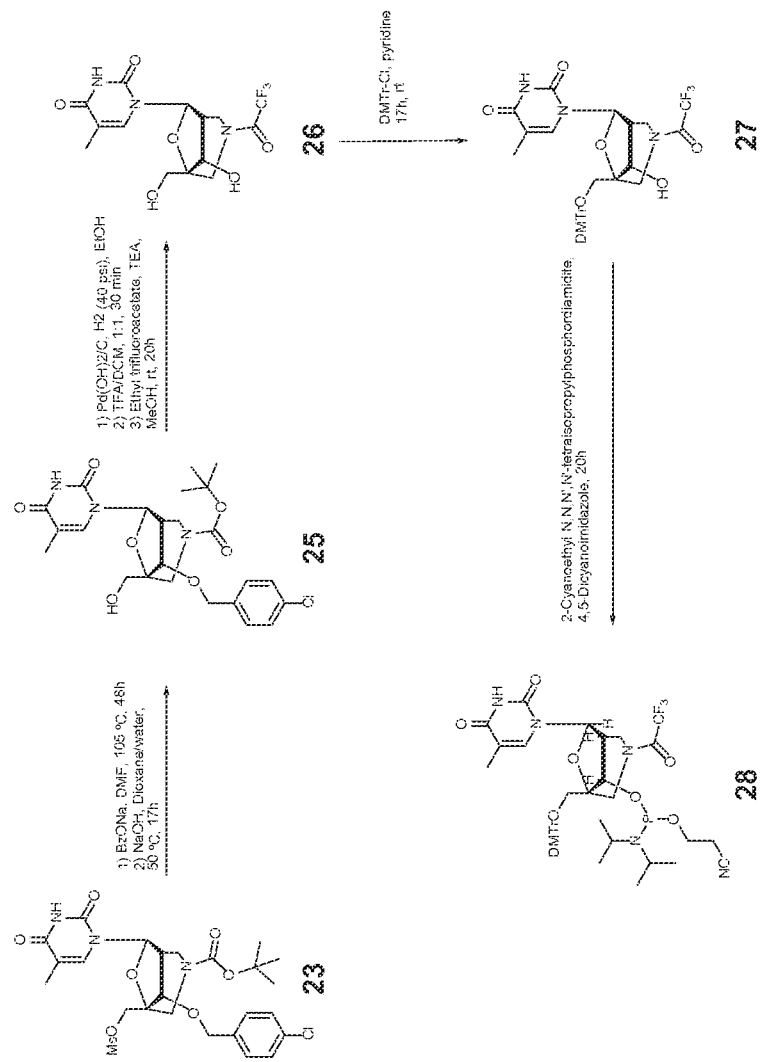

The present disclosure relates to processes for synthesizing modified nucleosides, including 2'-C-Bridged Bicyclic Nucleosides (CBBN), and to intermediates used in the process. In various aspects, the synthesis method provides advantages in cost and convenience by using inexpensive, readily available starting materials and reagents. The method of the disclosure also allows for significantly higher yields.

In one aspect, the disclosure provides methods for producing a β-anomer of a 2'C-Bridged Bicyclic Nucleoside or Nucleotide (CBBN). The method includes a step of glycosylating a nucleobase (for example, a persilylated nucleobase), wherein the glycosyl donor contains a protected alkylhydroxy at the 2' position. The glycosylation step is followed by a cyclizing step wherein the 2' and 4' position of the glycosyl group is cyclized resulting in ring closure. In an embodiment, the method may further comprise a step of purifying or recovering the β-anomer.

In an embodiment, the disclosure relates to the synthesis of a β-anomer of a CBBN having the structure of formula I:

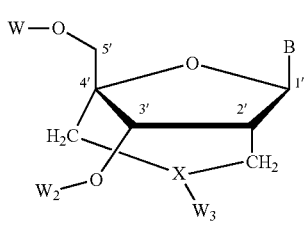

Formula I wherein X is N, S, or O. In one embodiment, X is N. In another embodiment, X is S. In a further embodiment, X is O.

In various embodiments, $W_1$ and $W_2$ are independently H, an alcohol protecting group, a phosphate ester comprising the O depicted, a phosphorothioate ester comprising the O depicted, di- or tri-phosphate, or phosphoramidite. In an embodiment, $W_3$ independently is null, H, O, an amine protecting group, phosphoramidite, a phosphoramidate ester comprising the O when X is O, a phosphordiamidate ester comprising the O when X is O, methyl, alkyl, cycloalkyl, carboxamide, a sugar, a fatty acid, or other conjugated molecules described herein, —$C_{1-4}$(O)R, or —COOR, wherein R is aryl, linear alkyl, branched alkyl, cyclic alkyl, linear alkenyl, branched alkenyl, cyclic alkenyl, sugar, fatty acid, or other molecular conjugate such as a drug conjugate.

In one embodiment, $W_3$ is independently selected from null, H, O, an amine protecting group, phosphoramidite, a phosphoramidate ester comprising the N when X is N, a phosphordiamidate ester comprising the N when X is N, methyl, alkyl, cycloalkyl, carboxamide, a sugar, a fatty acid, other molecular conjugate, —$C_1$(O)R, or —COOR, wherein R is aryl; linear, branched or cyclic alkyl or alkenyl; sugar, fatty acid, or other molecular conjugate such as a drug conjugate.

Further, in some aspects, when X is S, $W_3$ can be either =O or (=O)$_2$.

In various embodiments, the alcohol protecting group is selected from 4,4'-dimethoxytrityl, acetyl, silyl, or acid labile ether. In an embodiment, $W_1$ and $W_2$ each is an alcohol protecting group independently selected from 4,4'-dimethoxytrityl, acetyl, silyl, or acid labile ether. In various embodiments, the amine protecting group is carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), or trifluoroacetyl (tfa). In an embodiment, $W_3$ is an amine protecting group selected from carboxybenzyl, tert-butoxycarbonyl, or trifluoroacetamidyl. In an embodiment, $W_3$ is an alkyl substituent that is not labile, resulting in a tertiary amine.

In various embodiments, 2'-C-Bridged Bicyclic Nucleoside is a 2'-deoxy-2'-C, 4'-C-Bridged Bicyclic Nucleoside (2'-CBBN).

In various embodiments, oxo-2'-C-Bridged Bicyclic Nucleoside is a 2'-deoxy-2'-C, 4'-C-Bridged Bicyclic Nucleoside, wherein 2'C and 4'C are connected through a oxygen resulting in a three atom linkage (—C—O—C—) (oxoCBBN).

In various embodiments, amino-2'-C-Bridged Bicyclic Nucleoside or aza-2'-Bridged Bicyclic Nucleoside is a 2'-deoxy-2'-C, 4'-C-Bridged Bicyclic Nucleoside, wherein 2'C and 4'C are connected through a nitrogen resulting in a three atom linkage (—C—N—C—) (aminoCBBN).

In various embodiments, thio-2'-C-Bridged Bicyclic Nucleoside is a 2'-deoxy-2'-C, 4'-C-Bridged Bicyclic Nucleoside, wherein 2'C and 4'C are connected through a sulfur resulting in a three atom linkage (—C—S—C—) (thioCBBN).

In various embodiments, amino-2'-C-Bridged Bicyclic Nucleotide and thio-2'-C-Bridged Bicyclic Nucleotide are phosphoesters of the amino-2'-C-Bridged Bicyclic Nucleosides and thio-2'-C-Bridged Bicyclic Nucleosides, respectively.

In various embodiments, locked nucleoside is a 2'-oxo-4'-C-Bridged Bicyclic Nucleoside (LNA) that has a 2 atom linkage between the 2' and 4' position of the nucleoside's ribose ring. The core sugar forms a 2.5-dioxabicyclo[2.2.1]heptane structure.

In various embodiments, ENA and oxoENA is a 2'-oxo-4'-C-Bridged Bicyclic Nucleoside that has a 3 atom linkage between the 2' and 4' position of the nucleoside's ribose ring. The core sugar forms a 2.6-dioxabicyclo[3.2.1]octane structure.

In various embodiments, aminoENA and azaENA is a 2'-aza-4'-C-Bridged Bicyclic Nucleoside that has a 3 atom linkage between the 2' and 4' position of the nucleoside's ribose ring. The core sugar forms 6-oxa-2-azabicyclo[3.2.1]octane structure.

In various embodiments, B is a nucleobase. The nucleobase or base can be a purine or a pyrimidine base, which may be modified. In one embodiment, the nucleobase is a purine base. In another embodiment, the nucleobase is a pyrimidine base. In various embodiments, the nucleobase can be selected from natural nucleosidic bases such as adenine, guanine, uracil, thymine, and cytosine, or derivatives and or substitutes thereof. In addition, the present disclosure also contemplates the use of non-naturally occurring nucleobases. In certain embodiments, the non-naturally occurring nucleobase can be a base in which any of the ring atoms of the nucleobases is replaced by another atom. For example, CH may be replaced by N and vice versa. Such modifications can occur at more than one position. Another example of a non-naturally occurring base is a base in which the 2- and 4-substituents of a naturally occurring base are reversed. Additional purine and/or pyrimidine base modifications are described in WO 2012/061810, which is hereby incorporated by reference in its entirety. In some embodiments, the base modification is an amino carbonyl, such as a carboxamino, carbamoyl, or carbamide group. The modification in various embodiments is at the C-5 position of one or more pyrimidine bases, and/or at the C-8 position of one or more purine bases. Exemplary nucleobases include, but are not limited to, 9-N-adenine, 9-N-guanine, thymidine, cytidine, uridine, 5-methyl-cytosine, inosine, 5-substituted uridine, 5-substituted cytosine, 2-aminoadenosine or 5-methylcytosine.

In various embodiments, the glycosylation step involves a glycosyl donor having a protected alkylhydroxy group at the 2' position, wherein the alkylhydroxy group may be C1-C4 alkylhydroxy. In an embodiment, the glycosyl donor contains an acetyl-protected methylhydroxy at the 2' position.

In certain embodiments, the glycosyl donor contains an alcohol protecting group at the 3' position. In an embodiment, the alcohol protecting group comprises an optionally substituted benzyl ether. In another embodiment, the alcohol protecting group is heat stable. Exemplary alcohol protecting groups include, but are not limited to, acetyl, silyl, or base labile ether. In an embodiment, the alcohol protecting group is 4-halobenzyl. As shown in FIG. 1 (compounds 17 and 18), this scheme provides for a high ratio of the β-anomer.

In various embodiments, the glycosyl donor may be a pentose sugar, which may be substituted. In certain embodiments, the glycosyl donor is derived from, for example, ribose, arabinose, or glucose, which are convenient starting materials.

The 2' and 4' positions may then be cyclized. The 2'-hydroxymethyl can be deprotected and directly cyclized to give the 2'-C, 4'-C-bridged bicyclic nucleoside. Alternately, prior to cyclizing, the deprotected 2'-hydroxymethyl group can be converted to an amine, masked amine or protected amine, then cyclized at the N-center to give amino-2'-C,4'-C-bridged bicyclic nucleoside. Alternately, prior to cyclizing, the deprotected 2'-hydroxymethyl group can be converted to a thiol, masked thiol or protected thiol, then cyclized at the S-center to give thio-2'-C,4'-C-bridged bicyclic nucleoside.

In one aspect, the synthesis method of the disclosure provides advantages in cost, convenience, and safety by using less expensive, more readily available, and safer chemical reagents. In various embodiments, the method of the disclosure produces a 2'C-Bridged Bicyclic Nucleoside or Nucleotide with efficiency and at high yields. In an embodiment, the glycosylation step produces a β-anomer yield of greater than 50%, greater than 60%, greater than 70%, greater than 80%, or greater than 90%. In an embodiment, the glycosylation step produces a β:α anomer ratio of greater than 7:3, greater than 8:2, or greater than 9:1.

In some embodiments, the 2'C-Bridged Bicyclic Nucleoside or Nucleotide is converted to a corresponding phosphoramidite, incorporated into an oligonucleotide by solid-phase synthesis. In various embodiments, the 2'C-Bridged Bicyclic Nucleoside or Nucleotide synthesis may involve one or more intermediates as shown, for example, in FIGS. 1 and 2, including, but are not limited to, Methyl-D-Ribose, Methyl 5-O-(TBDPS)-α,β-D-ribofuranoside, Methyl 5-O-(TBDPS)-2,3-O-bis(4-Chlorobenzyl)-α,β-D-ribofuranoside, Methyl 5-O-(TBDPS)-3-O-(4-Chlorobenzyl)-α-D-ribofuranoside, Methyl 5-O-(TBDPS)-3-O-(4-Chlorobenzyl)-2-oxo-α-D-ribofuranoside, Methyl 5-O-(TBDPS)-3-O-(4-Chlorobenzyl)-2-deoxy-2-methylene-α-D-ribofuranoside, Methyl 5-O-(TBDPS)-3-O-(4-Chlorobenzyl)-2-deoxy-2-α-Hydroxymethyl-α-D-Ribofuranoside, Methyl 3-O-(4-Chlorobenzyl)-2-deoxy-2-α-(4,4'-Dimethoxytrityloxymethyl)-α-D-Ribofuranoside, Methyl 5-Oxo-3-O-(4-Chlorobenzyl)-2-deoxy-2-α-(4,4'-Dimethoxytrityloxymethyl)-α-D-Ribofuranoside, Methyl 4-C-Hydroxymethyl-3-O-(4-Chlorobenzyl)-2-deoxy-2-α-(4,4'-Dimethoxytrityloxymethyl)-α-D-Ribofuranoside, Methyl 5-O-Mesyl-4-C-(Mesyloxymethyl)-3-O-(4-Chlorobenzyl)-2-deoxy-2-α-(Hydroxymethyl)-α-D-Ribofuranoside, ((2S,3R,4S)-2-acetoxy-4-((4-chlorobenzyl)oxy)-5,5-bis(((methylsulfonyl)oxy)methyl)tetrahydrofuran-3-yl)methyl acetate, ((3R,4S)-4-((4-chlorobenzyl)oxy)-2-(thymidin-yl)-5,5-bis(((methylsulfonyl)oxy)methyl)tetrahydrofuran-3-yl)methyl acetate, ((3S,4R)-3-((4-chlorobenzyl)oxy)-4-(hydroxymethyl)-5-(thymidin-yl)tetrahydrofuran-2,2-diyl)bis(methylene) dimethanesulfonate, ((3S,4R)-5-(thymidin-yl)-3-((4-chlorobenzyl)oxy)-4-(hydroxymethyl)tetrahydrofuran-2,2-diyl)bis(methylene) dimethanesulfonate, ((3S,4R,5R)-4-(((tert-butoxy-(2,2,2-trifluoroethoxy)dicarbonyl)amino)methyl)-3-((4-chlorobenzyl)oxy)-5-(3-benzoyl-thymidin-yl)tetrahydrofuran-2,2-diyl)bis(methylene) dimethanesulfonate, ((3S,4R,5R)-4-(((tert-butoxycarbonyl)amino)methyl)-3-((4-chlorobenzyl)oxy)-5-(thymidin-yl)tetrahydrofuran-2,2-diyl)bis(methylene) dimethanesulfonate, (1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate, 1-((1R,5R,7R,8S)-8-((4-chlorobenzyl)oxy)-5-(hydroxymethyl)-6-oxa-3-azabicyclo[3.2.1]octan-7-yl)-thymidine, (1R,5R,7R,8S)-tert-butyl 8-((4-chlorobenzyl)oxy)-7-(thymidin-yl)-5-(hydroxymethyl)-6-oxa-3-azabicyclo[3.2.1]octane-3-carboxylate, (1R,5R,7R,8S)-8-Hydroxy-7-(thymidin-yl)-5-(hydroxymethyl)-3-(2,2,2-trifluoroacetyl)-6-oxa-3-azabicyclo[3.2.1]octane, (1R,5R,7R,8S)-8-Hydroxy-7-(thymidin-yl)-5-((4,4'-dimethoxytrityloxy)methyl)-3-(2,2,2-trifluoroacetyl)-6-oxa-3-azabicyclo[3.2.1]octane, (1R,5R,7R,8S)-7-(thymidin-yl)-5-((4,4'-dimethoxytrityloxy)methyl)-3-(2,2,2-trifluoroacetyl)-6,8-oxa-3-azabicyclo[3.2.1]octane-8-O-(2-cyanoethyl)-N,N-diisopropylphosphoramidite, ((3R,4S)-4-((4-chlorobenzyl)oxy)-2-(6-N-Benzoyladenosin-yl)-5,5-bis(((methylsulfonyl)oxy)methyl)tetrahydrofuran-3-yl)methyl acetate, ((3R,4S)-4-((4-chlorobenzyl)oxy)-2-(6-N-isobutyrylguanosin-yl)-5,5-bis(((methylsulfonyl)oxy)methyl)tetrahydrofuran-3-yl)methyl acetate, and {(1R,5R,7R,8S)-7-[(9R)-9a-Benzoyl-9-adenineyl]-8-(4-Chlorobenzyloxy)-3.6-dioxabicyclo[3.2.1]oct-5-yl}methyl benzoate. The protecting groups described in these intermediates can be alternatively substituted with other protecting groups known in the art or described herein, such as 4-monomethoxytrityloxy in place of 4,4'-dimethoxytrityloxy protecting groups.

In some embodiments, the oligonucleotides comprise a sequence that is substantially complementary to a nucleotide sequence of miR-15a or b, miR-29, miR-92, miR-143, miR-145, miR-195, miR-206, miR-208a, miR-208b, miR-378, miR-451 and/or miR-499. In exemplary embodiments, the oligonucleotides may comprise a sequence that is substantially complementary to a human miR-208a, miR-208b, miR-378, miR-451 and/or miR-499 sequence. In certain embodiments, the oligonucleotides may comprise a sequence that is substantially identical to a human miR-208a, miR-208b, miR-378, miR-451 and/or miR-499 sequence. As used herein, "substantially complementary" or "substantially identical" refers to a sequence that is at least about 70%, about 75%, about 80%, about 85%, about 90%, about 91%, about 92%, about 93%, about 94%, about 95%, about 96%, about 97%, about 98%, or about 99% complementary or identical to a target polynucleotide sequence.

The synthesis of oligonucleotides, including modified polynucleotides, by solid phase synthesis is well known and is reviewed by Caruthers et al., "New Chemical Methods for Synthesizing Polynucleotides," *Nucleic Acids Symp. Ser.*, (7):215-23 (1980) which is hereby incorporated by reference in its entirety. The synthesis of oligonucleotides will vary depending on the selected nucleotide monomer(s) utilized. In exemplary embodiments, the nucleotide monomers used for synthesis include, but are not limited to, dimethoxytrityl (DMTr)-protected amine 2'-C-Bridged Bicyclic Nucleoside phosphoramidite, an internal phosphoramidite derivative of a DMTr-protected amine 2'-C-Bridged Bicyclic Nucleoside, DMTr- and trifluoroacetate-protected amine 2'-C-Bridged Bicyclic Nucleoside phosphoramidite, DMTr-protected fatty acid conjugated amine 2'-C-Bridged Bicyclic Nucleoside phosphoramidite, and DMTr-protected sugar conjugated amine 2'-C-Bridged Bicyclic Nucleoside phosphoramidite. In certain embodiments, extended coupling time may be required for oligonucleotide synthesis utilizing dimethoxytrityl (DMTr)-protected amine 2'-C-Bridged Bicyclic Nucleoside phosphoramidite, DMTr- and trifluoroacetate-protected amine 2'-C-Bridged Bicyclic Nucleoside phosphoramidite, DMTr-protected fatty acid conjugated amine 2'-C-Bridged Bicyclic Nucleoside phosphoramidite, and DMTr-protected sugar conjugated amine 2'-C-Bridged Bicyclic Nucleoside phosphoramidite. In certain embodiments, for oligonucleotide synthesis involving an internal phosphoramidite derivative of a DMTr-protected amine 2'-C-Bridged Bicyclic Nucleoside, the standard oligonucleotide synthesis cycle may be modified by replacing the normal capping reagent utilizing $Ac_2O$/base with a non-standard capping reagent. Alternatively, synthesis may be modified by treating the newly coupled oligonucleotide with an amine reactive conjugate or protecting group that is stable to the synthesis cycle (but if desired, can be removed later) immediately after the phosphoramidite coupling cycle, but before the standard capping step.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art.

EXAMPLES

Example 1: Production of Amino 2'-C-4'C-Brided Bicyclic Nucleosides

This example describes the synthesis of key intermediates for the production of amine 2'-C-Bridged Bicyclic Nucleosides (see FIG. 1).

Methyl-D-Ribose (2)

In three 500 mL Schott Bottles were D-ribose (1) (90 g, 599 mmol), Amberlyst 15 (H+) (90 g, 599 mmol), and Molecular Trap Pack (90 g, 599 mmol) divided equally (i.e. 30 g each in each Schott bottle). Each bottle was filled with an equal amount of methanol (Volume: 1350 ml, i.e., 450 mL/bottle) to give a colorless solution. All bottles were placed on an orbital shaker @ 250 rpm/25° C. for 17 hours. Reaction progress was monitored by TLC of the reaction mixture compared to co-spot with unprotected ribose in 15% MeOH/DCM as developing solvent. The sugars were visualized via Hannessian's Stain with charring.

The solutions were filtered through a glass sintered funnel. The catalyst and Molecular Trap Packs were washed with excess MeOH (approximately 500 mL/Bottle that contained 30 g each of Amberlyst and Trap Packs). The methanol solution was made basic by addition of 15 mL of TEA (5 mL/reaction bottle). The mixtures were concentrated to dryness. The residue was co-evaporated with dichloromethane (3×200 mL) to azeotrope off residual MeOH. The residue was dried under high vacuum overnight to give 97.55 g (99%) of methyl-D-ribose (2) which was used without further purification.

Methyl 5-O-(TBDPS)-α,β-D-ribofuranoside(3)

In a 1 L round-bottomed flask was methyl-D-ribose (2, 60.12 g, 366 mmol) and DIEA (128 ml, 732 mmol) dissolved in DMF (Volume: 400 ml) to give a colorless solution. The flask was flushed with argon and cooled to 0° C. in an ice bath. TBDPS-Cl (99 ml, 385 mmol) was added dropwise over 10 minutes and the mixture was allowed to come to room temperature overnight.

The reaction mixture was poured into a solution of saturated NaHCO$_3$ (1 L). The aqueous phase was extracted with EtOAc (3×300 mL). The organic phases were combined and washed with water (1×400 mL) and brine (1×400 mL). The organic phase was dried over Na$_2$SO$_4$, filtered and concentrated to give a dark brown oil that was purified by dividing into 4 equal portions and purifying via silica chromatography running a standard 0-100% EtOAc/Hex gradient over 75 minutes at 100 mL/min followed by a 7 minute hold @ 100% EtOAc. Pure fractions were combined to give 121.59 g (82%) of methyl 5-O-(TBDPS)-α,β-D-ribofuranoside (3) as a colorless oil.

Methyl 5-O-(TBDPS)-2,3-O-bis(4-Chlorobenzyl)-α,β-D-ribofuranoside (4)

In a 2 L round-bottomed flask was weighed Methyl 5-O-(TBDPS)-α,β-D-ribofuranoside (3, 55.0 g, 137 mmol). The material was co-evaporated with toluene (2×100 mL) at 40° C. and high vacuum. The flask was fitted with a reflux condenser and the starting material was dissolved under argon in Toluene (Volume: 500 ml). Sodium hydride (21.86 g, 547 mmol) was added in ~5 g portions to give a gray suspension. The mixture was heated to 60° C. for 30 minutes and then cooled to room temperature with an ice bath. 1-chloro-4-(chloromethyl)benzene (66.0 g, 410 mmol) was added in ~15 g portions with vigorous stirring. The mixture was heated and stirred overnight at reflux.

The reaction mixture was cooled to 0° C. and diluted with 500 mL of EtOAc. The mixture was quenched by slow addition of EtOH (50 mL) to minimize bubbling. The mixture was further diluted to 1.5 L with EtOAc and Washed with 10% Na$_2$CO$_3$ (2×500 mL) and sat NaCl (1×500 mL). The organic was dried over Na$_2$SO$_4$, filtered and concentrated. The crude product was purified via silica gel chromatography. Product was eluted with a 0-30% EtOAc/Hexanes gradient. Pure collected fractions were combined to give methyl 5-O-(TBDPS)-2,3-O-bis(4-chlorobenzyl)-α,β-D-ribofuranoside (4, 62.15 g, 70%) as an amber oil.

Methyl 5-O-(TBDPS)-3-O-(4-Chlorobenzyl)-α-D-ribofuranoside (5)

In a 1 L round-bottomed flask was methyl 5-O-(TBDPS)-2,3-O-bis(4-chlorobenzyl)-α,β-D-ribofuranoside (4, 65 g, 100 mmol) dissolved in 600 mL DCM to give a yellow solution. The mixture was cooled to 0° C. under argon. Tin (IV) Chloride (150 ml, 150 mmol) was added slowly over 10 minutes while solution turns to a clear, dark brown solution. The reaction mixture was stored overnight at 4° C., under argon with stirring.

The reaction mixture was diluted with DCM (250 mL) and added to 500 mL of DI water in a 4 L sep funnel. The mixture was shaken vigorously and allowed to separate. All organic and emulsion/precipitate was retained and washed with a second aliquot of 500 mL water. All organic and emulsion/precipitate was retained and washed with 500 mL of 10% Na$_2$CO$_3$ in water. The emulsion was reduced via addition of MeOH and mechanical agitation. All organic and emulsion/precipitate was retained and finally washed with 500 mL brine. Again, the emulsion was reduced via addition of MeOH and mechanical agitation. The organic phase was removed and dried via MgSO$_4$ suspension. The remaining emulsion and aqueous phase was extracted with additional DCM (2×100 mL) which was combined with the MgSO$_4$ suspension. The organic phase was filtered and concentrated to a brown oil. The crude product was purified via silica gel column chromatography with a 0-30% EtOAc/Hexanes gradient. Pure collected fractions were combined to give methyl 5-O-(TBDPS)-3-O-(4-chlorobenzyl)-α-D-ribofuranoside (5, 41.20 g, 78%) as an amber oil.

Methyl 5-O-(TBDPS)-3-O-(4-Chlorobenzyl)-2-oxo-α-D-ribofuranoside (6)

In a 1 L round-bottomed flask was dissolved methyl 5-O-(TBDPS)-3-O-(4-chlorobenzyl)-α-D-ribofuranoside (5, 41.00 g, 78 mmol) and TEMPO (1.215 g, 7.78 mmol) in DCM (Volume: 250 ml) to give an orange solution. Iodobenzene diacetate (37.6 g, 117 mmol) was added and the mixture was allowed to stir overnight at room temperature.

Reaction mixture was diluted to 500 mL with DCM and washed with saturated sodium thiosulfate solution (2×300 mL), and brine (1×300 mL). The organic phase was dried over MgSO$_4$, filtered and concentrated. The orange residue was dried under high vacuum at 50° C. for 3 h. The crude methyl 5-O-(TBDPS)-3-O-(4-chlorobenzyl)-2-oxo-α-D-ribofuranoside (6, 40.50, "99%") as an amber oil was used as is for subsequent reaction.

Methyl 5-O-(TBDPS)-3-O-(4-Chlorobenzyl)-2-deoxy-2-methylene-α-D-ribofuranoside (7)

In a 2000 mL round-bottomed flask, methyltriphenylphosphonium bromide (6, 26.6 g, 75 mmol) was suspended in ether (Ratio: 20.00, Volume: 1500 ml) to give a white suspension. The flask was flushed with argon and cooled to 0° C. in an ice bath. Sodium t-pentoxide (7.39 g, 67 mmol) was dissolved in Benzene (Ratio: 1.000, Volume: 75 ml) and added at once to the suspension. The flask was again flushed with argon and allowed to come to room temperature over 2 hours. The suspension was allowed to stir for an additional 4 hr. The suspension was then cooled to −72° C. in an Acetone/dry ice bath. methyl 5-O-(TBDPS)-3-O-(4-chlorobenzyl)-2-oxo-α-D-ribofuranoside (19.56 g, 37.25 mmol) was dissolved in additional Ether (Ratio: 1.067, Volume: 40 ml). The carbohydrate solution was added via syringe and the reaction mixture was allowed to stir at 4° C. for 17 hours.

TLC revealed that the reaction was complete (15% EtOAc/Hex). The reaction mixture was washed with sat NH$_4$Cl (2×500 mL) and brine (1×250 mL). The aqueous phase was back-extracted with Ether (150 mL). The organic phases were combined and dried with a brine wash (1×250 mL) and addition of Na$_2$SO$_4$. The organic phase was filtered and concentrated. Purification was done via silica gel column chromatography using a 0-20% EtOAc in Hexanes gradient. Pure fractions were combined and concentrated to dryness to give methyl 5-O-(TBDPS)-3-O-(4-chlorobenzyl)-2-deoxy-2-methylene-α-D-ribofuranoside (7, 14.79 g, 28.3 mmol, 76% yield) as a colorless oil.

Methyl 5-O-(TBDPS)-3-O-(4-Chlorobenzyl)-2-deoxy-2-α-Hydroxymethyl-α-D-Ribofuranoside (8)

Under argon, 9-BBN (8.97 g, 73.5 mmol) was added to a solution of methyl 5-O-(TBDPS)-3-O-(4-chlorobenzyl)-2-deoxy-2-methylene-α-D-ribofuranoside (7, 28.50 g, 54.5 mmol) in THF (300 ml) at room temperature. After the reaction mixture was stirred at room temperature for 1.5 hours, TLC revealed that all starting material was consumed.

Sodium perborate tetrahydrate (33.9 g, 221 mmol) and water (80 mL) were added and the mixture was stirred at room temperature for an additional 2 hours. The organic layer was separated, and the aqueous was diluted to 400 mL then extracted with ethyl acetate (3×250 mL). The organic layers were combined and dried over MgSO$_4$. The solvent was removed, and the product was purified by silica gel chromatography eluting with ethyl acetate/hexanes gradient of 0-60%. The purified fractions were combined and concentrated to dryness to give methyl 5-O-(TBDPS)-3-O-(4-chlorobenzyl)-2-deoxy-2-α-hydroxymethyl-α-D-ribofuranoside (8, 26.39 g, 48.8 mmol, 90% yield) as a colorless oil.

Methyl 3-O-(4-Chlorobenzyl)-2-deoxy-2-α-(4,4'-Dimethoxytrityloxymethyl)-α-D-Ribofuranoside (10)

In a 1 L round-bottomed flask was methyl 5-O-(TBDPS)-3-O-(4-chlorobenzyl)-2-deoxy-2-α-hydroxymethyl-α-D-ribofuranoside (8, 26.30 g, 48.6 mmol) in pyridine (200 ml) dissolved under Argon to give a colorless solution. DMTr-Cl (20.58 g, 60.8 mmol) was added, at once, to the stirring solution. The reaction mixture was allowed to stir overnight. The trytilation reaction was quenched by the addition of 50 mL of MeOH with stirring for 20 minutes followed by diluting the mixture to 750 mL with EtOAc. The Organic phase was washed with saturated NaHCO$_3$ solution (3×350 mL) and Brine (1×150 mL). The organic phase was dried over Na$_2$SO$_4$, filtered and concentrated to dryness.

The crude product (9a) was dissolved in THF (Volume: 70 ml). 1.0 M TBAF in THF solution (72.9 ml, 72.9 mmol) was added to the mixture and it was allowed to stir at room temperature for 1.5 hours. Addition of the TBAF resulted in a dark, smoky colored solution. The mixture was concentrated to dryness and applied to a 330 g ISCO silica column pretreated with 3% TEA in hexanes. The product was eluted with a 0-60% EtOAc in Hexanes gradient over 50 minutes @ 100 mL/min. The pure fractions were combined and concentrated to give methyl 3-O-(4-chlorobenzyl)-2-deoxy-2-α-(4,4'-dimethoxytrityloxymethyl)-α-D-ribofuranoside (10, 27.17 g, 44.9 mmol, 92% yield) as a colorless oil.

Methyl 3-O-(4-Chlorobenzyl)-2-deoxy-2-α-(4monomethoxytrityloxymethyl)-α-D-Ribofuranoside (10b)

In a 250 mL round-bottomed flask was methyl 5-O-(TBDPS)-3-O-(4-chlorobenzyl)-2-deoxy-2-α-hydroxymethyl-α-D-ribofuranoside (8, 1.82 g, 3.36 mmol) in pyridine (25 ml) dissolved under Argon to give a colorless solution. MMTr-Cl (1.30 g, 4.20 mmol) was added, at once, to the stirring solution. The reaction mixture was allowed to stir overnight. The trytilation reaction was quenched by the addition of 50 mL of MeOH with stirring for 20 minutes followed by diluting the mixture to 150 mL with EtOAc. The Organic phase was washed with saturated NaHCO$_3$ solution (3×75 mL) and Brine (1×50 mL). The organic phase was dried over Na$_2$SO$_4$, filtered and concentrated to dryness.

The crude product (9b) was dissolved in THF (Volume: 10 ml). 1.0 M TBAF in THF solution (5.0 ml, 5.0 mmol) was added to the mixture and it was allowed to stir at room temperature for 1.5 hours. Addition of the TBAF resulted in a dark, smoky colored solution. The mixture was concentrated to dryness and applied to a 100 g Biotage SNAP silica column pretreated with 3% TEA in hexanes. The product was eluted with a 0-60% EtOAc in hexanes gradient over 30 minutes @ 50 mL/min. The pure fractions were combined and concentrated to give methyl 3-O-(4-chlorobenzyl)-2-deoxy-2-α-(4-monomethoxytrityloxymethyl)-α-D-ribofuranoside (10b, 1.74 g, 3.02 mmol, 90% yield) as a colorless oil.

Methyl 5-Oxo-3-O-(4-Chlorobenzyl)-2-deoxy-2-α-(4,4'-Dimethoxytrityloxymethyl)-α-D-Ribofuranoside (11)

In a 1 L round-bottomed flask was methyl 3-O-(4-chlorobenzyl)-2-deoxy-2-α-(4,4'-dimethoxytrityloxymethyl)-α-D-ribofuranoside (10a, 27.15 g, 44.9 mmol) and DCC (27.8 g, 135 mmol) dissolved in DMSO (166 ml, 2333 mmol) to give a colorless solution. Pyridine (5.44 ml, 67.3 mmol) and TFA (1.728 ml, 22.43 mmol) were combined in 40 mL of DMSO and the resulting solution was added to the reaction mixture. The flask was covered and allowed to stir overnight at room temperature.

Water (25 mL) was added and the reaction was allowed to stir at room temperature for 3 hours. The reaction was diluted with 500 mL EtOAc and filtered. The precipitate was washed with an additional 200 mL of EtOAc. The combined organic was washed with Brine (5×400 mL), dried with Na$_2$SO$_4$, filtered and concentrated. The product was purified via silica gel column chromatography with a 0-100% EtOAc/Hex gradient. Pure fractions were combined and concentrated to give methyl 5-oxo-3-O-(4-chlorobenzyl)-2-deoxy-2-α-(4,4'-dimethoxytrityloxymethyl)-α-D-ribofuranoside (11a, 25.22 g, 41.8 mmol, 93% yield) as a white foam.

Methyl 4-C-Hydroxymethyl-3-O-(4-Chlorobenzyl)-2-deoxy-2-α-(4,4'-Dimethoxytrityloxymethyl)-α-D-Ribofuranoside (12)

In a 2 L round-bottomed flask was methyl 5-oxo-3-O-(4-chlorobenzyl)-2-deoxy-2-α-(4,4'-dimethoxytrityloxymethyl)-α-D-ribofuranoside (11a, 25.20 g, 41.8 mmol) dissolved in Dioxane (1000 ml) to give a colorless solution. Formaldehyde (249 ml, 3343 mmol) was added with stirring. The reaction mixture was cooled to 0° C. in an ice bath. The flask was fitted with a 750 mL pressure equalizing dropping funnel and 2.0 M sodium hydroxide (606 ml, 1212 mmol) was added over 30 minutes to give a cloudy white solution. The mixture was allowed to stir while coming to room temperature over 42 hours. The solution had turned clear. The solution was neutralized by addition of sodium phosphate, monobasic, monohydrate (86 g, 627 mmol). The solution was concentrated to about a third of its volume, diluted with 500 mL of water and extracted with DCM (3×300 mL). The organic layers were combined and washed with brine (1×300 mL) then dried over Na$_2$SO$_4$. The solvent was removed, and the product was purified by silica gel chromatography eluting with a MeOH/DCM gradient of 0-10%. The purified fractions were combined and concentrated to dryness to give methyl 4-C-hydroxymethyl-3-O-(4-chlorobenzyl)-2-deoxy-2-α-(4,4'-dimethoxytrityloxymethyl)-α-D-ribofuranoside (12a, 22.50 g, 35.4 mmol, 85% yield) as a colorless oil.

Methyl 5-O-Mesyl-4-C-(Mesyloxymethyl)-3-O-(4-Chlorobenzyl)-2-deoxy-2-α-(Hydroxymethyl)-α-D-Ribofuranoside (14)

In a 1 L round-bottomed flask was methyl 4-hydroxymethyl-3-O-(4-chlorobenzyl)-2-deoxy-2-α-(4,4'-dimethoxytrityloxymethyl)-α-D-ribofuranoside (12a, 22.50 g, 35.4 mmol) dissolved in Pyridine (200 ml) under Ar to give a colorless solution. The mixture was cooled to 0° C. in an ice bath. Mesyl-Cl (8.28 ml, 106 mmol) was added, dropwise over 10 minutes, to the stirring solution. The reaction mixture was stirred for 45 minutes at room temperature. The mesylation reaction was quenched by cooling the reaction to 0° C. and adding 15 mL of Water with stirring for 20 minutes. The mixture was diluted to 750 mL with EtOAc and washed with brine (3×400 mL). The organic phase was dried over Na$_2$SO$_4$, filtered and concentrated to dryness.

The crude product (13a) was dissolved in 800 mL of AcOH. Water (200 mL) was added to the stirring solution. The solution was allowed to stir at room temperature for 2.5 hours then diluted with 500 mL of water. The mixture was concentrated to about 400 mL and diluted with an additional 250 mL of water. The solution was then concentrated to dryness under high vacuum. The residue was applied to a 220 g ISCO silica column and the product was eluted with a 0-100% EtOAc/Hexanes gradient. The pure fractions were combined and concentrated to give methyl 5-O-mesyl-4-C-(mesyloxymethyl)-3-O-(4-chlorobenzyl)-2-deoxy-2-α-(Hydroxymethyl)-α-D-ribofuranoside (14, 10.01 g, 20.47 mmol, 57.8% yield) as a colorless oil.

Alternately, the crude product (13b) ((3S,4R,5S)-3-((4-chlorobenzyl)oxy)-5-methoxy-4-((4-monomethoxytryloxy)methyl)tetrahydrofuran-2,2-diyl)bis(methylene) dimethanesulfonate (1.60 g, 2.10 mmol) was weighed into a 200 mL round bottomed flask with a stir bar. The flask is charged with acetonitrile and set to stir until carbohydrate is completely dissolved. Water, followed by ceric ammonium nitrate (0.115 g, 0.21 mmol) was added to the stirring solution. The mixture was covered and heated to 60° C. for 1 h. The solution is cooled to room temperature and poured into a brine solution (500 mL). The aqueous phase is extracted with ethyl acetate (3×100 mL). The organic phases are combined and dried over sodium sulfate, filtered and concentrated. The resultant material is applied to a 50 g Biotage SNAP silica gel column and eluted with a 0-100% EtOAc/Hexanes gradient. The pure fractions were combined and concentrated to give methyl 5-O-mesyl-4-C-(mesyloxymethyl)-3-O-(4-chlorobenzyl)-2-deoxy-2-α-(Hydroxymethyl)-α-D-ribofuranoside (14, 0.94 g, 91.5%) as a colorless oil.

((2S,3R,4S)-2-acetoxy-4-((4-chlorobenzyl)oxy)-5,5-bis(((methylsulfonyl)oxy)methyl)tetrahydrofuran-3-yl)methyl acetate (16)

((3S,4R,5S)-3-((4-chlorobenzyl)oxy)-4-(hydroxymethyl)-5-methoxytetrahydrofuran-2,2-diyl)bis(methylene) dimethanesulfonate (3.41 g, 6.97 mmol) was weighed into a 100 ml round-bottomed flask with a stir bar and septum sealed. The flask was cooled to 0° C. and charged with pyridine (Volume: 25 ml) and acetic anhydride (1.316 ml, 13.95 mmol). The mixture was allowed to come to room temperature over 6 hours. The mixture was cooled to 0° C. and MeOH (1 mL) was added and allowed to stir for 15 minutes. The mixture was concentrated to dryness and re-dissolved in EtOAc (100 mL). The organic phase was washed with aqueous 1% HCl (50 mL), saturated sodium bicarbonate (50 mL) and brine (50 mL). The organic phase was dried over Na$_2$SO$_4$, filtered and concentrated.

The resultant oil was re-dissolved with acetic acid (9.98 ml, 174 mmol) and acetic anhydride (2.63 ml, 27.9 mmol) in a 100 mL round-bottomed flask. H$_2$SO$_4$ (0.037 ml, 0.697 mmol) was added, the flask septum sealed and the mixture was allowed to stir overnight. The mixture was diluted with water (100 mL) and extracted with EtOAc (3×75 mL). The organic phases were combined and washed carefully with saturated sodium bicarbonate (2×100 mL) and brine (1×100 mL). The organic phase was dried over Na$_2$SO$_4$, filtered and concentrated to give 3.15 g of crude ((2S,3R,4S)-2-acetoxy-4-((4-chlorobenzyl)oxy)-5,5-bis(((methylsulfonyl)oxy)methyl)tetrahydrofuran-3-yl)methyl acetate (3.15 g, 5.64 mmol, 81% yield) as a pale yellow oil that was used without further purification.

ESI-MS: 617 (M+Acetate)$^-$ ((3R,4S)-4-((4-chlorobenzyl)oxy)-2-(thymidin-yl)-5,5-bis(((methylsulfonyl)oxy)methyl)tetrahydrofuran-3-yl)methyl acetate (17)

N,O-Bis(trimethylsilyl)acetamide (4.07 ml, 16.64 mmol) was added to a mixture of ((3R,4S)-2-acetoxy-4-((4-chlorobenzyl)oxy)-5,5-bis(((methylsulfonyl)oxy)methyl)tetrahydrofuran-3-yl)methyl acetate (3.10 g, 5.55 mmol) and thymine (0.874 g, 6.93 mmol) in anhydrous acetonitrile (20 ml). The reaction mixture was refluxed for 1 hour to get a clear solution. The solution was cooled to 40° C. and TMS-OTf (1.303 ml, 7.21 mmol) was added. The mixture was heated at 60° C. for 4 hours. The solution was cooled to room temperature, diluted with CH$_2$Cl$_2$ (100 mL), and washed with saturated NaHCO$_3$ (2×100 mL) and brine (1×100 mL). The organic layer was dried (Na$_2$SO$_4$), concentrated under reduced pressure, and the residue was purified by silica gel column chromatography on a standard Biotage Isolera gradient (0-10% v/v MeOH/CH$_2$Cl$_2$) to give ((3R,4S)-4-((4-chlorobenzyl)oxy)-2-(thymidin-yl)-5,5-bis (((methylsulfonyl)oxy)methyl)tetrahydrofuran-3-yl)methyl acetate (2.84 g, 4.54 mmol, 82% yield) as a white solid material.
ESI-MS: 624 (M)$^-$ ((3S,4R)-3-((4-chlorobenzyl)oxy)-4-(hydroxymethyl)-5-(thymidin-yl)tetrahydrofuran-2,2-diyl)bis (methylene) dimethanesulfonate (19)

In a 100 mL round-bottomed flask fitted with a stir bar, ((3R,4S)-4-((4-chlorobenzyl)oxy)-2-(thymidin-yl)-5,5-bis (((methylsulfonyl)oxy)methyl)tetrahydrofuran-3-yl)methyl acetate (2.84 g, 4.54 mmol), was dissolved in Methanol (Volume: 20 ml). Sodium methoxide (0.123 g, 2.272 mmol) was added and the flask was covered and allowed to stir overnight at room temperature. TLC (100% EtOAc) revealed that the reaction was complete. The reaction mixture was evaporated to dryness in vacuo, and applied directly to a 3 g Biotage Samplet, which was fitted to a 25 g Biotage SNAP column. The product was eluted with a 40-100% EtOAc/Hex gradient to give ((3S,4R)-3-((4-chlorobenzyl) oxy)-4-(hydroxymethyl)-5-(thymidin-yl)tetrahydrofuran-2, 2-diyl)bis(methylene) dimethanesulfonate (2.32 g, 3.98 mmol, 88% yield) as a white foam.
ESI-MS: 582 (M)$^-$ ((3S,4R)-5-(thymidin-yl)-3-((4-chlorobenzyl)oxy)-4-(hydroxymethyl)tetrahydrofuran-2,2-diyl)bis(methylene) dimethanesulfonate (20)

To a mixture of ((3S,4R)-3-((4-chlorobenzyl)oxy)-4-(hydroxymethyl)-5-(thymidin-yl)tetrahydrofuran-2,2-diyl)bis (methylene) dimethanesulfonate (1.0 g, 1.715 mmol) and pyridine (10 ml) was added TMS-Cl (0.219 ml, 1.715 mmol) at room temperature. After stirring for 1 hour, the reaction mixture was cooled to 0° C., and benzoyl chloride (0.199 ml, 1.715 mmol) was added dropwise by syringe. The ice-bath was then removed and the reaction mixture stirred at room temperature for 48 hours. The reaction was quenched by the addition of water (2 mL); after stirring for 15 minutes at room temperature, the mixture was diluted with EtOAc (50 mL) and washed with aqueous 5% HCl (2×25 mL), saturated NaHCO$_3$ (1×25 mL) and brine (1×25 mL). The organic phase was dried over Na$_2$SO$_4$, filtered and concentrated to dryness in vacuo. The residue was applied to a 3 g Biotage Samplet with minimal DCM, which was then fitted to a 25 g Biotage SNAP column. The desired product was eluted with 40-100% EtOAc/Hex gradient to give ((3S,4R)-5-(3-benzoyl-5-methyl-2,4-dioxo-3,4-dihydropyrimidin-1(2H)-yl)-3-((4-chlorobenzyl)oxy)-4-(hydroxymethyl)tetrahydrofuran-2,2-diyl)bis(methylene) dimethanesulfonate (0.87 g, 1.266 mmol, 73.8% yield) as a white foam.
N-Benzoyl protection of thymidine results in a diastereomeric mixture which gives rise to two C-5 methyl singlets and two C-6 proton singlets in a 3:2 ratio. For the α-anomer:
$^1$H NMR (400 MHz, Chloroform-d) δ 7.89 (s, 1H, diastereomer 1), 7.87 (d, J=1.3 Hz, 1H, diastereomer 2), 7.67-7.60 (m, 1H), 7.60-7.39 (m, 3H), 7.39-7.17 (m, 5H), 6.02 (d, J=8.6 Hz, 1H), 4.67-4.46 (m, 3H), 4.42-4.26 (m, 5H), 3.87-3.73 (m, 2H), 3.02 (s, 3H), 2.98 (s, 2H), 2.82 (p, J=6.5 Hz, 1H), 2.03 (s, 3H, diastereomer 1), 1.94 (s, 3H, diasteromer 2).

((3S,4R,5R)-4-(((tert-butoxy-(2,2,2-trifluoroethoxy) dicarbonyl)amino)methyl)-3-((4-chlorobenzyl)oxy)-5-(3-benzoyl-thymidin-yl)tetrahydrofuran-2,2-diyl) bis(methylene) dimethanesulfonate (21)

In a 20 mL scintillation vial fitted with a stir bar was weighed ((3S,4R)-5-(3-benzoyl-thymidin-yl)-3-((4-chlorobenzyl)oxy)-4-(hydroxymethyl)tetrahydrofuran-2,2-diyl) bis(methylene) dimethanesulfonate (0.25 g, 0.364 mmol), (2,2,2-trifluoroethyl)-tert-Butyl-iminodicarbonate (0.088 g, 0.364 mmol), and triphenylphosphine (0.095 g, 0.364 mmol). The vial was charged with THF (Volume: 4 ml) and DIAD, 1.0M Solution in THF (0.364 ml, 0.364 mmol) was added dropwise. After stirring overnight, the reaction mixture was concentrated to dryness in vacuo and applied to a 25 g Biotage SNAP column. Product was eluted with 40-100% EtOAc/Hexanes gradient to give ((3S,4R,5R)-4-(((tert-butoxy-(2,2,2-trifluoroethoxy)dicarbonyl)amino) methyl)-3-((4-chlorobenzyl)oxy)-5-(3-benzoyl-thymidin-yl)tetrahydrofuran-2,2-diyl)bis(methylene) dimethanesulfonate (0.228 g, 0.25 mmol, 68.7% yield) as a white foam.
1H NMR (400 MHz, Chloroform-d) δ 7.94 (d, J=7.6 Hz, 2H), 7.63 (t, J=7.4 Hz, 1H), 7.47 (t, J=7.8 Hz, 2H), 7.34 (d, J=8.4 Hz, 2H), 7.28 (d, J=8.4 Hz, 2H), 7.15 (s, 1H), 5.99 (d, J=9.2 Hz, 1H), 4.70 (d, J=11.0 Hz, 1H), 4.60 (d, J=10.9 Hz, 1H), 4.49 (qd, J=8.3, 3.4 Hz, 2H), 4.41-4.24 (m, 6H), 3.94 (d, J=5.6 Hz, 2H), 3.20-3.05 (m, 1H), 2.98 (s, 2H), 2.97 (s, 4H), 1.92 (s, 3H), 1.46 (s, 9H). ESI-MS: 971 (M+Acetate)$^-$ ((3S,4R,5R)-4-(((tert-butoxycarbonyl)amino) methyl)-3-((4-chlorobenzyl)oxy)-5-(thymidin-yl) tetrahydrofuran-2,2-diyl)bis(methylene) dimethanesulfonate (22)

In a 20 mL screw cap scintillation vial was((3S,4R,5R)-4-(((tert-butoxy-(2,2,2-trifluoroethoxy)dicarbonyl)amino) methyl)-3-((4-chlorobenzyl)oxy)-5-(3-benzoyl-thymidin-yl)tetrahydrofuran-2,2-diyl)bis(methylene) dimethanesulfonate (125 mg, 0.137 mmol) weighed with a magnetic stir bar. The vial was charged with THF (Volume: 1.5 ml) and 2.0M LiOH in water (1.507 ml, 3.01 mmol), covered and allowed to stir overnight at room temperature The reaction mixture was diluted with EtOAc (7 mL) and washed with saturated sodium bicarbonate (1×5 mL) and brine (1×5 mL). The organic phase was dried over Na$_2$SO$_4$, filtered and concentrated in vacuo to give ((3S,4R,5R)-4-(((tert-butoxycarbonyl)amino)methyl)-3-((4-chlorobenzyl) oxy)-5-(thymidin-yl)tetrahydrofuran-2,2-diyl)bis(methylene) dimethanesulfonate (80 mg, 0.117 mmol, 86% yield) as an off white foam that was sufficiently pure to be used crude for subsequent reactions.
1H NMR (400 MHz, Chloroform-d) δ 8.61 (s, 1H), 7.36 (d, J=8.4 Hz, 2H), 7.27 (d, J=8.4 Hz, 2H), 7.13 (s, 1H), 6.04 (d, J=9.3 Hz, 1H), 4.74-4.64 (m, 1H), 4.59 (d, J=11.3 Hz, 1H), 4.50 (d, J=11.3 Hz, 1H), 4.40-4.23 (m, 6H), 4.00-3.89 (m, 1H), 3.44 (dd, J=13.6, 6.7 Hz, 1H), 3.17 (ddd, J=14.3, 8.4, 5.8 Hz, 1H), 3.09 (s, 3H), 3.00 (s, 3H), 1.89 (s, 3H), 1.32 (s, 9H). ESI-MS: 681 (M)$^-$ (1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (23)

In a 10 mL conical reaction vial was ((3S,4R,5R)-4-(((tert-butoxycarbonyl)amino)methyl)-3-((4-chlorobenzyl) oxy)-5-(thymidin-yl)tetrahydrofuran-2,2-diyl)bis(methylene) dimethanesulfonate (60 mg, 0.076 mmol) dissolved in Tetrahydrofuran (7 ml). Sodium hydride, 60% Suspension in oil (12.21 mg, 0.305 mmol) was added to the vial at once, the vial was fitted with a stir bar and a teflon-lined septum screw-cap and the mixture was stirred at 55° C. overnight. The reaction was cooled to room temperature and quenched with a few drops of MeOH added with stirring. The mixture was diluted with EtOAc (10 mL) and washed with aqueous saturated sodium bicarbonate (2×10 mL) and brine (1×10 mL). The organic phase was dried over Na$_2$SO$_4$, filtered and concentrated to give a tan foam that was dissolved in a minimal amount of DCM and applied to a 1 g Biotage Samplet fitted to a 10 g Biotage SNAP column. Product was eluted with a 0-100% EtOAc/Hexanes gradient to give (1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (35 mg, 0.060 mmol, 78% yield) as a white foam.

The cyclization gave a mixture of N-diastereomers in a 3:2 mixture that was unresolvable by TLC/column chromatography. This presence of the minor diastereomer gave rise to several distinct signals that were denoted by a (*). 1H NMR (400 MHz, Chloroform-d) δ 8.63 (s, 1H), 8.59* (s), 7.62 (s, 1H), 7.58* (s), 7.40-7.27 (m, 2H), 7.23 (d, J=8.1 Hz, 3H), 5.80* (s), 5.79 (s, 1H), 4.66-4.44 (m, 2H), 4.44-4.27 (m, 2H), 4.09-3.92 (m, 2H), 3.79 (d, J=12.8 Hz, 1H), 3.61* (d, J=12.6 Hz), 3.36-3.10 (m, 2H), 3.08 (s, 3H), 2.81* (s), 2.70 (s, 1H), 1.94 (s, 3H), 1.46 (s, 9H), 1.44* (s). ESI-MS: 585 (M)⁻.

1-((1R,5R,7R,8S)-8-((4-chlorobenzyl)oxy)-5-(hydroxymethyl)-6-oxa-3-azabicyclo[3.2.1]octan-7-yl)-thymidine (24)

In a 10 mL glass reaction vial was (1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (35 mg, 0.060 mmol) and sodium benzoate (17.21 mg, 0.119 mmol) dissolved in DMF (2 ml). The vial was fitted with a stir bar and sealed with a teflon lined screw-cap septum. The mixture was heated to 105° C. in an oil bath overnight. All components had effected solution. The vial was removed from the oil bath and 10 uL removed to asses reaction completeness via TLC. White crystals started forming immediately upon cooling. TLC revealed reaction was only 50% complete, so an additional portion of sodium benzoate (17.21 mg, 0.119 mmol) was added along with 1 mL DMF to allow for stirring. The mixture was heated to 105° C. for an additional 48 hours with periodic aliquots removed for TLC analysis. The thick precipitate never fully effected solution, even after heating to 105° C. for two days, however the reaction went to completion with no detectable decomposition.

The reaction mixture was cooled to room temperature, diluted with EtOAc (10 mL) and washed with water (2×10 mL), saturated bicarbonate solution (1×10 mL) and brine (1×10 mL). The organic phase was dried over Na₂SO₄, filtered and concentrated in vacuo. The residue was re-dissolved in MeOH (2 ml) and sodium methoxide (6.45 mg, 0.119 mmol) was added at once. The mixture was allowed to stir overnight. TLC revealed that the reaction was complete and the mixture was concentrated to dryness. The resultant residue was re-dissolved in 1 mL of 1:1 DCM/TFA and stirred for 30 minutes at room temperature. The mixture was concentrated to dryness and applied to a 4 g RediSep Rf silica column using a minimal amount of DCM. The product was eluted with a 0-100% EtOAc/Hex gradient containing 3% TEA. The product fractions were combined and concentrated to dryness. The resultant white powder was re-dissolved in DCM (3 mL) and washed with saturated bicarbonate solution (1×5 mL). The aqueous fraction was back extracted with 70/30 chloroform/isopropanol (2×5 mL). The organic phases were combined, dried over MgSO₄, filtered and concentrated to give 1-((1R,5R,7R,8S)-8-((4-chlorobenzyl)oxy)-5-(hydroxy)-5-(hydroxymethyl)-6-oxa-3-azabicyclo[3.2.1]octan-7-yl)-thymidine (17 mg, 0.042 mmol, 69.8% yield) as a white powder.

¹H NMR (400 MHz, Acetonitrile-d3) δ 8.05 (q, J=1.2 Hz, 1H), 7.36 (s, 4H), 5.94 (s, 1H), 4.52 (dd, J=38.6, 11.9 Hz, 2H), 4.14 (d, J=5.1 Hz, 1H), 3.58 (dd, J=33.9, 12.3 Hz, 2H), 3.09 (d, J=12.7 Hz, 1H), 2.89 (d, J=13.0 Hz, 1H), 2.75 (dd, J=13.0, 3.2 Hz, 1H), 2.57-2.50 (m, 1H), 2.34 (d, J=13.0 Hz, 1H), 1.98-1.90 (m, 2H), 1.81 (d, J=1.1 Hz, 3H). ¹³C NMR (101 MHz, CD₃CN) δ 165.01, 151.22, 138.07, 136.98, 133.72, 130.05, 129.23, 109.19, 87.42, 85.04, 73.06, 71.38, 61.04, 45.85, 43.60, 41.58, 12.71.

(1R,5R,7R,8S)-tert-butyl 8-((4-chlorobenzyl)oxy)-7-(thymidin-yl)-5-(hydroxymethyl)-6-oxa-3-azabicyclo[3.2.1]octane-3-carboxylate (25)

(1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (1.0 g, 1.47 mmol) and sodium benzoate (0.63 g, 4.40 mmol) were weighed into a 100 mL round bottomed flask with a stir-bar. The flask was charged with DMF (10 mL), septum sealed and heated to 100° C. for 40 hours. TLC (65% EtOAc/Hex) indicated that the reaction was complete. The mixture was diluted with saturated sodium bicarbonate (100 mL) and extracted with ethyl acetate (3×50 mL). The organic phases were combined and washed with brine, dried over Na₂SO₄, filtered and concentrated in vacuo to give a tan solid that was dissolved in a mixture of dioxane (20 mL) and 2M NaOH (3 mL). The mixture was warmed to 50° C. overnight. The reaction mixture was concentrated in vacuo to a solid and applied to a 50 g Biotage SNAP silica column and eluted using a gradient of 50-100% EtOAc in hexanes over 7 column volumes and holding at 100% EtOAc for 7 column volumes. The product containing fractions were combined and concentrated in vacuo to yield (1R,5R,7R,8S)-tert-butyl 8-(hydroxy)-7-(thymidin-yl)-5-(hydroxymethyl)-6-oxa-3-azabicyclo[3.2.1]octane-3-carboxylate (0.63 g, 1.24 mmol, 84.6%) as a white foam.

ESI-MS: 506 (M)⁻

(1R,5R,7R,8S)-8-Hydroxy-7-(thymidin-yl)-5-(hydroxymethyl)-3-(2,2,2-trifluoroacetyl)-6-oxa-3-azabicyclo[3.2.1]octane (26)

(1R,5R,7R,8S)-tert-butyl 8-(hydroxy)-7-(thymidin-yl)-5-(hydroxymethyl)-6-oxa-3-azabicyclo[3.2.1]octane-3-carboxylate (0.6 g, 1.18 mmol) was dissolved in ethanol (25 mL) and transferred to a 500 mL Parr hydrogenation vessel. Pearlman's Catalyst (0.35 g) and a single drop of glacial acetic acid was added at once and the mixture was shaken on a Parr hydrogenator under a hydrogen atmosphere (40 psi) for 4 hours. TLC indicated that the reaction was complete and spot-to-spot (5% methanol in DCM). The mixture was carefully filtered through a bed of celite that was previously washed with several volumes of methanol. The celite bed was washed with ethyl acetate (100 mL) and ethanol (100 mL). The filtrate was concentrated in vacuo to approximately 5 mL and transferred to a 20 mL glass scintillation vial. The material was taken to dryness in vacuo to give tert-butyl (1R,5R,7R,8S)-8-hydroxy-5-(hydroxymethyl)-7-(5-methyl-2,4-dioxo-3,4-dihydropyrimidin-1(2H)-yl)-6-oxa-3-azabicyclo[3.2.1]octane-3-carboxylate (54) as an off white powder that was used without further purification.

The glass scintillation vial was fitted with a micro stir bar and charged with dichloromethane (2 mL) and trifluoroacetic acid (2 mL). The vial was sealed and set to stir for 30 minutes. The micro stir bar was removed and the volatiles removed in vacuo. The resultant oil was co-evaporated with toluene (2×4 mL), methanol (1×4 mL) and DCM (2×4 mL) to give an off white powder/residue in the vial. The residue was re-dissolved in methanol (5 mL) with a micro stir bar in the scintillation vial. Ethyl trifluoroacetate (2.00 mL, 16.9 mmol) and TEA (0.410 mL, 3.54 mmol) were added, the vial was sealed and the mixture set to stir overnight. After 20 hours, TLC of the mixture showed that the starting material was completely consumed and a new product had been formed. The volatiles were removed in vacuo. The residue was co-evaporated with EtOAc (2×5 mL) and toluene (2×5 mL) to give (1R,5R,7R,8S)-8-Hydroxy-7-(thymidin-yl)-5-(hydroxymethyl)-3-(2,2,2-trifluoroacetyl)-6-oxa-3-azabicyclo[3.2.1]octane (0.30 g, 79.8%) for use directly in the next tritylation step. $^1$H NMR analysis of the crude material indicated that a mixture of diastereomers in an approximately 55:45 ratio were formed (by integration of anomeric signals).

(1R,5R,7R,8S)-8-Hydroxy-7-(thymidin-yl)-5-((4,4'-dimethoxytrityloxy)methyl)-3-(2,2,2-trifluoroacetyl)-6-oxa-3-azabicyclo[3.2.1]octane (27)

5'-O-DMTr-aCBBN(tfa)

In a 50 mL round bottomed flask, (1R,5R,7R,8S)-8-Hydroxy-7-(thymidin-yl)-5-(hydroxymethyl)-3-(2,2,2-trifluoroacetyl)-6-oxa-3-azabicyclo[3.2.1]octane (0.28 g, 0.74 mmol) was co-evaporated with pyridine (2×10 mL). The flask was charged with anhydrous pyridine (7 mL) and DMTr-Cl was added, at once, the solution. The flask was sealed and the mixture stirred overnight at room temperature. TLC revealed that all starting material was consumed (95% EtOAc/Hex or 5% MeOH/DCM). The reaction was quenched by addition of methanol (0.5 mL) and stirring continued for 30 minutes, followed by addition of aqueous saturated NaHCO3 (30 mL). The aqueous phase was extracted with EtOAc (3×20 mL). The organic phases were combined and washed with brine (1×20 mL), dried over Na$_2$SO$_4$, filtered and concentrated in vacuo to give a tan foam. The solids were dissolved in a minimum amount of DCM and applied to a 50 g Biotage silica SNAP column previously treated with 60 mL of a 25% solution of TEA in hexanes and equilibrated with 200 mL of 30% EtOAc/Hex. The product was eluted off the column with a gradient of 30-100% EtOAc in Hexanes over 10 column volumes followed by 4 column volumes of 100% EtOAc. Fractions containing pure product were combined and concentrated to give DMTr-(N-tfa)-aminoCBBN as a white foam. Both $^1$H and $^{19}$F NMR indicates two distinct diastereomers. Asterisks in the $^1$H NMR tabulation denotes peaks where diastereomeric protons were resolved in an approximately 55:45 ratio.

$^1$H NMR (400 MHz, Chloroform-d) δ 7.72* (d, J=1.0 Hz, 1H), 7.68* (d, J=1.1 Hz, 1H), 7.49-7.38 (m, 4H), 7.35-7.20 (m, 14H), 6.93-6.78 (m, 8H), 5.73* (s, 1H), 5.68* (s, 1H), 4.55-4.36 (m, 3H), 4.05* (s, 2H), 4.01* (s, 2H), 3.94-3.84 (m, 1H), 3.79 (q, J=0.7 Hz, 13H), 3.64 (t, J=12.0 Hz, 1H), 3.57-3.38 (m, 4H), 3.38-3.15 (m, 4H), 2.70* (d, J=3.6 Hz, 1H), 2.65* (t, J=4.0 Hz, 1H), 1.47* (s, 3H), 1.41* (s, 3H), 1.28 (bs, 2H). $^{19}$F NMR (376 MHz, cdcl$_3$) δ −68.61, −68.90.
ESI MS: 680 (M)$^-$ (1R,5R,7R,8S)-7-(thymidin-yl)-5-((4,4'-dimethoxytrityloxy)methyl)-3-(2,2,2-trifluoroacetyl)-6,8-oxa-3-azabicyclo[3.2.1]octane-8-O-(2-cyanoethyl)-N,N-diisopropylphosphoramidite (28)

5'-O-DMTr-aCBBN(tfa) Amidite

5'-O-DMTr-aCBBN(tfa) (0.32 g, 0.47 mmol) was weighed in a 100 mL round-bottomed flask fitted with a stir bar. The flask was charged with dichloromethane (7 mL) and set to stir. 2-Cyanoethyl N,N,N',N'-tetraisopropylphosphordiamidite (0.283 g, 0.94 mmol) was weighed in a syringe and added at once to the solution followed by 4,5-dicyanoimidazole (55.44 mg, 0.47 mmol). The flask was immediately septum sealed and allowed to stir overnight. In process TLC at 20 hours revealed that there was only a trace of starting material, with two new spots arising that were trityl positive and appeared to char similarly to starting nucleoside when treated with Hanessian's stain following development with 5% methanol/DCM w/ UV visualization. Reaction was quenched by the addition of aqueous saturated NaHCO3 solution (50 mL). The aqueous phase was extracted with ethyl acetate (4×20 mL). The organic phases were combined and extracted with aqueous saturated NaHCO$_3$ solution (2×50 mL) and brine (1×20 mL). The organic phase was dried over Na$_2$SO$_4$, filtered and concentrated to give a colorless oil. The crude product was dissolved in a minimum amount of DCM and applied to a 50 g Biotage silica SNAP column previously treated with 60 mL of a 25% solution of TEA in hexanes and equilibrated with 150 mL of 30% ethyl acetate/hexanes. The product was eluted off the column with a gradient of 30-100% EtOAc in Hexanes over 10 column volumes followed by 4 column volumes of 100% EtOAc. Fractions containing pure product were combined and concentrated to give DMTr-(N-tfa)-aminoCBBN amidite as a white foam. $^{31}$P and $^1$H NMR indicate the presence of four distinct products, as expected, each corresponding to a separate stereoisomer arising from the tfa protection of the cyclic amine and the phosphitylation reaction.

$^{31}$P NMR (162 MHz, CD$_3$CN) δ 150.03, 149.97, 147.46. Relative intensity of 1:1:2.
$^{19}$F NMR (376 MHz, CD$_3$CN) δ −69.30, −69.31, −69.47, −69.47.
ESI MS: 904.8 (M+Na$^+$)$^+$ Example 2: Production of 2'-C-Bridged Bicyclic Nucleosides This example describes the synthesis of key intermediates for the production of 2'-C-Bridged Bicyclic Nucleosides with different nucleobases (see FIGS. 2A-2C).

Figure 2A:
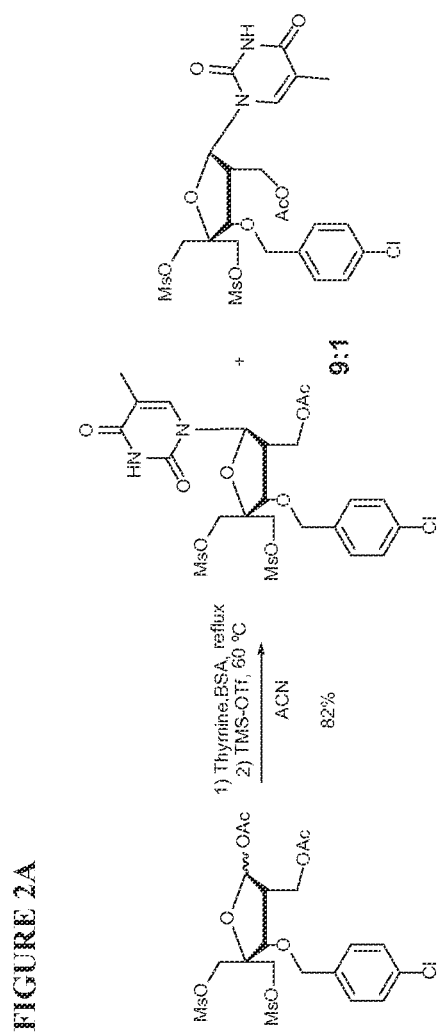
FIGS. 2A-2C provide exemplary production of 2'-C-Bridged Bicyclic Nucleosides with different nucleobases.
Figure 2B:
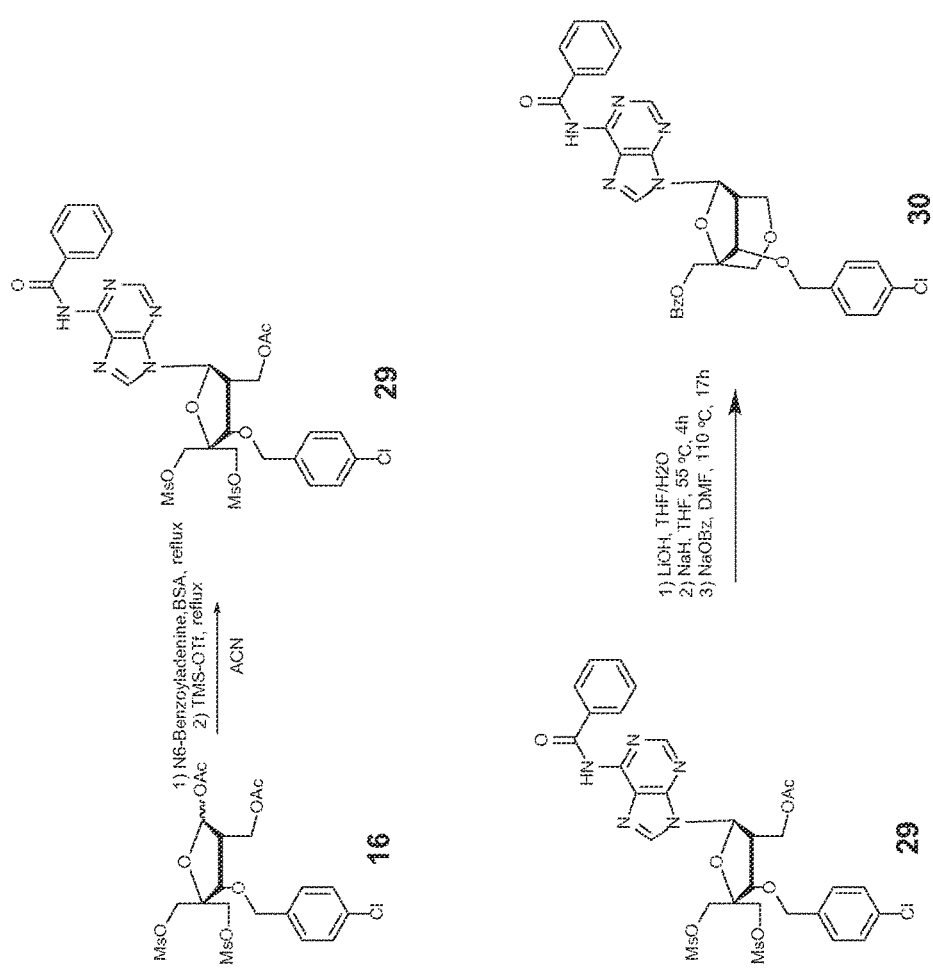
Figure 2C:
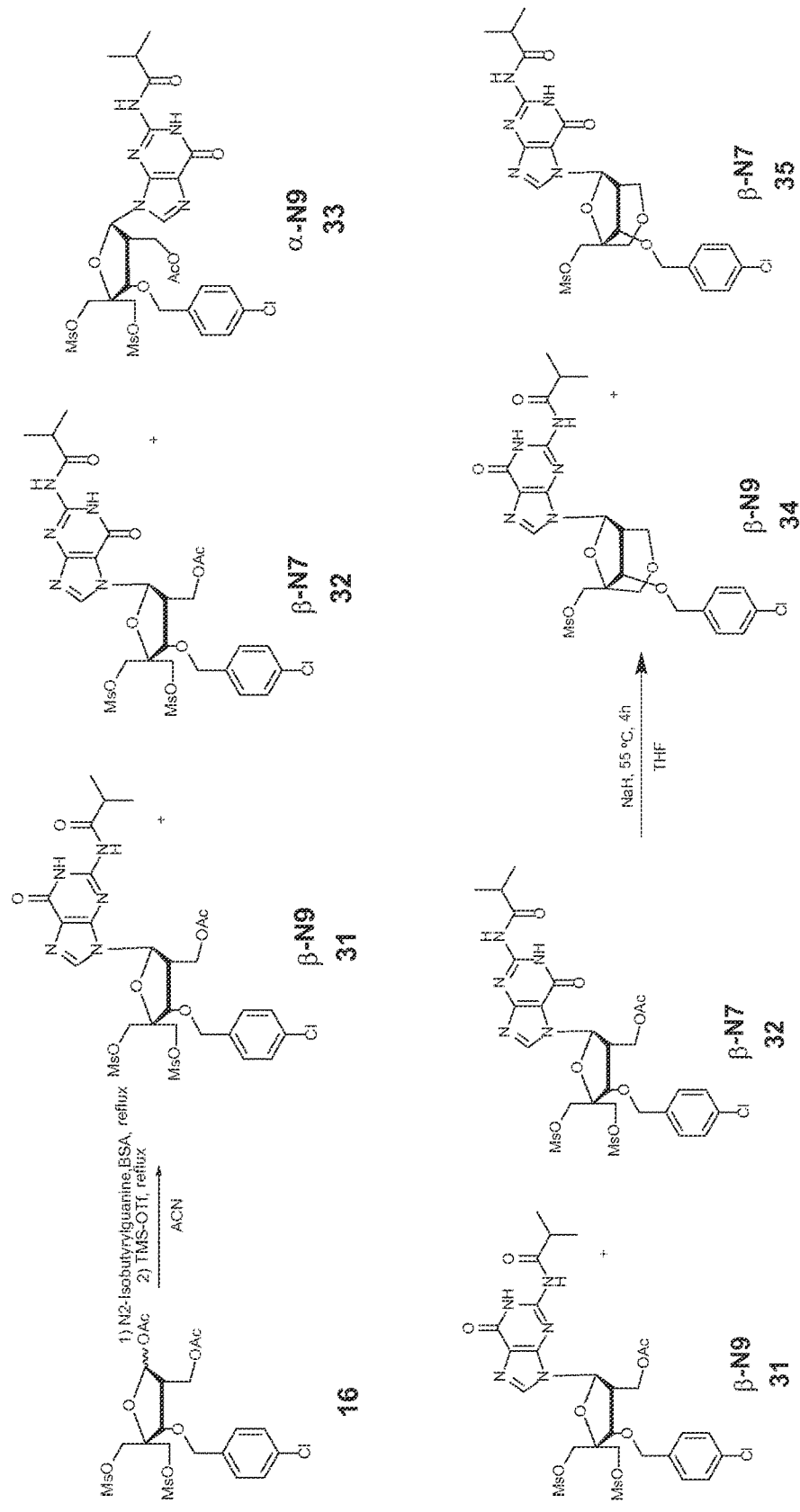

((3R,4S)-4-((4-chlorobenzyl)oxy)-2-(thymidin-yl)-5,5-bis(((methylsulfonyl)oxy)methyl)tetrahydrofuran-3-yl)methyl acetate (FIG. 2A)

N,O-Bis(trimethylsilyl)acetamide (4.07 ml, 16.64 mmol) was added to a mixture of ((3R,4S)-2-acetoxy-4-((4-chlorobenzyl)oxy)-5,5-bis(((methylsulfonyl)oxy)methyl)tetrahydrofuran-3-yl)methyl acetate (3.10 g, 5.55 mmol) and thymine (0.874 g, 6.93 mmol) in anhydrous acetonitrile (20 ml). The reaction mixture was refluxed for 1 hour to get a clear solution. The solution was cooled to 40° C. and TMS-OTf (1.303 ml, 7.21 mmol) was added. The mixture was heated at 60° C. for 4 hours. The solution was cooled to room temperature, diluted with CH$_2$Cl$_2$ (100 mL), and washed with saturated NaHCO$_3$ (2×100 mL) and brine (1×100 mL). The organic layer was dried (Na$_2$SO$_4$), concentrated under reduced pressure, and the residue was purified by silica gel column chromatography on a standard Biotage Isolera gradient (0-10% v/v MeOH/CH$_2$Cl$_2$) to give ((3R,4S)-4-((4-chlorobenzyl)oxy)-2-(thymidin-yl)-5,5-bis(((methylsulfonyl)oxy)methyl)tetrahydrofuran-3-yl)methyl acetate (2.84 g, 4.54 mmol, 82% yield) as a white solid material.

ESI-MS: 624 (M)$^-$
NMR of the crude material revealed a major and minor anomeric signal with a relative integration of 0.10:1.00
$^1$H NMR of anomeric peaks (300 MHz, Chloroform-d) δ 6.54 (d, J=8.1 Hz, minor), 6.04 (d, J=9.2 Hz, major)

((3R,4S)-4-((4-chlorobenzyl)oxy)-2-(6-N-Benzoyladenosin-yl)-5,5-bis(((methylsulfonyl)oxy)methyl) tetrahydrofuran-3-yl)methyl acetate (29)

N,O-Bis(trimethylsilyl)acetamide (1.09 g, 1.31 ml, 5.37 mmol) was added to a mixture of ((3R,4S)-2-acetoxy-4-((4-chlorobenzyl)oxy)-5,5-bis(((methylsulfonyl)oxy)methyl) tetrahydrofuran-3-yl)methyl acetate (1.00 g, 1.79 mmol) and N[6]-benzoyladenine (0.640 g, 2.68 mmol) in anhydrous acetonitrile (15 ml). The reaction mixture was refluxed for 1 hour. The solution was cooled to 40° C. and TMS-OTf (0.60 g, 0.49 ml, 2.68 mmol) was added. The mixture was refluxed for 4 hours. The solution was cooled to room temperature, diluted with $CH_2Cl_2$ (100 mL), and washed with saturated $NaHCO_3$ (2×100 mL) and brine (1×100 mL). The organic layer was dried ($Na_2SO_4$), concentrated under reduced pressure, and the residue was purified by silica gel column chromatography on a standard Biotage Isolera gradient (0-10% v/v $MeOH/CH_2Cl_2$) to give ((3R,4S)-4-((4-chlorobenzyl)oxy)-2-(6-N-Benzoyladenosin-yl)-5,5-bis(((methylsulfonyl)oxy)methyl)tetrahydrofuran-3-yl)methyl acetate (0.95 g, 1.28 mmol, 72% yield) as a white solid material. There were not any appreciable amounts of isolable nucleoside side products.

{(1R,5R,7R,8S)-7-[(9R)-9a-Benzoyl-9-adenineyl]-8-(4-Chlorobenzyloxy)-3.6-dioxabicyclo[3.2.1]oct-5-yl}methyl benzoate (30)

((3R,4S)-4-((4-chlorobenzyl)oxy)-2-(6-N-Benzoyladenosin-yl)-5,5-bis(((methylsulfonyl)oxy)methyl)tetrahydrofuran-3-yl)methyl acetate (0.70 g, mmol) was weighed into a 20 mL glass scintillation vial with a micro stir bar. The vial was charged with THF (5 mL) and an aqueous LiOH solution (0.47 mL, 1.0M). The mixture was then allowed to stir 2 h at room temperature. TLC indicated that deacetylation had occurred while leaving the N-Benzoyl group intact. The reaction was diluted with water (7 mL) and extracted with ethyl acetate (3×5 mL). The organic phases were combined, washed with brine (1×5 mL), dried over $Na_2SO_4$, filtered and concentrated in vacuo to give a white foam that was used crude.

The solids were transferred to a 10 mL conical reaction vial fitted with a stir bar and dissolved in anhydrous THF (5 mL). Sodium hydride was added to the vial at once. The vial was septum sealed and set to stir at 55° C. for 4 h. TLC indicated the reaction was complete. The reaction was quenched by careful addition of sodium bicarbonate solution to the cooled reaction mixture (3 mL). The mixture was further diluted to 10 mL with water and extracted with ethyl acetate (3×5 mL). The organic phases were combined, washed with brine (1×5 mL), dried over $Na_2SO_4$, filtered and concentrated in vacuo to give an off white/tan foam that was used crude.

The crude solids were transferred to a 20 mL scintillation vial fitted with a stir bar. Sodium benzoate was added to the vial which was then charged with DMF (5 mL). The vial was sealed and heated to 110° C. in an oil bath with continuous stirring. After 30 minutes, the mixture became a thick slurry. The mixture was allowed to continue stirring overnight. TLC indicates the reaction was complete. Upon cooling the mixture became a thick gel which was partitioned with saturated sodium bicarbonate solution (30 mL) and ethyl acetate (10 mL). The aqueous phase was extracted with ethyl acetate (2×10 mL). The organic phases were combined, washed with brine (1×5 mL), dried over $Na_2SO_4$, filtered and concentrated in vacuo to give an off white/tan foam that was further purified via silica gel column chromatography (EtOAc/Hexanes gradient 30%-100%) to give {(1R,5R,7R,8S)-7-[(9R)-9a-Benzoyl-9-adenineyl]-8-(4-Chlorobenzyloxy)-3.6-dioxabicyclo[3.2.1]oct-5-yl}methyl benzoate (0.48 g, 0.77 mmol, 80.5%).

((3R,4S)-4-((4-chlorobenzyl)oxy)-2-(6-N-isobutyrylguanosin-yl)-5,5-bis(((methylsulfonyl)oxy)methyl) tetrahydrofuran-3-yl)methyl acetate (31)

N,O-Bis(trimethylsilyl)acetamide (1.09 g, 1.31 ml, 5.37 mmol) was added to a mixture of ((3R,4S)-2-acetoxy-4-((4-chlorobenzyl)oxy)-5,5-bis(((methylsulfonyl)oxy)methyl) tetrahydrofuran-3-yl)methyl acetate (1.00 g, 1.79 mmol) and N[2]-isobutyrylguanine (0.59 g, 2.68 mmol) in anhydrous acetonitrile (15 ml). The reaction mixture was refluxed for 1 hour. The solution was cooled to 40° C. and TMS-OTf (0.60 g, 0.49 ml, 2.68 mmol) was added. The mixture was refluxed for 4 hours. The solution was cooled to room temperature, diluted with $CH_2Cl_2$ (100 mL), and washed with saturated $NaHCO_3$ (2×100 mL) and brine (1×100 mL). The organic layer was dried ($Na_2SO_4$), concentrated under reduced pressure, and the residue was purified by silica gel column chromatography on a standard Biotage Isolera gradient (0-10% v/v $MeOH/CH_2Cl_2$) to give the β-9-N-guanosinyl anomer (0.67 g, 0.93 mmol, 52% yield) as a white solid material and the β-7-N guanosinyl anomer (0.17 g, 0.23 mmol, 13.2%).

NMR analysis of the crude glycosylation revealed 1 major and 2 minor anomeric peaks in a 75:17:8 ratio; associated with β-N9, β-N7 and α-N9 anomers respectively $^1$H NMR of anomeric peaks (300 MHz, Chloroform-d) δ 6.30 (d, J=7.7 Hz) minor 8%, 6.14 (d, J=9.1 Hz) minor 17%, 5.98 (d, J=8.8 Hz) major 75%.

1-[(9S)-9-{(1R,7R,8S)-8-(4-Chlorobenzyloxy)-5-[(methylsulfonyloxy)methyl]-3.6-dioxabicyclo[3.2.1]oct-7-yl}-6-oxo-1,9-dihydropurin-2-ylamino]-2-methyl-1-propanone (34) (34)

25 mg of crude glycosylation product with an 82:18 ratio of compound 31:32 was weighed in a 4 mL glass vial with a stir bar. The vial was charged with THF (1 mL) and 60% NaH dispersion (4.5 mgs) was added. The vial was sealed and heated to 55° C. oil bath with stirring for 4 hr. Rxn was monitored via TLC until reaction was complete. The mixture was quenched by addition of a few drops of water to the crude reaction mixture. The mixture was transferred to a 20 mL scintillation vial with water (~7 mL) and ethyl acetate (approximately 7 mL). The aqueous phase was further extracted with ethyl acetate (2×5 mL). The organics were combined, washed with brine (1×5 mL), dried over $Na_2SO_4$, filtered and concentrated in vacuo to give the crude cyclization mixture as a tan foam (12 mg). The mixture was dissolved in $CDCl_3$ and submitted to $^1$H NMR that confirmed the main impurity was the N7-anomer due to both the major and minor anomeric peak turning to singlets in an 82:18 ratio. The ibu-methyl peaks also remained, confirming that the cyclization reaction is compatible with the (ibu)G-Glycosylated molecule.

Example 3: Synthesis of Oligonucleotides Bearing 2'-C-Bridged Bicyclic Nucleotides General Synthesis Methodology Short strands of oligonucleotides bearing sugar and base modifications can be prepared once the modified nucleoside is synthesized and the free 5' and 3'-hydroxyl groups are masked with appropriate reactive groups to become a nucleotide monomer. For example, automated solid phase synthesis using phosphoramidite chemistry may be used (see McBride et al., *Tetrahedron Letters* 24:245-248 (1983) and Sinha et al., *Tetrahedron Letters* 24:5843-5846 (1983)).

Phosphoramidite chemistry, together with related methods such as hydrogen phosphonate chemistry, has been extensively reviewed with respect to their uses in oligonucleotide chemistry (see, for example, Beaucage et al., *Tetrahedron* 48:2223-2311(1992)). During solid phase oligonucleotide synthesis, a series of nucleotide monomers are sequentially attached, via their phosphoramidite derivatives, in a predetermined order to either, depending on the direction of chain extension, the 5'-functional group or the 3'-functional group of the growing oligonucleotide strand.

The oligonucleotide strand is anchored to an insoluble moiety such as controlled pore glass or polystyrene resin beads. The method of attachment of each monomer is generally comprised of the following steps 1 through 5. Step 1 involves the protection of the reactive functionality. The common reactive functionality is the 5'-hydroxyl group of the terminal nucleoside. This functionality is usually protected with a 4,4'-dimethoxytrityl (DMT) moiety that can be removed via acid treatment. One of the features of the DMT moiety is that it forms a bright orange DMT cation during acid deprotection. This cation effectively serves as reporter group that can be monitored at a wavelength between 480 and 500 nm for the purpose of judging the completeness of the previous coupling step. Most commercially available automated synthesizers have the capability to monitor the released DMT cation. This data gives the operator an instant indication of whether or not the synthesis failed at any given step. Step 2 involves the coupling by addition of a phosphoramidite derivative and an activator. The phosphoramidite derivative is usually a nucleoside phosphoramidite. However, it may also be a phosphoramidite derivatized with a different organic moiety. Step 3 involves the capping of unreacted terminal functional groups. This step introduces an inert protective group that prevents further coupling to failure sequences. Step 4 involves oxidation of the newly formed phosphorous nucleotide backbone linkage from the trivalent phosphite to the stable pentavalent state. This oxidation step can be performed with either an oxygen-based oxidant that results in a phosphate nucleotide or a sulfurizing oxidant that results in a phosphorothioate nucleotide. Step 5 involves a repetition of the process after a washing step.

Truncated, 16 nucleotide sequence complementary to a nucleotide sequence of human miR-208a was synthesized in 1 µmol scale on a MerMade-12 automated oligonucleotide synthesis system (Bioautomation, Plano, Tex., USA). The synthesizer was operated using standard detritylation, activator and capping solutions, known to those skilled in the art. Oligonucleotide chain elongation was affected using single couplings of 420 seconds for each deoxynucleotide amidite, double couplings lasting a total of 900 seconds for LNA amidites and triple couplings lasting a total of 1800 seconds for novel nucleoside amidites, such as the DMTr-aCBBN(tfa) amidite. Oxidation with either 0.025 M Iodine solution or 0.2 M PADS oxidation solution after each coupling cycle is performed to generate either phosphodiester or phosphorothioate internucleotide linkages, respectively. The unmodified anti-208a DNA sequence incorporates nine 2'-deoxythymidine residues which were selectively replaced with thymidine LNA (lT), thymidine oxoCBBN (bT), cytidine oxoCBBN (bC) or thymidine aminoCBBN (abT) nucleotides. Thymidine LNA amidite was purchased from commercial sources and matches reported spectroscopic data (see Singh, S. K.; Nielsen, P.; Koshkin, A. A.; Wengel, J. Chem.Commun. 1998, 455-6). The Thymidyl-2'-C,4'-C-Bridged Bicyclonucleoside (thymidine oxoCBBN, bT) and cytidyl-2'-C,4'-C-Bridged Bicyclonucleoside (cytidine oxoCBBN, bC) was synthesized according to a literature procedure and all spectroscopic data matched reported values (see U.S. Pat. No. 6,403,566, Wang, G., Girardet, J., Gunic, E. Tetrahedron 55, 1999, 7707-7724). The balance of the nucleotides was comprised of 2'-deoxynucleotides or LNA nucleotides with bases corresponding to the natural anti-208a RNA sequence. Phosphorothioate internucleotide linkages are denoted with an "s" following the base (e.g., abTs or dGs), while no letter following a base indicates a phosphodiester internucleotide linkage (e.g., abT or dG)

Preparation of Compound M-11915 (SEQ ID NO: 1): dC.dT.dT.dT.dT.dT.dG.dC.abT. dC.dG.dT.dC.dT.dT.dA Phosphoramidite Reagent (28) was used in the synthesis of a singly modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as described previously. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4845.2, found 4844.0 (M)⁻.

Preparation of Compound M-11916 (SEQ ID NO:2): dC.dT.dT.dT.dT.abT.dG.dC.abT. dC.dG.dT.dC.dT.dT.dA Phosphoramidite Reagent (28) was used in the synthesis of a double modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as described previously. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4886.2, found 4885.2 (M)⁻.

Preparation of Compound M-11917 (SEQ ID NO:3): dC.dT.dT.dT.abT.abT.dG.dC.abT. dC.dG.dT.dC.dT.dT.dA Phosphoramidite Reagent (28) was used in the synthesis of a triple modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4927.3, found 4926.1 (M)⁻.

Preparation of Compound M-11918 (SEQ ID NO:4): dC.dT-.dT.dT.abT.abT.dG.dC.dT. dC.dG.dT.dC.dT.dA Phosphoramidite Reagent (28) was used in the synthesis of a double modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4886.2, found 4885.0 (M)⁻.

Preparation of Compound M-11919 (SEQ ID NO:5): lCs.dTs.dTs.dTs.abTs.abTs.dGs. lCs.dTs.lCs.lGs.dTs.lCs.dTs.lTs.lA Phosphoramidite Reagent (28) was used in the synthesis of the chimeric DNA/LNA/aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, exchanging 0.2 M PADS in 1:1 Pyridine/ACN for the oxidizing solution. The phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 5379.3, found 5378.3 (M)⁻.

Preparation of Compound M-11920 (SEQ ID NO:6): lCs.dTs.dTs.dTs.lTs.lTs.dGs.lCs. dTs.lCs.lGs.dTs.lCs.dTs.abTs.1A Phosphoramidite Reagent (28) was used in the synthesis of the chimeric DNA/LNA/aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, exchanging 0.2M PADS in 1:1 Pyridine/ACN for the oxidizing solution. The phosphoramidite reagents were added as a 0.1 M solution in acetonitrile during the appropriate coupling cycle described above in "General Synthetic Methodology of Truncated Nucleotides". The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 5366.3, found 5365.3 (M)⁻.

Preparation of Compound M-10930 (SEQ ID NO:7): dC.dT-.dT.dT.dT.dT.dG.dC.bT.dC. dG.dT.dC.dT.dT.dA Thymidyl-2'-C,4'-C-Bridged Bicyclonucleoside Phosphoramidite (see, for example, U.S. Pat. No. 6,403,566, Wang, G., Girardet, J., Gunic, E. Tetrahedron 55, 1999, 7707-7724) was used in the synthesis of a singly modified oxoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, and 0.025 M iodine solution. All phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4846.1, found 4845.8 (M)⁻.

Preparation of Compound M-10924 (SEQ ID NO:8): bC.bT-.bT.bT.bT.bT.dG.bC.bT.bC. dG.bT.bC.bT.bT.dA Thymidyl-2'-C,4'-C-Bridged Bicyclonucleoside Phosphoramidite and N-Bz-Cytidyl-2'-C,4'-C-Bridged Bicyclonucleoside Phosphoramidite (see, for example, U.S. Pat. No. 6,403,566, Wang, G., Girardet, J., Gunic, E. Tetrahedron 55, 1999, 7707-7724) was used in the synthesis of a singly modified oxoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, and 0.025 M iodine solution. All phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 5350.6, found 5350.2 (M)⁻.

Example 4: Functional Characterizations of Oligonucleotides Bearing 2'-C-Bridged Bicyclic Nucleotides Determination of Melting Temperature (Tm)

Melting temperature (Tm) is a critical parameter when designing synthetic oligonucleotide sequences as drugs directed towards antisense and microRNA targets. There is generally no specific Tm threshold above or below which determines activity. However, it is recognized that Tm must be significantly elevated for antisense and microRNA inhibitor oligonucleotide drugs. Furthermore, chemical modifications of the nucleotide backbones of synthetic oligonucleotide drugs (e.g., phosphorothioates) are often times used to impart stability against biodegradation in vivo. Nevertheless, most nucleotide phosphate backbone modifications often times cause decreases in the Tm of an oligonucleotide drug duplexed with its target. Accordingly, sufficient increases in the Tm of a synthetic oligonucleotide drug against its target sequence, over that inherent in natural DNA or RNA, 2'-OMe RNA, and other similar nucleotide units, are required for the synthetic oligonucleotide drug to have sufficient specificity, target engagement and ultimately downstream regulation of cellular processes controlled by the target.

The melting temperature (Tm) of modified 16 nucleotide phosphodiester strands were determined and compared to the Tm of identical 16 nucleotide sequences having natural phosphodiester DNA nucleotides. Specifically, the relative aminoCBBN melting temperature (Tm) compared to the 2'-deoxynucleoside or oxoCBBN nucleoside with the same nucleobase was determined on a per incorporation basis by determining the difference between the melting temperature of the amino-modified 16 nucleotide length phosphodiester strand and that of the identical 16 nucleotide sequence utilizing either the 2'-deoxynucleoside or oxoCBBN phosphodiester DNA nucleotide. Tm differences of substitutions were compared only when they were placed in the same position of the sequence. Comparable values for amino-LNA and its oxo-LNA counterpart were obtained through literature references (see Singh, S. K., Kumar, R., Wengel J. J. Org. Chem., Vol. 63, No. 26, 1998).

For example, the modified anti-208a oligonucleotides were annealed to the complementary sequence, twenty-two nucleotides in length, comprised of RNA nucleosides and a phosphate backbone. The complementary sequence was identical to the endogenous mature miRNA. Thermal denaturation temperatures (Tm) were measured as a maximum of the first derivative plot of melting curvex (A260 vs. Temp). The duplexes were constituted at 1 μM in a 0.9% NaCl buffer. Temperature was ramped from 25° C. to 95° C. at 1° C./min and OD's at 260 nm were read once per 30 seconds. Tm values are averages of at least two measurements.

Duplex melting temperatures for various modifications of a 16 nucleotide sequence, complementary to a nucleotide sequence of mature human miR-208a were measured using a Varian Cary 1E UV-Vis Spectrophotometer. Anti-miRNA 208a oligonucleotide sequences tested included a fully DNA phosphodiester (compound M-10931 (SEQ ID NO:9)), four DNA phosphodiester oligonucleotides with 1, 2 or 3 aminoCBBN thymidine residues in place of dT residues (compounds M-11915 (SEQ ID NO: 1), M-11916 (SEQ ID NO:2), M-11917 (SEQ ID NO:3), and M-11918 (SEQ ID NO:4)), mixed 9 LNA/7 DNA phosphorothioate oligonucleotide (compound M-10101 (SEQ ID NO:10)), and 2 mixed LNA/DNA/aminoCBBN phosphorothioate oligonucleotides where LNA thymidines of the parent compound, compound M-10101 (SEQ ID NO: 10), were replaced with either 1 or 2 aminoCBBN residues (compounds M-11920 (SEQ ID NO:6) and M-11919 (SEQ ID NO:5)). Duplexes were constituted at 1 μM in 0.9% NaCl. Temperature was ramped from 25° C. to 95° C. at 1° C./min and OD's at 260 nm were read once per 30 seconds.

Phosphodiester oligonucleotides with aminoCBBN modifications uniformly had higher melting temperature, therefore higher affinity, towards the complimentary sequence than their fully DNA counterpart (see Table 1). Affinity enhancements were on the order of 5-9° C./modification over DNA. These increases in affinity are as good as or better than literature values for LNA and aminoLNA.

TABLE 1 aminoCBBN, Phosphate Backbone Tm Studies, RNA Complement

| Oligo # | Oligo Name | Sequence | $T_m$ | $\Delta T_{m, DNA}$ | $\Delta T_m$/mod |
|---|---|---|---|---|---|
| 10931 (SEQ ID NO: 9) | 208a_DNA_PO | dC; dT; dT; dT; dT; dT; dG; dC; dT; dC; dG; dT; dC; dT; dT; dA | 53.1 | 0 | NA |
| 10924 (SEQ ID NO: 8) | 208a_CBBN C_T_DNA_16_3_PO | bC; bT; bT; bT; bT; bT; dG; bC; bT; bC; dG; bT; bC; bT; bT; dA | 89.8 | 36.7 | 2.8 |
| 10930 (SEQ ID NO: 7) | 208a_1CBBN_DNA_PO | dC; dT; dT; dT; dT; dT; dG; dC; bT; dC; dG; dT; dC; dT; dT; dA | 58.3 | 5.3 | 5.3 |
| 11915 (SEQ ID NO: 1) | 208a_1aminoCBBN_DNA_PO | dC; dT; dT; dT; dT; dT; dG; dC; abT; dC; dG; dC; dT; dT; dA | 62.0 | 8.9 | 8.9 |
| 11916 (SEQ ID NO: 2) | 208a_2aminoCBBN_DNA_PO | dC; dT; dT; dT; dT; abT; dG; dC; abT; dC; dG; dT; dC; dT; dT; dA | 64.6 | 11.5 | 5.8 |

TABLE 1-continued aminoCBBN, Phosphate Backbone Tm Studies, RNA Complement

| Oligo # | Oligo Name | Sequence | $T_m$ | $\Delta T_{m, DNA}$ | $\Delta T_m$/mod |
|---|---|---|---|---|---|
| 11917 (SEQ ID NO: 3) | 208a_3aminoCBBN_DNA_PO | dC; dT; dT; dT; abT; abT; dG; dC; abT; dC; dG; dT; dC; dT; dT; dA | 67.5 | 14.4 | 4.8 |
| 11918 (SEQ ID NO: 4) | 208a_2aminoCBBN_DNA_PO_isomer | dC; dT; dT; dT; abT; abT; dG; dC; dT; dC; dG; dT; dC; dT; dT; dA | 63.6 | 10.5 | 5.2 |

TABLE 2

Description of Notations

| deoxy A | dA | oxoCBBN A | bA |
| deoxy G | dG | oxoCBBN G | bG |
| deoxy C | dC | oxoCBBN C | bC |
| deoxy T | dT | OxoCBBN T | bT |
| Ina A | IA | aminoCBBN A | abA |
| InaG | IG | aminoCBBN G | abG |
| Ina C | IC | aminoCBBN C | abC |
| Ina T | IT | aminoCBBN T | abT |
| deoxy A P=S | dAs | | |
| deoxy G P=S | dGs | | |
| deoxy C P=S | dCs | | |
| deoxy T P=S | dTs | | |
| Ina A P=S | IAs | | |
| InaG P=S | IGs | | |
| Ina C P=S | ICs | | |
| Ina T P=S | ITs | | |

Figure 3B:
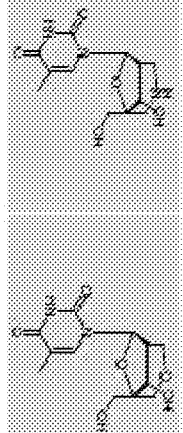
FIG. 3B provides a comparison chart of the affinity increases ($\Delta T_m$, c/modification) for amine 2'-C-Bridged Bicyclic Nucleoside (aminoCBBN) with its oxoCBBN counterpart. As shown, amine 2'-C-Bridged Bicyclic Nucleoside imparts much more affinity per modification than its oxoCBBN counterpart. Additionally, single and multiple aminoCBBN modifications within an oligonucleotide impart affinities equal to or greater than those of LNA nucleosides.

FIG. 3B). Without wishing to be bound by theory, it is postulated that the 2'-O of LNA, a proton acceptor, has a more stabilizing effect towards duplex hydration and stability than when it is replaced by a proton donor at the 2'-position as in the case of aminoLNA. Conversely, aminoCBBN appears to have a much more positive effect on duplex hydration and stability than its oxoCBBN analogue and offers Tm enhancements not seen in any other 2'4'-Carbon-Bridged Bicyclic Nucleotides. (see FIGS. 3A and 3B).

TABLE 3

| Oligo # | Oligo Name | Sequence | $T_m$ | $\Delta T_{m, parent}$ | $\Delta T_m$/mod |
|---|---|---|---|---|---|
| aminoCBBN, PS Backbone 10101-like Tm Studies, RNA Complement | | | | | |
| 10101 (SEQ ID NO: 10) | 208a_10101 | ICs; dTs; dTs; dTs; ITs; ITs; dGs; ICs; dTs; ICs; IGs; dTs; ICs; dTs; ITs; IA | 86.7 | NA | NA |
| 11919 (SEQ ID NO: 5) | 208a_10101_1aminoCBBN_PS | ICs; dTs; dTs; dTs; abTs; abTs; dGs; ICs; dTs; ICs; IGs; dTs; ICs; dTs; abTs; IA | 80.04 | −6.66 | −6.66 |
| 11920 (SEQ ID NO: 6) | 208a_10101_2minoCBBN_PS | ICs; dTs; dTs; dTs; ITs;ITs; dGs; ICs; dTs; ICs; IGs; dTs; ICs; dTs; abTs; IA | 85.125 | −1.575 | −0.7875 |
| amino-Nucleoside, Phosphate Backbone Tm Studies, RNA Complement | | | | | |
| (SEQ ID NO: 11) | DNA_9mer_PO_3LNA-T | dG; lT; dG; dA; lT; dA; lT; dG; dC | 50 | NA | NA |
| (SEQ ID NO: 12) | DNA_9mer_PO_3aminoLNA-T | dG; alT; dG; dA; alT; dA; alT; dG; dC | 47 | −1 | −1 |
| 10930 (SEQ ID NO: 7) | 208a_1CBBN_DNA_PO | dC; dT; dT; dT; dT; dT; dG; dC; bT; dC; dG; dT; dC; dT; dT; dA | 58.3 | NA | NA |
| 11915 (SEQ ID NO: 1) | 208a_1aminoCBBN_DNA_PO | dC; dT; dT; dT; dT; dT; dG; dC; abT; dC; dG; dT; dC; dT; dT; dA | 62.0 | +3.7 | +3.7 |

Comparison of the aminoLNA-T to its oxo-analogue, LNA-T, reveals that aminoLNA-T is less stabilizing toward its complement than LNA-T. Similarly, aminoENA-T appears to have very little duplex stabilizing effect over that of its oxo-analogue. Surprisingly, comparison of the aminoCBBN-T to its oxoCBBN-T analogue shows that the aminoCBBN modification is significantly more stabilizing than oxoCBBN-T by 2-4° C./modification (see Tables 3 and Cell Culture Activity of Anti-208a Oligonucleotides A HeLa cell line stably expressing miR-208a was generated. Specifically, a miRNA expression vector (Cell Bio-Labs, Inc.) expressing miR-208a was transfected into HeLa cells. Cells were then selected using a puromycin selection screen and clones which had detectable miR-208a expression as measured by qPCR were isolated (Ct value=~30).

The cells were plated in a black-walled 96 well plate with 10,000 cells per well. After twenty-four hours following plating, the cells were transfected with a dual-luciferase plasmid containing the miR-208a binding site in the 3' UTR of the renilla gene and various miR-208a inhibitors (compounds M-11919 (SEQ ID NO:5), M-11920 (SEQ ID NO:6), and M-10101 (SEQ ID NO:10)). Compound M-10591 was a non-targeting control. The cells were incubated for 24 hours at 37° C. and then both firefly (as a transfection normalization) and renilla levels were measured by luminescence using the Dual-Luciferase Reporter Assay System (Promega). Data was normalized to cells treated with only the miR-208a dual luciferase plasmid (psi check 208a). The psi check 2 cells were treated with a dual luciferase plasmid that does not include a miR-208a binding site.

Results demonstate that compound M-11919 (SEQ ID NO:5) has comparable activity as compound M-10101 (SEQ ID NO: 10), which is an optimized miR208a inhibitor that includes only LNA/DNA bases (see FIG. 4). Accordingly, multiple replacements of LNA residues with aminoCBBN residues result in full retention of miR208a inhibition activity. Compound M-11920 (SEQ ID NO:6) has slightly less activity compared to the other two inhibitors (see FIG. 4). The activity of compound M-11920 (SEQ ID NO:6) correlates with the Tm data which shows that compound M-11920 (SEQ ID NO:6) has less affinity for the miR-208a RNA than the M-11919 (SEQ ID NO:5) compound.

Example 5: Production of 2'-C-Brided Bicyclic Nucleosides

Figure 5:
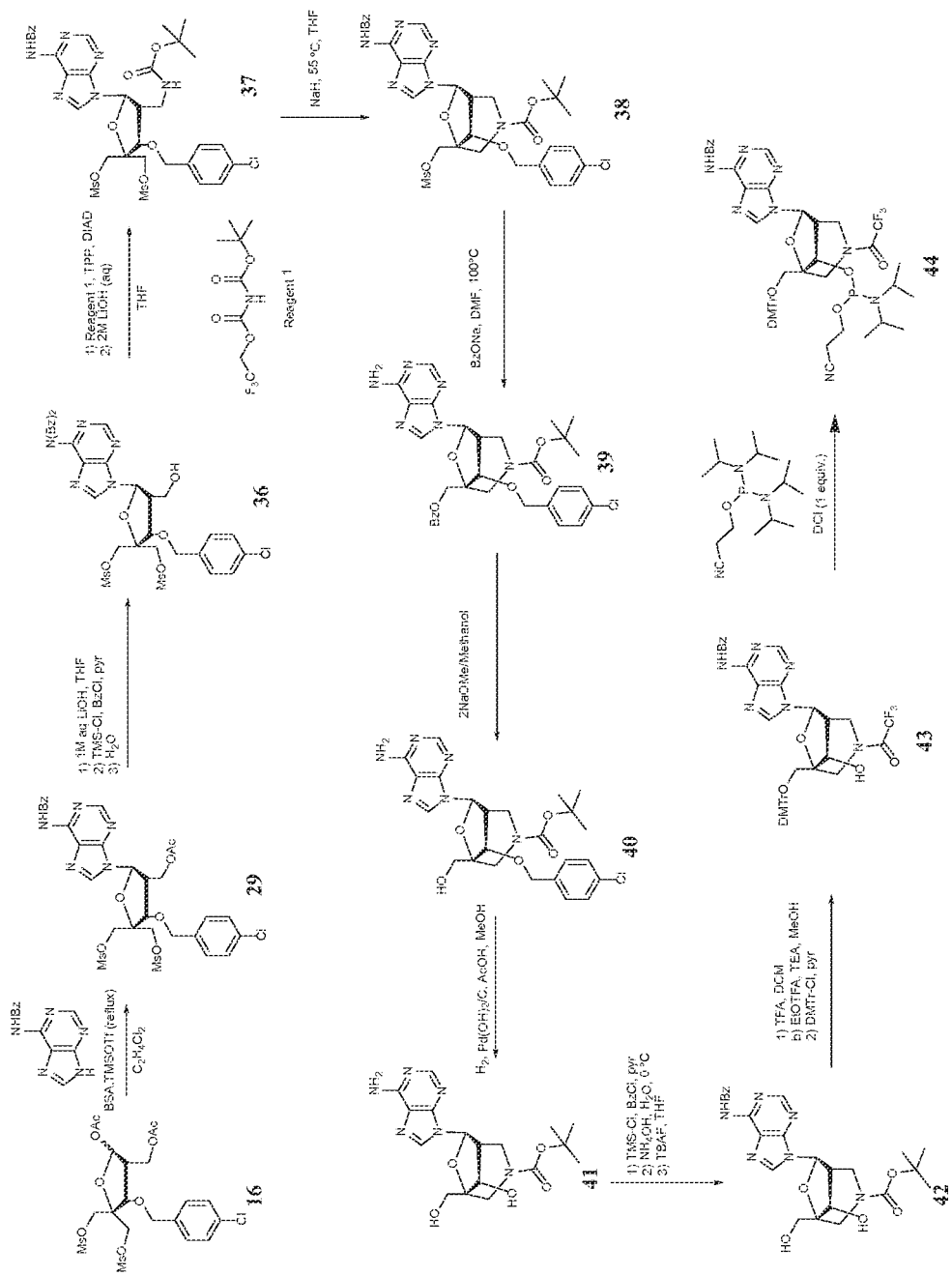
FIG. 5 provide exemplary production of a 2'-C-Bridged Bicyclic Nucleoside with adenine base and wherein "X" from Formula I is N.

This example describes further synthesis reactions and key intermediates in the production of 2'-C-Bridged Bicyclic Nucleosides with different nucleobases (see FIGS. 5-7), wherein "X" of Formula 1 is N.

Example 5A: 2'-C-Bridged Bicyclic Nucleoside (Adenosine)

((3R,4S)-4-((4-chlorobenzyl)oxy)-2-(6-N-Benzoyladenosin-yl)-5,5-bis(((methylsulfonyl)oxy)methyl) tetrahydrofuran-3-yl)methyl acetate (29)

N,O-Bis(trimethylsilyl)acetamide (27.6 ml, 113 mmol) was added to a mixture of ((3R,4S)-2-acetoxy-4-((4-chlorobenzyl)oxy)-5,5-bis(((methylsulfonyl)oxy)methyl)tetrahydrofuran-3-yl)methyl acetate (20.0 g, 37.7 mmol) and $N^6$-benzoyladenine (11.2 g, 47.1 mmol) in dichloroethane (100 ml). The reaction mixture was refluxed for 1 hour. The solution was cooled to 60° C. and TMS-OTf (13.6 ml, 75.3 mmol) was added. The mixture was refluxed for 4 hours. The solution was cooled to room temperature, diluted with $CH_2Cl_2$ (500 mL), and washed with saturated $NaHCO_3$ (2×200 mL) and brine (1×100 mL). The organic layer was dried ($Na_2SO_4$), concentrated under reduced pressure, and the residue was purified in two batches on a 340 g Biotage SNAP silica gel column, eluted via ethyl acetate. The pure fractions were combined and concentrated in a 1 L round bottomed flask to afford ((3R,4S)-4-((4-chlorobenzyl)oxy)-2-(6-N-Benzoyladenosin-yl)-5,5-bis(((methylsulfonyl)oxy) methyl)tetrahydrofuran-3-yl)methyl acetate (18.90 g, 25.6 mmol, 68% yield) as a white solid material. There were not any appreciable amounts of isolable nucleoside side products.

((3S,4R,5R)-5-(6-(N-benzoylbenzamido)-9H-purin-9-yl)-3-((4-chlorobenzyl)oxy)-4-(hydroxymethyl) tetrahydrofuran-2,2-diyl)bis(methylene) dimethanesulfonate (36)

The flask containing purified ((3R,4S)-4-((4-chlorobenzyl)oxy)-2-(6-N-Benzoyladenosin-yl)-5,5-bis(((methylsulfonyl)oxy)methyl)tetrahydrofuran-3-yl)methyl acetate (18.90 g, 25.6 mmol) was charged with THF (400 mL) and an 1.0M aqueous LiOH solution (113 mL, 1.0M). The mixture was allowed to stir 2 h at room temperature. TLC indicated that deacetylation had occurred while leaving the N-Benzoyl group intact. The reaction was diluted with water (200 mL) and extracted with ethyl acetate (3×300 mL). The organic phases were combined, washed with brine (1×200 mL), dried over $Na_2SO_4$, filtered into a 1000 mL round bottomed flask and concentrated in vacuo to give ((3S,4R,5R)-5-(6-benzamido-9H-purin-9-yl)-3-((4-chlorobenzyl) oxy)-4-(hydroxymethyl)tetrahydrofuran-2,2-diyl)bis(methylene) dimethanesulfonate (17.60 g, 25.3 mmol) as a white foam that was used without further purification. The flask was fitted with a stir bar and septum seal. The flask was charged with pyridine (200 mL) and cooled to ca. 5° C. in a water bath with stirring. Chlorotrimethylsilane (7.0 mL, 55 mmol) was added, dropwise, with stirring. The mixture was removed from the cooling bath and allowed to come to room temperature. After 30 minutes, benzoyl chloride (4.4 mL, 38 mmol) was added dropwise at room temperature and the mixture was allowed to stir overnight. Water was added to the reaction mixture (20 mL) and the mixture stirred for 30 minutes. The mixture was diluted with DCM (600 mL) and washed with brine (3×150 mL). The organic phase was dried over $Na_2SO_4$, filtered and concentrated to dryness. Half the residue was applied to a 340 g SNAP column and product was eluted via Biotage with a 40-100% EtOAc in hexanes gradient. The process was repeated for the second half of crude material. The product containing fractions were combined and concentrated to give pure ((3S,4R,5R)-5-(6-(N-benzoylbenzamido)-9H-purin-9-yl)-3-((4-chlorobenzyl) oxy)-4-(hydroxymethyl)tetrahydrofuran-2,2-diyl)bis (methylene) dimethanesulfonate (16.21 g, 80.1%) as a white foam.

((3S,4R,5R)-5-(6-benzamido-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (37)

((3S,4R,5R)-5-(6-(N-benzoylbenzamido)-9H-purin-9-yl)-3-((4-chlorobenzyl)oxy)-4-(hydroxymethyl)tetrahydrofuran-2,2-diyl)bis(methylene) dimethanesulfonate (16.2 g, 20.3 mmol), (2,2,2-Trifluoroethyl)-t-Butyl-iminodicarboxylate (6.16 g, 25.3 mmol) and triphenylphosphine (6.64 g, 25.3 mmol) were weighed into a 200 mL round-bottomed flask with a stir bar. The flask was charged with 200 mL of THF with stirring. DIAD (5.0 mL, 25.3 mmol) was added via syringe dropwise over 5 minutes and the mixture was allowed to stir for 45 min. TLC analysis of crude mixture (60/40 EtOAc/hexanes) revealed the reaction had gone to completion, giving rise to a new nucleoside positive spot (via Hannessians Stain). The mixture was concentrated to dryness and applied to a 340 g Biotage SNAP column and eluted with a 40-100% EtOAc in hexanes gradient over 9 column volumes. Product containing fractions were combined to give a white foam that was immediately re-dissolved in THF (500 mL) and treated with 2.0M LiOH (50.6 mL, 5 equiv) for 4 hours. TLC analysis revealed product went to a major product. No spot was apparent for fully de-benzoylated material. The product, ((3S,4R,5R)-5-(6-benzamido-9H-purin-9-yl)-4-(((tert-butoxycarbonyl)amino) methyl)-3-((4-chlorobenzyl)oxy)tetrahydrofuran-2,2-diyl) bis(methylene) dimethanesulfonate (15.8 g, 98.2%) was used, without further purification.

tert-butyl (1R,5R,7R,8S)-7-(6-benzamido-9H-purin-9-yl)-8-((4-chlorobenzyl)oxy)-5-(((methylsulfonyl) oxy)methyl)-6-oxa-3-azabicyclo[3.2.1]octane-3-carboxylate (38)

((3S,4R,5R)-5-(6-benzamido-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (5.0 g, 6.3 mmol) was weighed into a 1000 mL round bottomed flask with a stir bar. The flask was charged with THF (430 mL) and the solution allowed to stir. Sodium Hydride, 60% dispersion in oil (1.0 g, 25 mmol) was added to the solution, the flask was fitted with a reflux condenser vented to a drying tube and the reaction heated to 60° C. for 1.5 h. The reaction mixture was cooled in an ice bath, uncovered, and quenched by dropwise addition of 10 mL of water over 15 minutes. The mixture was concentrated, in vacuo, and re-suspended in ethyl acetate (300 mL). The organic phase was washed with brine (2×100 mL), dried over MgSO$_4$, filtered and concentrated to a tan foam. The foam was further purified by column chromatography by applying to a 340 g Biotage SNAP column and eluting with a 35-100% ethyl acetate in hexanes gradient over 6 column volumes. The pure fractions were combined and concentrated to give tert-butyl (1R,5R,7R,8S)-7-(6-benzamido-9H-purin-9-yl)-8-((4-chlorobenzyl)oxy)-5-(((methylsulfonyl)oxy)methyl)-6-oxa-3-azabicyclo[3.2.1]octane-3-carboxylate (2.31 g, 52.5%) as a white foam.

tert-butyl (1R,5R,7R,8S)-7-(6-benzamido-9H-purin-9-yl)-5-((benzoyloxy)methyl)-8-((4-chlorobenzyl)oxy)-6-oxa-3-azabicyclo[3.2.1]octane-3-carboxylate (39)

tert-butyl (1R,5R,7R,8S)-7-(6-benzamido-9H-purin-9-yl)-8-((4-chlorobenzyl)oxy)-5-(((methylsulfonyl)oxy)methyl)-6-oxa-3-azabicyclo[3.2.1]octane-3-carboxylate (1.70 g, 2.43 mmol) and sodium benzoate (1.75 g, 12.2 mmol) was weighed into a 250 mL round bottomed flask with a stir bar. The flask was charged with DMF (150 mL) and set to stir for 48 h at 100° C. The reaction mixture was concentrated to ⅓ volume in vacuo, diluted with saturated sodium bicarbonate solution (500 mL) and extracted with ethyl acetate (3×100 mL). The organic phases were combined and washed with brine (1×100 mL), dried over sodium sulfate, filtered and concentrated to give tert-butyl (1R,5R,7R,8S)-7-(6-benzamido-9H-purin-9-yl)-5-((benzoyloxy)methyl)-8-((4-chlorobenzyl)oxy)-6-oxa-3-azabicyclo[3.2.1]octane-3-carboxylate (1.75 g, 99.25%) as a white foam that is used without further purification.

tert-butyl (1R,5R,7R,8S)-7-(6-amino-9H-purin-9-yl)-8-((4-chlorobenzyl)oxy)-5-(hydroxymethyl)-6-oxa-3-azabicyclo[3.2.1]octane-3-carboxylate (40)

tert-butyl (1R,5R,7R,8S)-7-(6-benzamido-9H-purin-9-yl)-5-((benzoyloxy)methyl)-8-((4-chlorobenzyl)oxy)-6-oxa-3-azabicyclo[3.2.1]octane-3-carboxylate (6.85 g, 9.45 mmol) was weighed into a 250 mL round bottomed flask with a stir bar. The flask was charged with methanol (50 mL) and set to stir at 50° C. Sodium methoxide (0.51 g, 9.4 mmol) was added to the solution, which was allowed to stir for 2 h. The reaction mixture was cooled, concentrated to dryness and resuspended in DCM (250 mL). The organic phase was washed with brine (2×100 mL), dried over sodium sulfate, filtered and concentrated to dryness to afford tert-butyl (1R,5R,7R,8S)-7-(6-amino-9H-purin-9-yl)-8-((4-chlorobenzyl)oxy)-5-(hydroxymethyl)-6-oxa-3-azabicyclo[3.2.1]octane-3-carboxylate (4.25 g, 87.0%) as a white foam.

tert-butyl (1R,5R,7R,8S)-7-(6-benzamido-9H-purin-9-yl)-8-hydroxy-5-(hydroxymethyl)-6-oxa-3-azabicyclo[3.2.1]octane-3-carboxylate (42)

tert-butyl (1R,5R,7R,8S)-7-(6-amino-9H-purin-9-yl)-8-((4-chlorobenzyl)oxy)-5-(hydroxymethyl)-6-oxa-3-azabicyclo[3.2.1]octane-3-carboxylate (4.25 g, 8.22 mmol) was dissolved in ethanol (20 mL) and transferred to a 100 mL borosilicate bottle with a stir bar. Pearlman's catalyst (3 g) was added, at once to the solution. The uncapped bottle was placed inside a 300 mL Parr bomb, sealed and charged with hydrogen gas (60 psi). The apparatus was heated to 70° C. in an oil bath for 17 h. The apparatus was cooled in an ice bath and the pressure slowly released. The reaction mixture was removed from the Parr bomb and filtered through a pad of celite. The celite and catalyst were washed with warm ethanol (200 mL). the ethanol filtrate was concentrated in a 500 mL round bottomed flask, in vacuo, to give a dark foam that was co-evaporated with DCM (3×20 mL) to afford crude tert-butyl (1R,5R,7R,8S)-7-(6-benzamido-9H-purin-9-yl)-8-hydroxy-5-(hydroxymethyl)-6-oxa-3-azabicyclo[3.2.1]octane-3-carboxylate (41) mixed with a slight amount of catalyst. A stir bar was immediately added to the flask, which was charged with pyridine (50 mL) and septum sealed. The mixture was set to stir with cooling to 0° C. in an ice bath. TMS-Cl (2.6 mL, 21 mmol) was added, dropwise to the stirring solution. The reaction mixture was removed from the ice bath and allowed to warm to room temperature over 30 minutes. Benzoyl chloride ( ) was added dropwise to the reaction mixture. The reaction was allowed to stir for 3 h at room temperature. The reaction mixture quenched by addition of water (10 mL) with stirring for 5 min, followed by addition of concentrated ammonium hydroxide (20 mL) with stirring for an additional 15 minutes at room temperature. The mixture was concentrated in vacuo to dryness. The oil was dissolved in ethyl acetate (200 mL) then washed with saturated sodium bicarbonate solution (2×100 mL) and brine (2×100 mL). The organic phase was dried over sodium sulfate, filtered and concentrated to dryness. The residue was dissolved in THF (10 mL). 1.0M TBAF in THF (8.5 mL, 8.5 mmol) was added, with stirring. The reaction was stirred for 30 minutes before being diluted with ethyl acetate (100 mL). The organic phase was washed with 10% sodium citrate solution (2×50 mL) and brine (1×50 mL). The organic phase was dried over sodium citrate, filtered and concentrated to dryness. The residue was applied to a 100 g Biotage SNAP column and eluted with a 0-10% methanol in DCM gradient over nine column volumes. The pure fractions were combined and concentrated to give tert-butyl (1R,5R,7R,8S)-7-(6-benzamido-9H-purin-9-yl)-8-hydroxy-5-(hydroxymethyl)-6-oxa-3-azabicyclo[3.2.1]octane-3-carboxylate (2.00 g, 49.0%) as a white foam.

N-(9-((1R,5R,7R,8S)-8-hydroxy-5-(hydroxymethyl)-3-(2,2,2-trifluoroacetyl)-6-oxa-3-azabicyclo[3.2.1]octan-7-yl)-9H-purin-6-yl)benzamide tert-butyl (1R,5R,7R,8S)-7-(6-benzamido-9H-purin-9-yl)-8-hydroxy-5-(hydroxymethyl)-6-oxa-3-azabicyclo[3.2.1]octane-3-carboxylate (2.00 g, 4.03 mmol) was weighed in a 200 mL round bottomed flask with a stir bar. Dichloromethane (10 mL) and trifluoroacetic acid (10 mL) were added. The mixture was stirred, uncovered, for 30 minutes then concentrated to dryness. The residue was co-evaporated with methanol (2×10 mL). The residue was re-dissolved in methanol (20 mL) and ethyl trifluoroacetate (9.6 mL, 20 equiv.). Triethylamine (4.50 mL, 8 equiv.) was added to the solution and the mixture was stirred overnight, covered, at room temperature. The mixture was concentrated to dryness, dissolved in dichloromethane (100 mL) and washed with saturated sodium bicarbonate solution (2×50 mL) and brine (1×20 mL). The organic phase was dried over sodium sulfate, filtered and concentrated to afford N-(9-((1R,5R,7R,8S)-8-hydroxy-5-(hydroxymethyl)-3-(2,2,2-trifluoroacetyl)-6-oxa-3-azabicyclo[3.2.1]octan-7-yl)-9H-purin-6-yl)benzamide (1.80 g, 90.8%) as a white foam that was used without further purification.

N-(9-((1R,5R,7R,8S)-5-((4,4'-dimethoxytrityloxy) methyl)-8-hydroxy-3-(2,2,2-trifluoroacetyl)-6-oxa-3-azabicyclo[3.2.1]octan-7-yl)-9H-purin-6-yl)benzamide [DMTr-aA(Bz)(tfa)] (43)

N-(9-((1R,5R,7R,8S)-8-hydroxy-5-(hydroxymethyl)-3-(2,2,2-trifluoroacetyl)-6-oxa-3-azabicyclo[3.2.1]octan-7-yl)-9H-purin-6-yl)benzamide (1.80 g, 3.65 mmol) was weighed into a 100 mL round bottomed flask with a stir bar. The flask was charged with pyridine (30 mL) and set to stir. 4,4'-Dimethoxytrityl chloride (1.49 g, 4.39 mmol) was added at once to the solution. The flask was septum sealed and the mixture allowed to stir 17 h. Methanol (2 mL) was added to the reaction mixture, which was stirred for an additional 30 minutes. Saturated sodium bicarbonate solution (4 mL) was added to the reaction mixture which was then evaporated to dryness. The residue was suspended in DCM, filtered and applied to a TEA pre-treated 100 g Biotage SNAP column. Product was eluted with a 30-100% ethyl acetate in hexanes gradient over 6 column volumes. Fractions containing product were combined to afford N-(9-((1R,5R,7R,8S)-5-((4,4'-dimethoxytrityloxy)methyl)-8-hydroxy-3-(2,2,2-trifluoroacetyl)-6-oxa-3-azabicyclo[3.2.1]octan-7-yl)-9H-purin-6-yl)benzamide (1.50 g, 51.6%) as a white foam.

DMTr-aA(Bz)(tfa) Amidite (44)

DMTr-aA(Bz)(tfa) (1.50 g, 1.89 mmol) was weighed in a 100 mL round bottomed flask with a stir bar and septum seal. The flask was charged with DCM (30 mL) and 2-Cyanoethyl N,N,N',N'-tetraisopropylphosphordiamidite (1.14 g, 3.78 mmol). 4,5-Dicyanoimidazole (0.22 g, 1.9 mmol) was added, at once, and the reaction mixture was allowed to stir overnight. The reaction mixture was diluted with DCM (40 mL), washed with saturated sodium bicarbonate solution (2×50 mL) and brine (1×50 mL), dried over sodium sulfate, filtered and concentrated. The residue was applied to a TEA treated 100 g Biotage SNAP column and eluted with a 30-100% ethyl acetate in hexanes gradient over 6 column volumes. Fractions containing product were combined to afford DMTr-aA(Bz)(tfa) Amidite (1.64 g, 87.3%) as a white foam.

Example 5B: 2'-C-Bridged Bicyclic Nucleoside (Guanosine)

((2R,3R,4S)-2-(2-amino-6-chloro-9H-purin-9-yl)-4-((4-chlorobenzyl)oxy)-5,5-bis(((methylsulfonyl)oxy) methyl)tetrahydrofuran-3-yl)methyl acetate (45)

((2S,3R,4S)-4-((4-chlorobenzyl)oxy)-2-methoxy-5,5-bis (((methylsulfonyl)oxy)methyl)tetrahydrofuran-3-yl)methyl acetate (15.00 g, 28.25 mmol) was weighed into a 500 mL round-bottomed flask with a stir bar. The flask was charged with acetic anhydride (10.68 ml, 113 mmol) and acetic acid (60 mL). The mixture was stirred at 60° C. until all solids effected solution. Concentrated sufuric acid (75 uL, 0.05 equiv.) was added dropwise and the mixture is allowed to stir at 60° C. for an additional 5 minutes. The reaction mixture was removed from heat and allowed to come to room temperature, with stirring, overnight. The reaction mixture was diluted with ethyl acetate (300 mL), transferred to a separatory funnel and washed with brine (3×200 mL). The organic phase was carefully neutralized with a saturated bicarbonate wash (2×200 mL) and a final brine wash (100 mL). The organic phase was dried over sodium sulfate, filtered into a 500 mL round-bottomed flask and concentrated to give a clear, light yellow-brown oil that was used directly crude.

2-Amino-6-chloropurine (6.23 g, 36.7 mmol) and a stir bar were added to the resultant oil and the flask was fitted with a reflux condenser that was vented to a drying tube. The flask was charged with N,O-bistrimethylsilylacetamide (19.34 mL, 79.1 mmol) and acetonitrile. The mixture was stirred at reflux in an oil bath for 45 minutes, when the mixture had become a homogenous solution. The reaction mixture was briefly removed from the oil bath and allowed to slightly cool before dropwise addition of trimethylsilyl triflate (10.23 mL, 56.5 mmol). After addition was complete, the reaction mixture was returned to reflux for 1.5 hr. In process monitoring via TLC (60% EtOAc/Hex, UV & Hannessian's Stain visualiztion, Rf 0.5) revealed the emergence of a major UV product and complete consumption of the starting sugar.

The reaction mixture was cooled to room temperature and diluted with ethyl acetate (500 mL). The organic phase was washed with saturated sodium bicarbonate (2×200 mL) and brine (1×100 mL). The organic phase was dried over sodium sulfate, filtered and concentrated. The crude product was split in half and each portion subjected to silica gel chromatography (Biotage Isolera, 340 g SNAP column). All pure fractions were combined to give the N9, beta glycoside, ((2R,3R,4S)-2-(2-amino-6-chloro-9H-purin-9-yl)-4-((4-chlorobenzyl)oxy)-5,5-bis(((methylsulfonyl)oxy)methyl) tetrahydrofuran-3-yl)methyl acetate as a white foam (9.80 g, 51%).

((3S,4R,5R)-5-(2-amino-6-chloro-9H-purin-9-yl)-3-((4-chlorobenzyl)oxy)-4-(hydroxymethyl)tetrahydrofuran-2,2-diyl)bis(methylene) dimethanesulfonate (46)

((2R,3R,4S)-2-(2-amino-6-chloro-9H-purin-9-yl)-4-((4-chlorobenzyl)oxy)-5,5-bis(((methylsulfonyl)oxy)methyl) tetrahydrofuran-3-yl)methyl acetate (9.80 g, 14.6 mmol) was weighed into a 500 mL round bottomed flask with a stir bar. The flask was charged with THF (100 mL) and aqueous 1.0M LiOH solution (44 mL, 3 equiv.). The mixture was allowed to stir for 6 hours. The mixture was diluted with ethyl acetate (500 mL) and washed with brine (2×100 mL). The organic phase was dried over sodium sulfate, filtered and concentrated to give ((3S,4R,5R)-5-(2-amino-6-chloro-9H-purin-9-yl)-3-((4-chlorobenzyl)oxy)-4-(hydroxymethyl) tetrahydrofuran-2,2-diyl)bis(methylene) dimethanesulfonate (9.184 g, 99%) as a white foam that was used without further purification.

Figure 6:
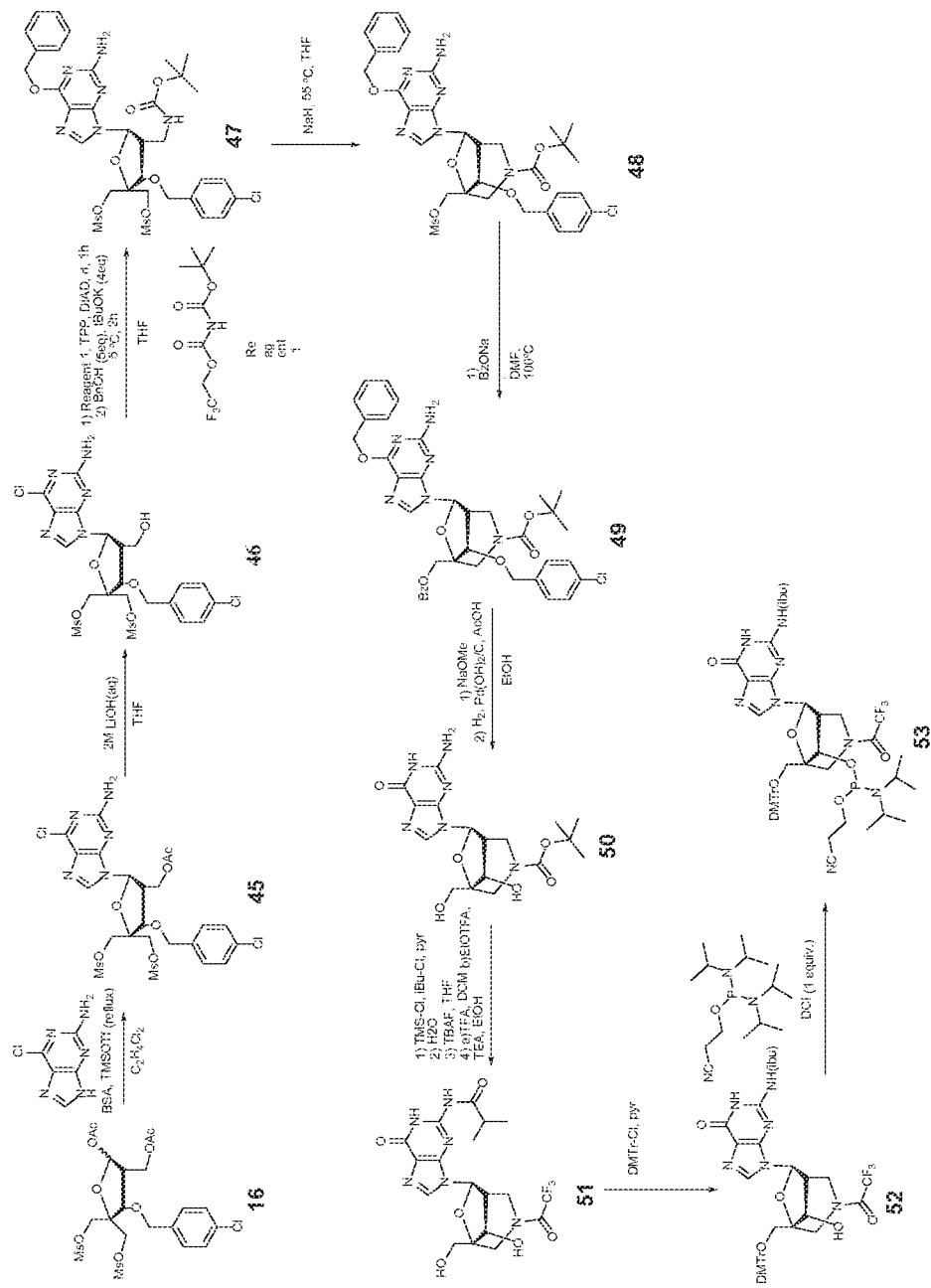
FIG. 6 provide exemplary production of a 2'-C-Bridged Bicyclic Nucleoside with guanine base and wherein "X" from Formula I is N.

((3R,4R,5R)-5-(2-amino-6-chloro-9H-purin-9-yl)-4-((N-(tert-butoxycarbonyl)-2,2,2-trifluoroethylcarbamoyl)methyl)-3-((4-chlorobenzyl)oxy)tetrahydrofuran-2,2-diyl)bis(methylene) dimethanesulfonate(2, 2,2-trifluoroethyl)-tert-butyl-iminodicarbonate (FIG. 6)

((3S,4R,5R)-5-(2-amino-6-chloro-9H-purin-9-yl)-3-((4-chlorobenzyl)oxy)-4-(hydroxymethyl)tetrahydrofuran-2,2-diyl)bis(methylene) dimethanesulfonate (9.09 g, 14.51 mmol), triphenylphosphine (5.709 g, 21.8 mmol) and (2,2, 2-Trifluoroethyl)-t-Butyl-iminodicarboxylate (5.29 g, 21.8 mmol) were added to a 500 mL round bottomed flask with a stir bar. The flask was charged with THF, septum sealed and set to stir in a 20° C. water bath. Diisopropylazodiimide (4.29 mL, 21.8 mmol) was added dropwise to the stirring reaction mixture over 3 minutes. The reaction mixture was allowed to stir for 1.5 hours. The mixture was concentrated to a solid. The material was immediately applied to a 340 g Biotage SNAP column and eluted with a 20-100% ethyl acetate in hexanes gradient over 9 column volumes. The pure fractions were combined and concentrated to give the product (11.75 g, 95.1%) as a white foam.

((3S,4R,5R)-5-(2-amino-6-chloro-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (FIG. 6)

((3R,4R,5R)-5-(2-amino-6-chloro-9H-purin-9-yl)-4-((N-(tert-butoxycarbonyl)-2,2,2-trifluoroethylcarbamoyl)methyl)-3-((4-chlorobenzyl)oxy)tetrahydrofuran-2,2-diyl)bis(methylene) dimethanesulfonate(2,2,2-trifluoroethyl)-tert-butyl-iminodicarbonate (11.7 g, 12.7 mmol) is weighed into a 500 mL round-bottomed flask with a stir bar. The flask is charged with THF (100 mL) and aqueous 1.0M LiOH solution (42 mL, 3 equiv.). The mixture is covered and stirred for 1.5 hrs at room temperature. The reaction is diluted with ethyl acetate (500 mL) and washed with brine (2×100 mL). The organic phase is dried over sodium sulfate, filtered and concentrated to dryness. The resultant foam was co-evaporated with ACN (2×100 mL) and brought to constant mass under high vacuum to give ((3S,4R,5R)-5-(2-amino-6-chloro-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (9.75 g, 97%) as a white foam.

((3S,4R,5R)-5-(2-amino-6-(benzyloxy)-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (47)

((3S,4R,5R)-5-(2-amino-6-chloro-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (9.75 g, 13.4 mmol) was weighed into a 500 mL round-bottomed flask with a stir bar. The flask was charged with ACN (150 mL) and benzyl alcohol, septum sealed, then cooled in a salt-ice bath with stirring. Potassium t-butoxide (2.38 g, 20.2 mmol) was added in 400 mg fractions over 20 minutes. After the last fraction was added, the reaction was allowed to continue stirring for 2 hours while maintaining the salt-ice bath temperature.

TLC of the reaction mixture (95:5 DCM:MeOH, UV/Hanessians Stain visualization) revels reaction is complete. The reaction mixture is diluted with water (400 mL) and extracted with ethyl acetate (3×250 mL). The organic phases are combined and washed with brine (1×100 mL), dried over sodium sulfate, filtered and concentrated to dryness. The resultant oil is applied to a TEA pre-treated Biotage SNAP column (340 g) and eluted with a 20-100% EtOAc/Hexanes gradient over 6 column volumes. The pure fractions were combined, taking special care to eliminate benzyl alcohol, and concentrated to give ((3S,4R,5R)-5-(2-amino-6-(benzyloxy)-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (8.50 g, 79.3%) as a white foam.

tert-butyl (1R,5R,7R,8S)-7-(2-amino-6-(benzyloxy)-9H-purin-9-yl)-8-((4-chlorobenzyl)oxy)-5-(((methylsulfonyl)oxy)methyl)-6-oxa-3-azabicyclo[3.2.1]octane-3-carboxylate (48)

((3S,4R,5R)-5-(2-amino-6-(benzyloxy)-9H-purin-9-yl)-4-(((tert-butoxycarbonyl)amino)methyl)-3-((4-chloroben-zyl)oxy)tetrahydrofuran-2,2-diyl)bis(methylene) dimethanesulfonate (8.50 g, 10.7 mmol) was weighed into a 2 L round-bottomed flask with a stir bar. The flask was charged with THF (850 mL) and sodium hydride (4.26 g, 107 mmol), fitted with a reflux condenser with a drying tube vent and set to stir at 60° C. for 4 hours. The reaction mixture was cooled to 0° C. and quenched by the dropwise addition of 10 mL of water. The reaction mixture was concentrated in vacuo to dryness and re-dissolved in ethyl acetate (300 mL). The organic phase was washed with water (2×100 mL) and brine (1×100 mL), dried over sodium sulfate, filtered and concentrated to dryness. The residue was applied to a 340 g Biotage SNAP column and eluted with a 30-100% ethyl acetate gradient over 9 column volumes. Fractions containing product, tert-butyl (1R,5R,7R,8S)-7-(2-amino-6-(benzyloxy)-9H-purin-9-yl)-8-((4-chlorobenzyl)oxy)-5-(((methylsulfonyl)oxy)methyl)-6-oxa-3-azabicyclo[3.2.1]octane-3-carboxylate (4.70 g, 62.9%), and starting material, ((3S,4R,5R)-5-(2-amino-6-(benzyloxy)-9H-purin-9-yl)-4-(((tert-butoxycarbonyl)amino)methyl)-3-((4-chlorobenzyl)oxy)tetrahydrofuran-2,2-diyl)bis(methylene) dimethanesulfonate (2.32 g, 27.3%) were separately combined and concentrated to white foams.

tert-butyl (1R,5R,7R,8S)-7-(2-amino-6-(benzyloxy)-9H-purin-9-yl)-5-((benzoyloxy)methyl)-8-((4-chlorobenzyl)oxy)-6-oxa-3-azabicyclo[3.2.1]octane-3-carboxylate (49)

tert-butyl (1R,5R,7R,8S)-7-(2-amino-6-(benzyloxy)-9H-purin-9-yl)-8-((4-chlorobenzyl)oxy)-5-(((methylsulfonyl)oxy)methyl)-6-oxa-3-azabicyclo[3.2.1]octane-3-carboxylate (4.70 g, 6.70 mmol) and sodium benzoate (7.80 g, 54.1 mmol) was weighed into a 2 L round bottomed flask with a stir bar. The flask was charged with DMF (500 mL) and septum sealed. The mixture was heated to 100° C. with vigorous stirring overnight. The reaction mixture is concentrated at 50° C., under vacuum to approximately 100 mL. The mixture is diluted to 500 mL with saturated sodium bicarbonate. The aqueous phase is extracted with ethyl acetate (3×200 mL). The organic phases were combined and washed with brine (1×100 mL), dried over sodium sulfate, filtered and concentrated to give crude tert-butyl (1R,5R,7R,8S)-7-(2-amino-6-(benzyloxy)-9H-purin-9-yl)-5-((benzoyloxy)methyl)-8-((4-chlorobenzyl)oxy)-6-oxa-3-azabicyclo[3.2.1]octane-3-carboxylate (4.56 g, 93.6%) as a white foam that is used without further purification.

tert-Butyl (1R,5R,7R,8S)-7-(2-amino-6-oxo-1, 6-dihydro-9H-purin-9-yl)-8-hydroxy-5-(hydroxymethyl)-6-oxa-3-azabicyclo[3.2.1]octane-3-carboxylate (50)

tert-butyl (1R,5R,7R,8S)-7-(2-amino-6-(benzyloxy)-9H-purin-9-yl)-5-((benzoyloxy)methyl)-8-((4-chlorobenzyl)oxy)-6-oxa-3-azabicyclo[3.2.1]octane-3-carboxylate (2.40 g, 3.30 mmol) is weighed into a 250 mL round-bottomed flask with a stir bar. The flask is charged with ethanol (15 mL). Sodium methoxide (0.19 g, 3.30 mmol) is added to the mixture, the flask is septum sealed and warmed to 50° C. for 2 h. The solution is neutralized by addition of acetic acid (0.19 mL, 3.30 mmol). The mixture and stir bar is transferred to a 100 mL borosilicate bottle which is placed in a 300 mL Parr bomb. Pearlman's catalyst (1.50 g) was added to the mixture and the apparatus was sealed and charged with hydrogen gas (60 psi). The bomb apparatus was heated to 70° C. on a magnetic stir plate set to stir at 500 rpm for 17 h.

The apparatus was cooled to 0° C. and the pressure released before disassembling the bomb apparatus. The solution was filtered through a pad of celite to remove the majority of catalyst. The celite was washed with an additional 200 mL of warm ethanol. The filtrate was concentrated to dryness and co-evaporated with dichloromethane (3×25 mL) to give tert-butyl (1R,5R,7R,8S)-7-(2-amino-6-oxo-1,6-dihydro-9H-purin-9-yl)-8-hydroxy-5-(hydroxymethyl)-6-oxa-3-azabicyclo[3.2.1]octane-3-carboxylate (1.12 g, 83.1%) as a white foam that is used without further purification.

N-(9-((1R,5R,7R,8S)-8-hydroxy-5-(hydroxymethyl)-3-(2,2,2-trifluoroacetyl)-6-oxa-3-azabicyclo[3.2.1]octan-7-yl)-6-oxo-6,9-dihydro-1H-purin-2-yl)isobutyramide (51)

tert-butyl (1R,5R,7R,8S)-7-(2-amino-6-oxo-1,6-dihydro-9H-purin-9-yl)-8-hydroxy-5-(hydroxymethyl)-6-oxa-3-azabicyclo[3.2.1]octane-3-carboxylate (0.45 g, 1.1 mmol) was weighed into a 100 mL round bottomed flask with a magnetic stir bar and septum seal. The flask is charged with pyridine (10 mL) and cooled to 0° C. in an ice bath. TMS-Cl (0.42 mL, 3.3 mmol) is added to the mixture dropwise and the reaction is allowed to stir for 30 minutes. Isobutyryl chloride (0.13 mL, 1.2 mmol) is added dropwise to the stirring mixture which is allowed to come to room temperature over 3 h. The reaction mixture is unsealed, quenched with water (2 mL) and allowed to stir for 30 minutes. The quenched reaction is diluted with ethyl acetate (100 mL) and extracted with saturated sodium bicarbonate solution (2×50 mL) and brine (1×50 mL). The organic phase was dried over sodium sulfate, filtered and concentrated to give a crude foam that was immediately subjected to treatment with 0.5M TBAF in THF (2.4 mL, 1.1 equiv.), with stirring, for 30 minutes. The mixture was diluted with dichloromethane (40 mL) and washed with 10% aqueous sodium citrate (2×20 mL). the organic phase was washed with brine (1×10 mL), dried over sodium sulfate, filtered and concentrated to a yellow, brown powder that was immediately subjected to 10 mL of 1:1 TFA:DCM, with stirring, for 45 minutes. The mixture was evaporated to dryness and co-evaporated with ethanol (2×10 mL). The resultant solid was re-dissolved in ethanol (10 mL) and ethyl trifluoroacetate (2.5 mL, 21.55 mmol). Triethylamine was added to the stirring mixture (2.2 mL, 15.67 mmol), which was allowed to stir overnight at room temperature. The reaction mixture was concentrated in vacuo and partitioned with dichloromethane (30 mL) and saturated sodium bicarbonate solution (20 mL). The bicarbonate solution was further extracted with DCM (2×10 mL). The organic phases were combined, washed with brine (1×20 mL), dried over sodium sulfate, filtered and concentrated to give N-(9-((1R,5R,7R,8S)-8-hydroxy-5-(hydroxymethyl)-3-(2,2,2-trifluoroacetyl)-6-oxa-3-azabicyclo[3.2.1]octan-7-yl)-6-oxo-6,9-dihydro-1H-purin-2-yl)isobutyramide (0.38 g, 73%) as a tan foam that is used without further purification.

DMTr-aG(ibu)(tfa) (52)

N-(9-((1R,5R,7R,8S)-8-hydroxy-5-(hydroxymethyl)-3-(2,2,2-trifluoroacetyl)-6-oxa-3-azabicyclo[3.2.1]octan-7-yl)-6-oxo-6,9-dihydro-1H-purin-2-yl)isobutyramide (0.38 g, 0.80 mmol) was weighed into a 100 mL round bottomed flask with a stir bar and septum seal. The flask was charged with pyridine (10 mL) and 4,4'-dimethoxytrityl chloride (0.326 g, 0.96 mmol) was added at once. The flask was covered and allowed to stir overnight at room temperature. The reaction was quenched by addition of methanol (0.5 mL). Saturated sodium bicarbonate solution (4 mL) was added to the reaction mixture which was then evaporated to dryness. The residue was suspended in DCM, filtered and applied to a TEA pre-treated 50 g Biotage SNAP column. Product was eluted with a 30-100% ethyl acetate in hexanes gradient over 6 column volumes. Fractions containing product were combined to afford DMTr-aG(ibu)(tfa) (0.41 g, 65.9%) as a white foam.

DMTr-aG(ibu)(tfa) Amidite (53)

DMTr-aG(ibu)(tfa) (0.40 g, 0.53 mmol) was weighed in a 100 mL round bottomed flask with a stir bar and septum seal. The flask was charged with DCM (10 mL) and 2-Cyanoethyl N,N,N',N'-tetraisopropylphosphordiamidite (0.32 g, 1.06 mmol). 4,5-Dicyanoimidazole (62.4 mg, 0.53 mmol) was added, at once, and the reaction mixture was allowed to stir overnight. The reaction mixture was diluted with DCM (40 mL), washed with saturated sodium bicarbonate solution (2×50 mL) and brine (1×50 mL), dried over sodium sulfate, filtered and concentrated. The residue was applied to a TEA treated 100 g Biotage SNAP column and eluted with a 30-100% ethyl acetate in hexanes gradient over 9 column volumes. Fractions containing product were combined to afford DMTr-aG(ibu)(tfa) Amidite (0.39 g, 76%) as a white foam.

Example 5C: 2'-C-Bridged Bicyclic Nucleoside (Cytosine)

tert-butyl (1R,5R,7R,8S)-7-(4-amino-5-methyl-2-oxopyrimidin-1(2H)-yl)-5-(hydroxymethyl)-8-((trimethylsilyl)oxy)-6-oxa-3-azabicyclo[3.2.1]octane-3-carboxylate (55)

tert-butyl (1R,5R,7R,8S)-8-hydroxy-5-(hydroxymethyl)-7-(5-methyl-2,4-dioxo-3,4-dihydropyrimidin-1(2H)-yl)-6-oxa-3-azabicyclo[3.2.1]octane-3-carboxylate, 54, (0.80 g, 2.1 mmol) was weighed into a 100 mL round bottomed flask with a stir bar and septum seal. The flask was charged with ACN (10 mL) and TEA (1.16 mL, 8.35 mmol) then cooled to 0° C. TMS-Cl (0.583 mL, 4.60 mmol) was added, dropwise over 5 minutes with stirring. The mixture was allowed to stir while coming to room temperature for 30 min.

In a separate 250 mL round bottomed flask, 1,2,4-1H-Triazole (1.441 g, 20.9 mmol) was added with a stir bar and septum seal. The flask was flush with argon and cooled to 0° C. in an ice bath. The flask was charged with ACN (20 mL) and TEA (2.90 mL, 20.9 mmol) then set to stir. POCl$_3$ was added dropwise over 5 minutes with vigorous stirring. The silylated nucleoside solution was taken up in a syringe and added to the cooled POCl$_3$/triazole solution, dropwise over several minutes. The reaction was removed from the ice bath and allowed to come to room temperature over 1 h. The reaction mixture is diluted with ethyl acetate (200 mL) and washed carefully with saturated sodium bicarbonate (2×100 mL) and brine (1×50 mL). The organic phase is dried over sodium sulfate, filtered and concentrated to a yellow foam in a 100 mL round bottomed flask with a stir bar. The flask is sealed and charged with ACN (15 mL) and saturated ammonia solution (15 mL). The mixture is stirred 17 h at room temperature before being unsealed. The mixture is concentrated to dryness, re-dissolved in DCM (50 mL) and the organic phase washed with saturated sodium bicarbonate (2×10 mL) and brine (1×10 mL). The organic phase was dried over sodium sulfate, filtered and concentrated to dryness to give crude tert-butyl (1R,5R,7R,8S)-7-(4-amino-5-methyl-2-oxopyrimidin-1(2H)-yl)-5-(hydroxymethyl)-8-((trimethylsilyl)oxy)-6-oxa-3-azabicyclo[3.2.1]octane-3-carboxylate (0.63 g, 66.4%) as a yellow-tan foam.

tert-butyl (1R,5R,7R,8S)-7-(4-benzamido-5-methyl-2-oxopyrimidin-1(2H)-yl)-8-hydroxy-5-(hydroxymethyl)-6-oxa-3-azabicyclo[3.2.1]octane-3-carboxylate (56)

tert-Butyl (1R,5R,7R,8S)-7-(4-amino-5-methyl-2-oxopyrimidin-1(2H)-yl)-5-(hydroxymethyl)-8-((trimethylsilyl)oxy)-6-oxa-3-azabicyclo[3.2.1]octane-3-carboxylate (0.60 g, 1.3 mmol) was weighed into a 100 mL round bottomed flask with a stir bar and septum seal. The flask was charged with pyridine (25 mL) and the mixture was set to stir with cooling to 0° C. in an ice bath. TMS-Cl (0.25 mL, 2.0 mmol) was added, dropwise to the stirring solution. The reaction mixture was removed from the ice bath and allowed to warm to room temperature over 30 minutes. Benzoyl chloride (0.17 mL, 1.4 mmol) was added dropwise to the reaction mixture. The reaction was allowed to stir for 3 h at room temperature. The reaction mixture quenched by addition of water (6 mL) with stirring for 5 min, followed by addition of concentrated ammonium hydroxide (10 mL) with stirring for an additional 15 minutes at room temperature. The mixture was concentrated in vacuo to dryness. The oil was dissolved in ethyl acetate (200 mL) then washed with saturated sodium bicarbonate solution (2×100 mL) and brine (2×100 mL). The organic phase was dried over sodium sulfate, filtered and concentrated to dryness. The residue was dissolved in THF (5 mL). 1.0M TBAF in THF (2.5 mL, 2.5 mmol) was added, with stirring. The reaction was stirred for 30 minutes before being diluted with DCM (50 mL). The organic phase was washed with 10% sodium citrate solution (2×10 mL) and brine (1×10 mL). The organic phase was dried over sodium sulfate, filtered and concentrated to dryness. The residue was applied to a 25 g Biotage SNAP column and eluted with a 0-10% methanol in DCM gradient over nine column volumes. The pure fractions were combined and concentrated to give tert-butyl (1R,5R,7R,8S)-7-(4-benzamido-5-methyl-2-oxopyrimidin-1(2H)-yl)-8-hydroxy-5-(hydroxymethyl)-6-oxa-3-azabicyclo[3.2.1]octane-3-carboxylate (0.49 g, 76.3%) as a white foam.

Figure 7:
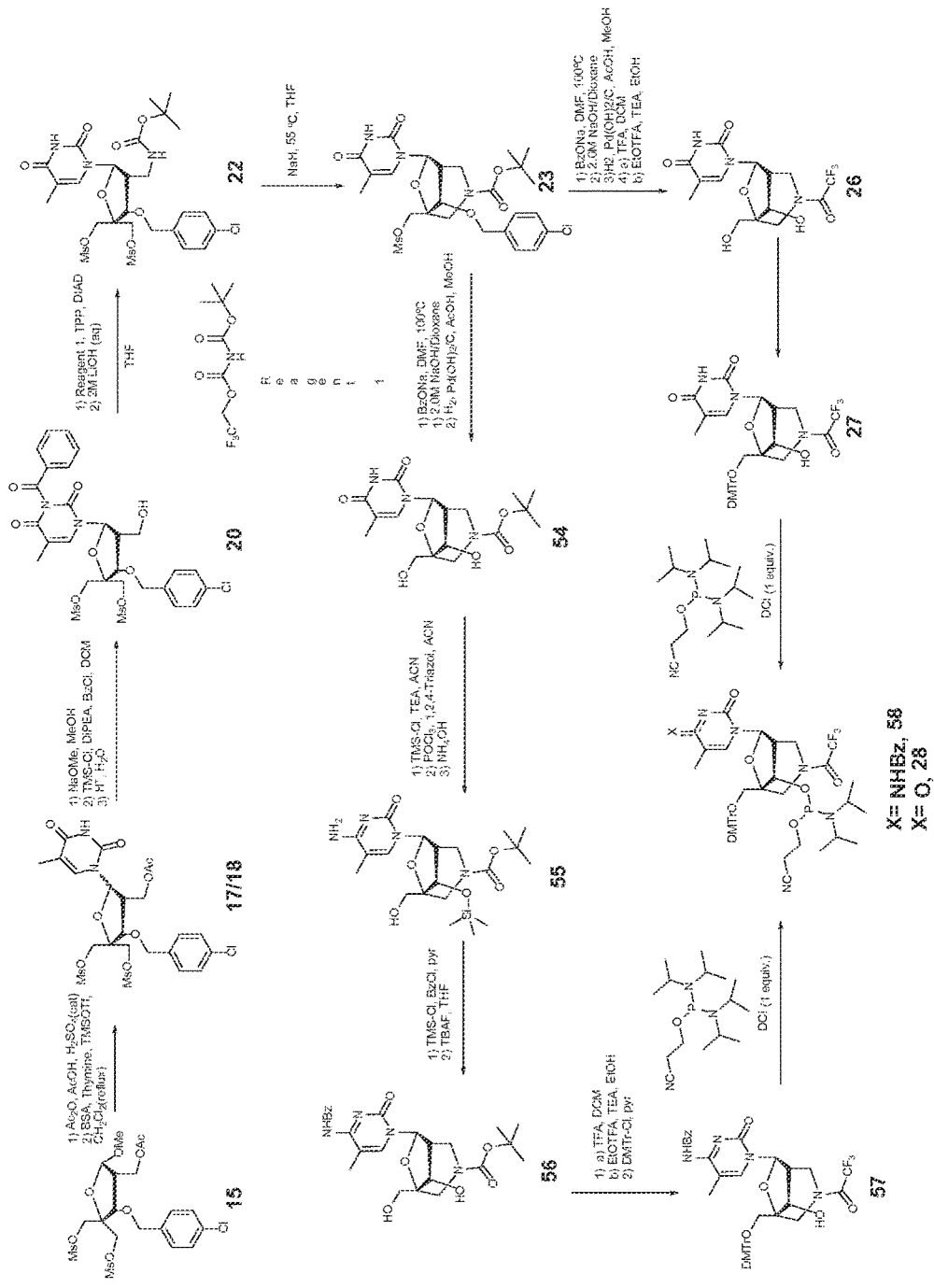
FIG. 7 provide exemplary production of a 2'-C-Bridged Bicyclic Nucleoside with thymine base and wherein "X" from Formula I is N.

N-(1-((1R,5R,7R,8S)-8-hydroxy-5-(hydroxymethyl)-3-(2,2,2-trifluoroacetyl)-6-oxa-3-azabicyclo[3.2.1]octan-7-yl)-5-methyl-2-oxo-1,2-dihydropyrimidin-4-yl)benzamide (FIG. 7)

tert-butyl (1R,5R,7R,8S)-7-(4-benzamido-5-methyl-2-oxopyrimidin-1(2H)-yl)-8-hydroxy-5-(hydroxymethyl)-6-oxa-3-azabicyclo[3.2.1]octane-3-carboxylate (0.49 g, 1.0 mmol) was weighed into a 50 mL round bottomed flask with a stir bar. The flask is charged with DCM (5 mL) and trifluoroacetic acid, with stirring. After 30 minutes, the solution is concentrated in vacuo to dryness. The residue is co-evaporated with ethanol (2×10 mL). The resultant material is re-dissolved in ethanol (10 mL), ethyl trifluoroacetate (2.4 mL, 20 mmol) and trimethylamine (1.4 mL, 10 mmol). The mixture is stirred overnight at room temperature. The mixture is evaporated to dryness and directly applied to a 25 g Biotage SNAP column and eluted with a 0-10% methanol in DCM gradient over nine column volumes. The pure fractions were combined and concentrated to give N-(1-((1R,5R,7R,8S)-8-hydroxy-5-(hydroxymethyl)-3-(2,2,2-trifluoroacetyl)-6-oxa-3-azabicyclo[3.2.1]octan-7-yl)-5-methyl-2-oxo-1,2-dihydropyrimidin-4-yl)benzamide (0.35 g, 72%) as a white foam.

N-(1-((1R,5R,7R,8S)-5-((bis(4-methoxyphenyl)(phenyl)methoxy)methyl)-8-hydroxy-3-(2,2,2-trifluoroacetyl)-6-oxa-3-azabicyclo[3.2.1]octan-7-yl)-5-methyl-2-oxo-1,2-dihydropyrimidin-4-yl)benzamide (57)

N-(1-((1R,5R,7R,8S)-8-hydroxy-5-(hydroxymethyl)-3-(2,2,2-trifluoroacetyl)-6-oxa-3-azabicyclo[3.2.1]octan-7-yl)-5-methyl-2-oxo-1,2-dihydropyrimidin-4-yl)benzamide (0.35 g, 0.73 mmol) from the previous step was weighed into a 50 mL round bottomed flask with a stir bar and septum seal. The flask was charged with pyridine (10 mL) and 4,4'-dimethoxytrityl chloride (0.295 g, 0.87 mmol) was added at once. The flask was covered and allowed to stir overnight at room temperature. The reaction was quenched by addition of methanol (0.5 mL). Saturated sodium bicarbonate solution (4 mL) was added to the reaction mixture which was then evaporated to dryness. The residue was suspended in DCM, filtered and applied to a TEA pre-treated 50 g Biotage SNAP column. Product was eluted with a 30-100% ethyl acetate in hexanes gradient over 6 column volumes. Fractions containing product were combined to afford N-(1-((1R,5R,7R,8S)-5-((bis(4-methoxyphenyl)(phenyl)methoxy)methyl)-8-hydroxy-3-(2,2,2-trifluoroacetyl)-6-oxa-3-azabicyclo[3.2.1]octan-7-yl)-5-methyl-2-oxo-1,2-dihydropyrimidin-4-yl)benzamide [DMTr-aC(Bz)(tfa)] (0.35 g, 61.5%) as a white foam.

DMTr-aC(Bz)(tfa) Amidite (58)

DMTr-aC(Bz)(tfa) (0.35 g, 0.45 mmol) was weighed in a 100 mL round bottomed flask with a stir bar and septum seal. The flask was charged with DCM (7 mL) and 2-Cyanoethyl N,N,N',N'-tetraisopropylphosphordiamidite (0.27 g, 0.89 mmol). 4,5-Dicyanoimidazole (53 mg, 0.45 mmol) was added, at once, and the reaction mixture was allowed to stir overnight. The reaction mixture was diluted with DCM (40 mL), washed with saturated sodium bicarbonate solution (2×20 mL) and brine (1×10 mL), dried over sodium sulfate, filtered and concentrated. The residue was applied to a TEA treated 25 g Biotage SNAP column and eluted with a 30-100% ethyl acetate in hexanes gradient over 9 column volumes. Fractions containing product were combined to afford DMTr-aC(Bz)(tfa) Amidite (0.38 g, 86%) as a white foam.

What is claimed is:

1. A method for producing a β-anomer of a 2'C-Bridged Bicyclic Nucleoside or Nucleotide, comprising the steps of:
   a) glycosylating a nucleobase, wherein the glycosyl donor contains a protected alkylhydroxy or alkylamine at the 2' position; and
   b) cyclizing the 2' and 4' positions of the glycosyl group.

2. The method of claim 1, further comprises a step of purifying or recovering the β-anomer of the 2'C-Bridged Bicyclic Nucleoside or Nucleotide.

3. The method of claim 1, wherein the 2'C-Bridged Bicyclic Nucleoside or Nucleotide has the structure of Formula I, or a phosphoramidite thereof:

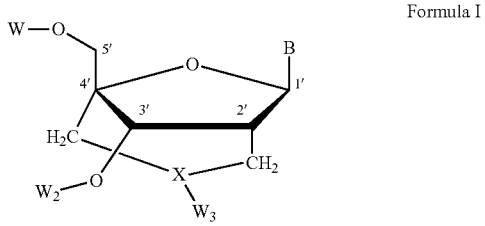

Formula I wherein
X is selected from N, S, or O;
$W_1$ and $W_2$ are each independently selected from H, an alcohol protecting group, a phosphate ester comprising the O depicted, a phosphorothioate ester comprising the O depicted, di- or tri-phosphate, or phosphoramidite;
$W_3$ is independently selected from null, H, O, an amine protecting group, phosphoramidite, a phosphoramidate ester comprising the N when X is N, a phosphordiamidate ester comprising the N when X is N, methyl, alkyl, cycloalkyl, carboxamide, a sugar, a fatty acid, other molecular conjugate, —$C_1$(O)R, or —COOR, wherein R is aryl; linear, branched or cyclic alkyl or alkenyl; sugar, fatty acid, or other molecular conjugate; and
B is a nucleobase.

4. The method of claim 3, wherein X is N.
5. The method of claim 3, wherein X is S.
6. The method of claim 3, wherein X is O.
7. The method of claim 1, wherein the nucleobase is a purine.
8. The method of claim 7, wherein the nucleobase is an adenine, guanine, or a derivative thereof.

9. The method of claim 1, wherein the nucleobase is a pyrimidine.
10. The method of claim 9, wherein the nucleobase is a thymine, cytosine, or uracil, or a derivative thereof.
11. The method of claim 1, wherein the nucleobase is persilylated.
12. The method of claim 3, wherein the alcohol protecting group is selected from 4,4'-dimethoxytrityl, ester, silyl, or acid labile ether.
13. The method of claim 3, wherein the amine protecting group is selected from carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), or trifluoroacetyl (tfa).
14. The method of claim 1, wherein the glycosyl donor contains an acetyl-protected methylhydroxy at the 2' position, and the cyclizing step comprises substitution of the hydroxy with an amine, masked amine or protected amine and cyclizing the 2' and 4' positions.
15. The method of claim 1, wherein the glycosyl donor contains a protected or masked methylamine at the 2' position, and the cyclizing step comprises directly cyclizing the 2' protected or masked methylamine and the 4' position.
16. The method of claim 1, wherein the glycosyl donor contains a protected or masked methylhydroxy at the 2' position, and the cyclizing step comprises substitution of the hydroxy with a thiol, masked thiol or protected thiol and cyclizing the 2' and 4' positions.
17. The method of claim 1, wherein the glycosyl donor contains an acetyl-protected methylhydroxy at the 2' position, and the cyclizing step comprises deacetylation of the hydroxy and cyclizing the 2' and 4' positions.
18. The method of claim 1, wherein the glycosyl donor contains an alcohol protecting group at the 3' position.
19. The method of claim 18, wherein the alcohol protecting group is an ether.
20. The method of claim 18, wherein the alcohol protecting group is heat and acid stable.
21. The method of claim 18, wherein the alcohol protecting group is selected from 4,4'-dimethoxytrityl, acetyl, silyl, benzyl, substituted benzyl or labile ether.
22. The method of claim 1, wherein the glycosyl donor is a pentose, which may be substituted.
23. The method of claim 22, wherein the glycosyl donor is derived from ribose, arabinose or glucose.
24. The method of claim 1, wherein the glycosylation step produces a β-anomer yield of greater than 50%.
25. The method of claim 24, wherein the glycosylation step produces a β:α anomer ratio of greater than 7:3, greater than 8:2, or greater than 9:1.

* * * * *

SEQUENCE LISTING

```
<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: oligonucleotide compound M-11915
<220> FEATURE:
<221> NAME/KEY: misc_feature
<222> LOCATION: (9)..(9)
<223> OTHER INFORMATION: n is an amino-2'-C-bridged bicyclic thymidine
```

<400> SEQUENCE: 1 cttttttgcnc gtctta                                                    16

<210> SEQ ID NO 2
<211> LENGTH: 16
<212> TYPE: DNA
<213> ORGANISM: Artificial Sequence
<220> FEATURE:
<223> OTHER INFORMATION: oligonucleotide compound M-11916
<220> FEATURE:
<221> NAME/KEY: misc_feature
<222> LOCATION: (6)..(6)
<223> OTHER INFORMATION: n is an amino-2'-C-bridged bicyclic thymidine
<220> FEATURE:
<221> NAME/KEY: misc_feature
<222> LOCATION: (9)..(9)
<223> OTHER INFORMATION: n is an amino-2'-C-bridged bicyclic thymidine

<400> SEQUENCE: 2
cttttngcnc gtctta                                                     16

<210> SEQ ID NO 3
<211> LENGTH: 16
<212> TYPE: DNA
<213> ORGANISM: Artificial Sequence
<220> FEATURE:
<223> OTHER INFORMATION: oligonucleotide compound M-11917
<220> FEATURE:
<221> NAME/KEY: misc_feature
<222> LOCATION: (5)..(6)
<223> OTHER INFORMATION: n is an amino-2'-C-bridged bicyclic thymidine
<220> FEATURE:
<221> NAME/KEY: misc_feature
<222> LOCATION: (9)..(9)
<223> OTHER INFORMATION: n is an amino-2'-C-bridged bicyclic thymidine

<400> SEQUENCE: 3
ctttnngcnc gtctta                                                     16

<210> SEQ ID NO 4
<211> LENGTH: 16
<212> TYPE: DNA
<213> ORGANISM: Artificial Sequence
<220> FEATURE:
<223> OTHER INFORMATION: oligonucleotide compound M-11918
<220> FEATURE:
<221> NAME/KEY: misc_feature
<222> LOCATION: (5)..(6)
<223> OTHER INFORMATION: n is an amino-2'-C-bridged bicyclic thymidine

<400> SEQUENCE: 4
ctttnngctc gtctta                                                     16

<210> SEQ ID NO 5
<211> LENGTH: 16
<212> TYPE: DNA
<213> ORGANISM: Artificial Sequence
<220> FEATURE:
<223> OTHER INFORMATION: oligonucleotide compound M-11919
<220> FEATURE:
<221> NAME/KEY: misc_feature
<222> LOCATION: (1)..(1)
<223> OTHER INFORMATION: n is a locked nucleic acid phosphorothioate
      cytidine
<220> FEATURE:
<221> NAME/KEY: misc_feature
<222> LOCATION: (2)..(4)
<223> OTHER INFORMATION: n is a phosphorothioate thymidine
<220> FEATURE:
<221> NAME/KEY: misc_feature
<222> LOCATION: (5)..(6)

```
<223> OTHER INFORMATION: n is an amino-2'-C-bridged bicyclic
      phosphorothioate thymidine
<220> FEATURE:
<221> NAME/KEY: misc_feature
<222> LOCATION: (7)..(7)
<223> OTHER INFORMATION: n is a phosphorothioate guanosine
<220> FEATURE:
<221> NAME/KEY: misc_feature
<222> LOCATION: (8)..(8)
<223> OTHER INFORMATION: n is a locked nucleic acid phosphorothioate
      cytidine
<220> FEATURE:
<221> NAME/KEY: misc_feature
<222> LOCATION: (9)..(9)
<223> OTHER INFORMATION: n is a phosphorothioate thymidine
<220> FEATURE:
<221> NAME/KEY: misc_feature
<222> LOCATION: (10)..(10)
<223> OTHER INFORMATION: n is a locked nucleic acid phosphorothioate
      cytidine
<220> FEATURE:
<221> NAME/KEY: misc_feature
<222> LOCATION: (11)..(11)
<223> OTHER INFORMATION: n is a locked nucleic acid phosphorothioate
      guanosine
<220> FEATURE:
<221> NAME/KEY: misc_feature
<222> LOCATION: (12)..(12)
<223> OTHER INFORMATION: n is a phosphorothioate thymidine
<220> FEATURE:
<221> NAME/KEY: misc_feature
<222> LOCATION: (13)..(13)
<223> OTHER INFORMATION: n is a locked nucleic acid phosphorothioate
      cytidine
<220> FEATURE:
<221> NAME/KEY: misc_feature
<222> LOCATION: (14)..(14)
<223> OTHER INFORMATION: n is a phosphorothioate thymidine
<220> FEATURE:
<221> NAME/KEY: misc_feature
<222> LOCATION: (15)..(15)
<223> OTHER INFORMATION: n is a locked nucleic acid phosphorothioate
      thymidine
<220> FEATURE:
<221> NAME/KEY: misc_feature
<222> LOCATION: (16)..(16)
<223> OTHER INFORMATION: n is a locked nucleic acid adenosine

<400> SEQUENCE: 5
nnnnnnnnnn nnnnnn                                                  16

<210> SEQ ID NO 6
<211> LENGTH: 16
<212> TYPE: DNA
<213> ORGANISM: Artificial Sequence
<220> FEATURE:
<223> OTHER INFORMATION: oligonucleotide compound M-11920
<220> FEATURE:
<221> NAME/KEY: misc_feature
<222> LOCATION: (1)..(1)
<223> OTHER INFORMATION: n is a locked nucleic acid phosphorothioate
      cytidine
<220> FEATURE:
<221> NAME/KEY: misc_feature
<222> LOCATION: (2)..(4)
<223> OTHER INFORMATION: n is a phosphorothioate thymidine
<220> FEATURE:
<221> NAME/KEY: misc_feature
<222> LOCATION: (5)..(6)
<223> OTHER INFORMATION: n is a locked nucleic acid phosphorothioate
      thymidine
<220> FEATURE:
<221> NAME/KEY: misc_feature
<222> LOCATION: (7)..(7)
<223> OTHER INFORMATION: n is a phosphorothioate guanosine
<220> FEATURE:
<221> NAME/KEY: misc_feature
```

<222> LOCATION: (8)..(8)
<223> OTHER INFORMATION: n is a locked nucleic acid phosphorothioate
      cytidine
<220> FEATURE:
<221> NAME/KEY: misc_feature
<222> LOCATION: (9)..(9)
<223> OTHER INFORMATION: n is a phosphorothioate thymidine
<220> FEATURE:
<221> NAME/KEY: misc_feature
<222> LOCATION: (10)..(10)
<223> OTHER INFORMATION: n is a locked nucleic acid phosphorothioate
      cytidine
<220> FEATURE:
<221> NAME/KEY: misc_feature
<222> LOCATION: (11)..(11)
<223> OTHER INFORMATION: n is a locked nucleic acid phosphorothioate
      guanosine
<220> FEATURE:
<221> NAME/KEY: misc_feature
<222> LOCATION: (12)..(12)
<223> OTHER INFORMATION: n is a phosphorothioate thymidine
<220> FEATURE:
<221> NAME/KEY: misc_feature
<222> LOCATION: (13)..(13)
<223> OTHER INFORMATION: n is a locked nucleic acid phosphorothioate
      cytidine
<220> FEATURE:
<221> NAME/KEY: misc_feature
<222> LOCATION: (14)..(14)
<223> OTHER INFORMATION: n is a phosphorothioate thymidine
<220> FEATURE:
<221> NAME/KEY: misc_feature
<222> LOCATION: (15)..(15)
<223> OTHER INFORMATION: n is an amino-2'-C-bridged bicyclic
      phosphorothioate thymidine
<220> FEATURE:
<221> NAME/KEY: misc_feature
<222> LOCATION: (16)..(16)
<223> OTHER INFORMATION: n is a locked nucleic acid adenosine

<400> SEQUENCE: 6
nnnnnnnnnn nnnnnn                                              16

<210> SEQ ID NO 7
<211> LENGTH: 16
<212> TYPE: DNA
<213> ORGANISM: Artificial Sequence
<220> FEATURE:
<223> OTHER INFORMATION: oligonucleotide compound M-10930
<220> FEATURE:
<221> NAME/KEY: misc_feature
<222> LOCATION: (9)..(9)
<223> OTHER INFORMATION: n is an oxo-2'-C-bridged bicyclic thymidine

<400> SEQUENCE: 7 cttttttgcnc gtctta                                             16

<210> SEQ ID NO 8
<211> LENGTH: 16
<212> TYPE: DNA
<213> ORGANISM: Artificial Sequence
<220> FEATURE:
<223> OTHER INFORMATION: oligonucleotide compound M-10924
<220> FEATURE:
<221> NAME/KEY: misc_feature
<222> LOCATION: (1)..(1)
<223> OTHER INFORMATION: n is an oxo-2'-C-bridged bicyclic cytidine
<220> FEATURE:
<221> NAME/KEY: misc_feature
<222> LOCATION: (2)..(6)
<223> OTHER INFORMATION: n is an oxo-2'-C-bridged bicyclic thymidine
<220> FEATURE:
<221> NAME/KEY: misc_feature
<222> LOCATION: (8)..(8)
<223> OTHER INFORMATION: n is an oxo-2'-C-bridged bicyclic cytidine

```
<220> FEATURE:
<221> NAME/KEY: misc_feature
<222> LOCATION: (9)..(9)
<223> OTHER INFORMATION: n is an oxo-2'-C-bridged bicyclic thymidine
<220> FEATURE:
<221> NAME/KEY: misc_feature
<222> LOCATION: (10)..(10)
<223> OTHER INFORMATION: n is an oxo-2'-C-bridged bicyclic cytidine
<220> FEATURE:
<221> NAME/KEY: misc_feature
<222> LOCATION: (12)..(12)
<223> OTHER INFORMATION: n is an oxo-2'-C-bridged bicyclic thymidine
<220> FEATURE:
<221> NAME/KEY: misc_feature
<222> LOCATION: (13)..(13)
<223> OTHER INFORMATION: n is an oxo-2'-C-bridged bicyclic cytidine
<220> FEATURE:
<221> NAME/KEY: misc_feature
<222> LOCATION: (14)..(15)
<223> OTHER INFORMATION: n is an oxo-2'-C-bridged bicyclic thymidine

<400> SEQUENCE: 8
nnnnnngnnn gnnnna                                                16

<210> SEQ ID NO 9
<211> LENGTH: 16
<212> TYPE: DNA
<213> ORGANISM: Artificial Sequence
<220> FEATURE:
<223> OTHER INFORMATION: oligonucleotide compound M-10931

<400> SEQUENCE: 9 cttttttgctc gtctta                                               16

<210> SEQ ID NO 10
<211> LENGTH: 16
<212> TYPE: DNA
<213> ORGANISM: Artificial Sequence
<220> FEATURE:
<223> OTHER INFORMATION: oligonucleotide compound M-10101
<220> FEATURE:
<221> NAME/KEY: misc_feature
<222> LOCATION: (1)..(1)
<223> OTHER INFORMATION: n is a locked nucleic acid phosphorothioate
      cytidine
<220> FEATURE:
<221> NAME/KEY: misc_feature
<222> LOCATION: (2)..(4)
<223> OTHER INFORMATION: n is a phosphorothioate thymidine
<220> FEATURE:
<221> NAME/KEY: misc_feature
<222> LOCATION: (5)..(6)
<223> OTHER INFORMATION: n is a locked nucleic acid phosphorothioate
      thymidine
<220> FEATURE:
<221> NAME/KEY: misc_feature
<222> LOCATION: (7)..(7)
<223> OTHER INFORMATION: n is a phosphorothioate guanosine
<220> FEATURE:
<221> NAME/KEY: misc_feature
<222> LOCATION: (8)..(8)
<223> OTHER INFORMATION: n is a locked nucleic acid phosphorothioate
      cytidine
<220> FEATURE:
<221> NAME/KEY: misc_feature
<222> LOCATION: (9)..(9)
<223> OTHER INFORMATION: n is a phosphorothioate thymidine
<220> FEATURE:
<221> NAME/KEY: misc_feature
<222> LOCATION: (10)..(10)
<223> OTHER INFORMATION: n is a locked nucleic acid phosphorothioate
      cytidine
<220> FEATURE:
<221> NAME/KEY: misc_feature
<222> LOCATION: (11)..(11)
```

```
<223> OTHER INFORMATION: n is a locked nucleic acid phosphorothioate
      guanosine
<220> FEATURE:
<221> NAME/KEY: misc_feature
<222> LOCATION: (12)..(12)
<223> OTHER INFORMATION: n is a phosphorothioate thymidine
<220> FEATURE:
<221> NAME/KEY: misc_feature
<222> LOCATION: (13)..(13)
<223> OTHER INFORMATION: n is a locked nucleic acid phosphorothioate
      cytidine
<220> FEATURE:
<221> NAME/KEY: misc_feature
<222> LOCATION: (14)..(14)
<223> OTHER INFORMATION: n is a phosphorothioate thymidine
<220> FEATURE:
<221> NAME/KEY: misc_feature
<222> LOCATION: (15)..(15)
<223> OTHER INFORMATION: n is a locked nucleic acid phosphorothioate
      thymidine
<220> FEATURE:
<221> NAME/KEY: misc_feature
<222> LOCATION: (16)..(16)
<223> OTHER INFORMATION: n is a locked nucleic acid adenosine

<400> SEQUENCE: 10
nnnnnnnnnn nnnnnn                                                    16

<210> SEQ ID NO 11
<211> LENGTH: 9
<212> TYPE: DNA
<213> ORGANISM: Artificial Sequence
<220> FEATURE:
<223> OTHER INFORMATION: synthesized oligonucleotide DNA_9mer_PO_3LNA-T
<220> FEATURE:
<221> NAME/KEY: misc_feature
<222> LOCATION: (2)..(2)
<223> OTHER INFORMATION: n is a locked nucleic acid thymidine
<220> FEATURE:
<221> NAME/KEY: misc_feature
<222> LOCATION: (5)..(5)
<223> OTHER INFORMATION: n is a locked nucleic acid thymidine
<220> FEATURE:
<221> NAME/KEY: misc_feature
<222> LOCATION: (7)..(7)
<223> OTHER INFORMATION: n is a locked nucleic acid thymidine

<400> SEQUENCE: 11 gnganangc                                                             9

<210> SEQ ID NO 12
<211> LENGTH: 9
<212> TYPE: DNA
<213> ORGANISM: Artificial Sequence
<220> FEATURE:
<223> OTHER INFORMATION: synthesized oligonucleotide DNA_9mer_PO_3LNA-T
<220> FEATURE:
<221> NAME/KEY: misc_feature
<222> LOCATION: (2)..(2)
<223> OTHER INFORMATION: n is an amino locked nucleic acid thymidine
<220> FEATURE:
<221> NAME/KEY: misc_feature
<222> LOCATION: (5)..(5)
<223> OTHER INFORMATION: n is an amino locked nucleic acid thymidine
<220> FEATURE:
<221> NAME/KEY: misc_feature
<222> LOCATION: (7)..(7)
<223> OTHER INFORMATION: n is an amino locked nucleic acid thymidine

<400> SEQUENCE: 12 gnganangc                                                             9
```